(12) United States Patent
Ivachtchenko et al.

(10) Patent No.: US 8,829,002 B2
(45) Date of Patent: Sep. 9, 2014

(54) SUBSTITUTED METHYL AMINES, SEROTONIN 5-HT6 RECEPTOR ANTAGONISTS, METHODS FOR PRODUCTION AND USE THEREOF

(76) Inventors: Alexandre Vasilievich Ivachtchenko, Encinitas, CA (US); Oleg Dmitrievich Mitkin, Khimki (RU); Madina Georgievna Kadieva, Podosinki (RU)

( * ) Notice: Subject to any disclaimer, the term of this patent is extended or adjusted under 35 U.S.C. 154(b) by 0 days.

(21) Appl. No.: 13/993,131

(22) PCT Filed: Dec. 13, 2011

(86) PCT No.: PCT/RU2011/000981
§ 371 (c)(1), (2), (4) Date: Jun. 11, 2013

(87) PCT Pub. No.: WO2012/087182
PCT Pub. Date: Jun. 28, 2012

(65) Prior Publication Data
US 2013/0267536 A1   Oct. 10, 2013

(30) Foreign Application Priority Data

Dec. 21, 2010 (RU) ................................ 2010152052

(51) Int. Cl.
C07D 471/04 (2006.01)
C07D 295/135 (2006.01)
C07D 215/42 (2006.01)
C07D 213/40 (2006.01)
C07D 413/04 (2006.01)
C07D 317/36 (2006.01)
C07D 413/14 (2006.01)

(52) U.S. Cl.
USPC .......... 514/253.04; 514/253.075; 514/255.03; 514/299; 514/312; 514/357; 514/376; 546/112; 546/153; 546/334; 544/363; 544/395; 544/398; 548/225

(58) Field of Classification Search
USPC .......... 514/253.04, 253.07, 255.03, 299, 312, 514/357, 376; 546/112, 153, 334; 544/363, 544/395, 398; 548/225
See application file for complete search history.

(56) References Cited

U.S. PATENT DOCUMENTS 6,737,426 B1 * 5/2004 Gericke et al. ........... 514/252.13

OTHER PUBLICATIONS

Hellwinkel et al., Chemische Berichte (1985), 118(1), 66-85.*

* cited by examiner

Primary Examiner — Niloofar Rahmani

(57) ABSTRACT

The present invention relates to novel substituted methyl-amines, serotonin 5-HT$_6$ receptor antagonists, to active components, pharmaceutical compositions, method for prophylaxis and treatment of CNS diseases and "molecular tools", in which novel substituted methyl-amines represent compounds of the general formula 1 and their crystalline forms and pharmaceutically acceptable salts,

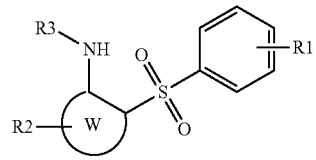

wherein: W represents benzene, naphthalene, indolizine, quinoline or oxazole cycle; R1=H, F, Cl; R2 represents hydrogen, fluoro, methyl, phenyl, thienyl, furan-2-yl, pyridyl, piperazin-1-yl or 4-methylpiperazin-1-yl; R3 represents cyclopropyl or optionally substituted methyl; with the exception of the compounds in which W simultaneously represents oxazole cycle and R2=phenyl or pyridyl.

15 Claims, 10 Drawing Sheets

Figure 1:
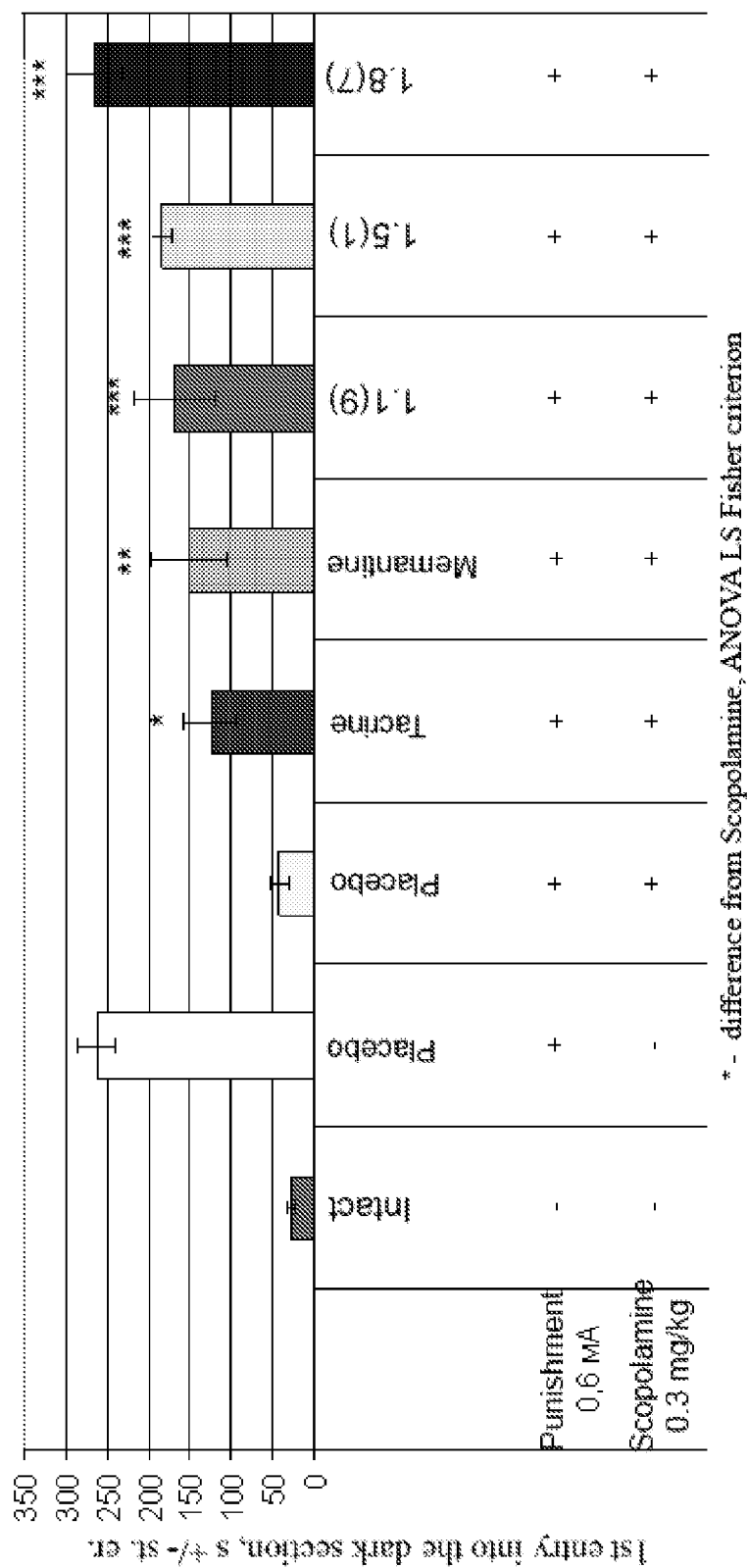

SUBSTITUTED METHYL AMINES, SEROTONIN 5-HT6 RECEPTOR ANTAGONISTS, METHODS FOR PRODUCTION AND USE THEREOF

CROSS REFERENCE TO RELATED APPLICATIONS

This application is a National stage of International application PCT/RU2011/000981 filed Dec. 13, 2011, which claims benefit of foreign priority to the Russian Federation application RU 2010152052 of Dec. 21, 2010. The priority applications are hereby incorporated by reference in their entirety.

FIELD OF THE INVENTION

The invention relates to novel substituted methyl-amines, to novel serotonin 5-$HT_6$ receptor antagonists, to novel active components, pharmaceutical compositions, therapeutic kits, method for treatment and molecular instruments. In the origin of pharmacological effect of novel active components is their ability to interact with serotonin 5-$HT_6$ receptors playing a key role in treatment of central nervous system (CNS) diseases, in particular, Alzheimer's disease (AD), Huntington's disease, schizophrenia, other neurodegenerative diseases, cognitive disorders and obesity.

PRIOR ART

Usefulness of effective and selective antagonists of serotonin 5-$HT_6$ receptors for treatment of CNS diseases, in particular, schizophrenia, AD and other neurodegenerative diseases and cognitive disorders was proved conclusively in clinical practice and their usage is regarded to be very perspective in medicine of future [Holenz J., Pauwels P. J., Diaz J. L., Merce R., Codony X., Buschmann H. Medicinal chemistry strategies to 5-$HT_6$ receptor ligands as potential cognitive enhancers and antiobesity agents. Drug Disc. Today. 2006; 11:283-299]. At mammals these receptors are located exclusively in central nervous system (CNS), and mainly in parts of brain responsible for training and memory [Ge'rard C., Martres M.-P., Lefe'vre K., Miguel M.-C., Verge' D., Lanfumey L., Doucet E., Hamon M., El Mestikawy S. Immuno-localisation of serotonin 5-$HT_6$ receptor-like material in the rat central nervous system. Brain Research. 1997; 746:207-219]. Besides, it was shown [Dawson L. A., Nguyen H. Q., Li P. The 5-HT(6) receptor antagonist SB-271046 selectively enhances excitatory neurotransmission in the rat frontal cortex and hippocampus. Neuropsychopharmacology. 2001; 25:662-668], that 5-$HT_6$ receptors are modulators of the whole number of neuromediator systems including cholinergic, noradrenergic, glutamatergic and dopaminergic. Taking into account the fundamental role of these systems in normal cognitive processes and their dysfunction at neurodegeneration, exclusive role of 5-$HT_6$ receptors in forming normal and "pathological" memory becomes obvious.

It was shown in a large number of nowadays publications that blocking of 5-$HT_6$ receptors leads to considerable enhancement of memory consolidation in various animal models of training-memorizing-reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. Neuropsychopharmacology. 2004; 29:93-100. Riemer C., Borroni E., Levet-Trafit B., Martin J. R., Poli S., Porter R. H., Bos M. Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-$HT_6$ receptor antagonist. J. Med. Chem. 2003; 46:1273-1276. King M. V., Woolley M. L., Topham I. A., Sleight A. J., Marsden C. A., Fone K. C. 5-HT6 receptor antagonists reverse delay-dependent deficits in novel object discrimination by enhancing consolidation an effect sensitive to NMDA receptor antagonism. Neuropharmacology 2004; 47:195-204]. It was also demonstrated that considerable enhancement of cognitive functions in aged rats in Morrison's water maze experiment took place under the action of 5-$HT_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. Neuropsychopharmacology. 2004; 29:93-100]. Recently more thorough understanding of 5-$HT_6$ receptor function in cognitive processes and more accurate conceptions concerning possible pharmacophoric properties of their antagonists were achieved. [Holenz J., Pauwels P. J., Diaz J. L., Merce R., Codony X., Buschmann H. Medicinal chemistry strategies to 5-$HT_6$ receptor ligands as potential cognitive enhancers and antiobesity agents. Drug Disc. Today. 2006; 11:283-299]. This resulted in preparation of highly affine selective ligands ("molecular tools"), and afterwards clinical candidates. At present a number of 5-$HT_6$ receptor antagonists are at various phases of clinical trials as potential ingredients for treatment of AD, Huntington's disease, schizophrenia (antipsychotic) and other neurodegenerative and cognitive diseases (Table 1) [http://integrity.prous.com].

TABLE 1

5-$HT_6$ Receptor antagonists as drug candidates.

| Medicament | Clinical phase of testing | Developer | Therapeutic group |
|---|---|---|---|
| Dimebon ™ | Phase III | Medivation (USA) | Alzheimer's disease treatment |
| SGS-518 | Phase II | Lilly, Saegis | Cognitive diseases treatment |
| SB-742457 | Phase II | GlaxoSmithKline | Alzheimer's disease treatment; Antipsychotic |
| Dimebon* | Phase I/IIa | Medivation (USA) | Huntington's disease treatment |
| Dimebon* | Phase II | (Russia) | Schizophrenia |
| PRX-07034 | Phase I | Epix Pharm. | Obesity treatment; Antipsychotic; Cognitive diseases treatment |
| SB-737050A | Phase II | GlaxoSmithKline | Antipsychotic |
| BVT-74316 | Phase I | Biovitrum | Obesity treatment |
| SAM-315 | Phase I | Wyeth Pharm. | Alzheimer's disease treatment |
| SYN-114 | Phase I | Roche, Synosis Ther. | Cognitive diseases treatment |
| BGC-20-761 | Preclinical | BTG (London) | Antipsychotic; Cognitive diseases treatment |
| FMPO | Preclinical | Lilly | Antipsychotic |
| Dimebon ™ | Preclinical | (Russia) | Insult treatment |

Another attractive property of 5-$HT_6$ receptor antagonists is their ability to suppress appetite that can lead to the development of essentially novel remedies for lowering of overweight and obesity on their basis. [Vicker S. P., Dourish C. T. Serotonin receptor ligands and the treatment of obesity. Curr.

*Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. Davies S. L. Drug discovery targets: 5-HT$_6$ receptor. *Drug Future.* 2005; 30:479-495], mechanism of their action is based on suppression of γ-aminobutyric acid signaling by 5-HT$_6$ receptor antagonists and increasing of α-melanocyte-stimulating hormone emission, that, finally, results in lowering of food demand [Woolley M. L. 5-HT$_6$ receptors. *Curr. Drug Targets CNS Neurol. Disord.* 2004; 3:59-79]. Now two 5-HT$_6$ receptor antagonists are at the first phase of clinical trials as drug candidates for obesity treatment (Table 1) [http://integrity.prous.com].

In this context searching for new selective and effective serotonin 5-HT$_6$ receptor antagonists seems to be original and perspective approach to the development of novel drug substances for treating broad spectrum of CNS diseases, among them neurological and neurodegenerative diseases and cognitive disorders.

There are many publications concerning various biologically active sulfonyl substituted azaheterocycles, among them serotonin 5-HT$_6$ receptor ligands. For example, substituted 1-(2-aminoethyl)-4-arylsulfonyl-pyrazoles [WO 2003057674 A1], 7-amino-3-sulfonyl-pyrazolo[1,5-a]pyrimidines [EP 941994 A1, 1999] and some substituted methylamines are known [WO00037452A1, WO00138316 A2, EP00930302A2, WO00198279 A2].

For the purpose of the development of novel highly effective medicaments the authors of the invention carried out widespread investigation in the field of substituted methylamines, as a result of which novel methyl-amines which are 5-HT$_6$ receptor antagonists, and novel active component for pharmaceutical composition were found, and possibility of its usage for prophylaxis and treatment of CNS diseases was checked up.

DISCLOSURE OF THE INVENTION

In the context of the invention, the terms are generally defined as follows:

"Agonists" mean ligands being bound with receptors of definite type actively promote transferring their specific signal and by that cause the biological answer of the cell.

"Active component" (drug-substance) means a physiologically active compound of synthetic or other (biotechnological, vegetable, animal, bacterial and others) origins exhibiting pharmacological activity which is an active ingredient of pharmaceutical composition employed in preparation and production of medicaments.

"Alkyl" means aliphatic hydrocarbon straight or branched group with 1-12 carbon atoms. Branched means alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclyl, annelated arylcycloalkenyl, annelated arylheterocyclenyl, annelated arylheterocyclyl, alkoxycarbonyl, aralkoxycarbonyl, heteroaralkyloxycarbonyl or $R_k^a R_{k+1}^a N-$, $R_k^a R_{k+1}^a NC(=O)-$, $R_k^a R_{k+1}^a NC(=S)-$, $R_k^a R_{k+1}^a NSO_2-$, where $R_k^a$ and $R_{k+1}^a$ independently of each other represent "amino group" substituent, the meanings of which are defined in this section, for example, hydrogen, alkyl, aryl, aralkyl, heteroaralkyl, heterocyclyl or heteroaryl, or $R_k^a$ and $R_{k+1}^a$ together with the N-atom, they are attached to, form through $R_k^a$ and $R_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N-$, $R_k^a R_{k+1}^a NC(=O)-$, annelated arylheterocyclenyl, annelated arylheterocyclyl.

"Antagonists" mean ligands being bound with definite receptors do not cause active cellular responses. Antagonists prevent linkage between agonists and receptors and by that block specific signal transferring.

"Aryl" means aromatic mono- or polycyclic system with 6-14 carbon atoms, predominantly from 6 to 10 carbon atoms. Aryl may have one or more "cyclic system substituents" of the same or different structure. Phenyl, substituted phenyl, naphthyl, or substituted naphthyl are the representatives of aryl groups. Aryl could be annelated with saturated cyclic system or heterocycle.

"Arylsulfonyl" means aryl-SO$_2$— group, where the meanings of aryl are defined in this section.

"Arylsulfanyl" means aryl-S— group, where the meanings of aryl are defined in this section. Phenylsulfanyl and 2-naphthylsulfanyl are the representatives of arylsulfanyl groups.

"Aromatic" radical means a radical derived at removal of hydrogen atom from aromatic C—H bond. "Aromatic" radical includes aryl and heteroaryl cycles defined in this section. Aryl and heteroaryl cycles may additionally include substituents—aliphatic or aromatic radicals defined in this section. The representatives of aromatic radicals include aryl, annelated cycloalkenylaryl, annelated cycloalkylaryl, annelated heterocyclylaryl, annelated heterocyclenylaryl, heteroaryl, annelated cycloalkylheteroaryl, annelated cycloalkenylheteroaryl, annelated heterocyclenylheteroaryl and annelated heterocyclylheteroaryl.

"Aromatic cycle" means a plane cyclic system, in which all atoms take part in the construction of a common conjugation system comprising, according to Hückel rule, (4 n+2) π-electrons (n is a whole nonnegative number). Benzene, naphthalene, anthracene and others are the representatives of aromatic cycles. In the case of "heteroaromatic cycles" π-electrons and p-electrons of heteroatoms participate in the conjugation, so that their total number is equal to (4 n+2) as well. Pyridine, thiophene, pyrrole, furan, thiazole and others are the representatives of such cycles. Aromatic cycle may have one or more "cyclic system substituents" and could be annelated to nonaromatic cycle, heteroaromatic or heterocyclic system.

"Halogen" means fluorine, chlorine, bromine and iodine. Preference is given to fluorine, chlorine and bromine.

"Heteroaryl" means aromatic mono- or polycyclic system with 5-14 carbon atoms, preferably from 5 to 10, wherein one or more carbon atoms are substituted by one or more heteroatoms, such as N, S or O. Prefix "aza", "oxa" or "thia" before "heteroaryl" means that N, O or S atoms are introduced in the appropriate cyclic fragment. N-Atom of heteroaryl cycle could be oxidized to N-oxide. Heteroaryl may have one or more "cyclic system substituents" of the same or different structure. Pyrrolyl, furan-2-yl, thienyl, pyridyl, pyrazinyl, pyrimidinyl, isoxazolyl, isothiazolyl, tetrazolyl, oxazolyl, thiazolyl, pyrazolyl, furazanyl, triazolyl, 1,2,4-thiadiazolyl, pyridazinyl, quinoxalinyl, phthalazinyl, imidazo[1,2-a]pyridinyl, imidazo[2,1-b]thiazolyl, benzo furazanyl, indolyl, azaindolyl, benzoimidazolyl, benzothiazenyl, quinolinyl, imidazolyl, thienopyridyl, quinazolinyl, thienopyrimidinyl, pyrrolopyridinyl, imidazopyridyl, isoquinolinyl, benzoazaindolyl, 1,2,4-triazinyl, thienopyrrolyl, furopyrrolyl and others are the representatives of heteroaryl radicals.

"Hydrate" means stoichiometric or nonstoichiometric compositions of the compounds or their salts with water.

"Substituent" means a chemical radical attached to a scaffold (fragment), for example, "alkyl substituent", "amino group substituent", "carbamoyl substituent", and "cyclic system substituent", the meanings of which are defined in this section.

"Medicament"—is a compound (or a mixture of compounds in the form of pharmaceutical composition) in the form of tablets, capsules, injections, ointments and other drug products intended for restoration, improvement or modification of physiological functions at humans and animals, and for treatment and prophylaxis of diseases, diagnostics, anaesthesia, contraception, cosmetology and others.

"Ligands" (from latin ligo) represent chemical compounds (small molecule, peptide, protein, inorganic ion, and others) capable to interact with receptors which convert this interaction into a specific signal.

"Lower alkyl" means straight or branched alkyl with 1-4 carbon atoms.

"Sulfanyl" means R—S— group, in which R represents alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl the meanings of which are defined in this section.

"Sulfonyl" means R—SO$_2$— group, in which R represents alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings of which are defined in this section.

"Therapeutic kit" is simultaneously administered combination of two or more drug substances with different mechanism of pharmacological action and aimed at different biotargets taking part in pathogenesis of the disease.

"Cycloalkyl" means saturated mono- or polycyclic system consisting of 3-10 carbon atoms. Cycloalkyl may have one or more "cyclic system substituents" of the same or different structure. Cyclopropyl, cyclobutyl, cyclopentyl, cyclohexyl, decalynyl, norbonyl, adamant-1-yl and so on are representatives of cycloalkyl groups. Cycloalkyl could be annelated with aromatic cycle or heterocycle. The preferred "cyclic system substituents" are alkyl, aralkyl, aralkoxy, hydroxyl, or $R_k{}^a R_{k+1}{}^a N$, the meanings of which are defined in this section.

"Pharmaceutical composition" means composition comprising, at least, one of the compounds of the general formula 1 and, at least, one of the components selected from pharmaceutically acceptable and pharmacologically compatible fillers, solvents, diluents, auxiliary, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dosage. Examples of suitable suspending agents are: ethoxylated isostearyl alcohol, polyoxyethene, sorbitol and sorbitol ether, microcrystalline cellulose, aluminum metahydroxide, bentonite, agar-agar and tragacant and mixtures thereof as well. Protection against microorganism action can be provided by various antibacterial and antifungal agents, such as: parabens, chlorobutanol, sorbic acid, and similar compounds. Composition may also contain isotonic agents, such as: sugar, sodium chloride, and similar compounds. Prolonged effect of the composition may be achieved by agents slowing down absorption of the active ingredient, for example, aluminum monostearate and gelatin. Examples of suitable carriers, solvents, diluents and delivery agents include water, ethanol, polyalcohols and their mixtures, natural oils (such as olive oil) and injection-grade organic esters (such as ethyl oleate). Examples of fillers are: lactose, milk-sugar, sodium citrate, calcium carbonate, calcium phosphate and the like. Examples of disintegrators and distributors are: starch, alginic acid and its salts, and silicates. Examples of suitable lubricants are: magnesium stearate, sodium lauryl sulfate, talc and polyethylene glycol of high molecular weight. Pharmaceutical composition for peroral, sublingval, transdermal, intramuscular, intravenous, subcutaneous, local or rectal administration of active ingredient, alone or in combination with another active compound may be administered to humans and animals in standard administration form, or in mixture with traditional pharmaceutical carriers. Suitable standard administration forms include peroral forms such as tablets, gelatin capsules, pills, powders, granules, chewing-gums and peroral solutions or suspensions, for example, therapeutic kit; sublingval and transbuccal administration forms; aerosols; implants; local, transdermal, subcutaneous, intramuscular, intravenous, intranasal or intraocular forms and rectal administration forms.

"Pharmaceutically acceptable salt" means relatively nontoxic both organic and inorganic salts of acids and bases disclosed in this invention. Salts could be prepared in situ during the processes of synthesis, isolation or purification of compounds or they could be prepared specially. In particular, salts of bases could be prepared starting from purified bases disclosed in the invention and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of such salt properties is given in: Berge S. M., et al., "Pharmaceutical Salts" J. Pharm. Sci., 1977, 66: 1-19). Salts of the disclosed acids may be prepared by reaction of purified acids specifically with suitable base; moreover, metal salts and amine salts may be synthesized too. Metal salts are salts of sodium, potassium, calcium, barium, magnesium, lithium and aluminum; sodium and potassium salts being preferred. Suitable inorganic bases from which metal salts can be prepared are: sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of disclosed acid salts are amines and amino acids the basicity of which is sufficient enough to produce stable salt and suitable for medical purposes use (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as holine, tetramethylammonium, tetraethylammonium, and the like. Amino acids may be selected from the main aminoacids—lysine, ornithine and arginine.

The purpose of the present invention is novel substituted methyl-amines exhibiting activity towards 5-HT$_6$ receptors.

The purpose in view is achieved by substituted methyl-amines of the general formula 1, their crystalline forms and pharmaceutically acceptable salts thereof,

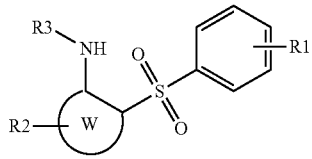

1 wherein:
W represents naphthalene, indolizine or quinoline;
R1 represents hydrogen, fluoro, chloro, methyl;
R2 represents hydrogen, fluoro, methyl, phenyl, thiophen-2-yl, furan-2-yl, pyridyl, piperazin-1-yl or 4-methylpiperazin-1-yl;
R3 represents methyl;
or
W represents benzene, R3 has the above meanings;
R1 represents 3-Cl, R2 represents 3-piperazin-1-yl or 3-(4-methylpiperazin-1-yl);
or
R1 represents hydrogen,
R2 represents phenyl or pyridyl;
or
R1 represents hydrogen, fluoro, chloro, methyl;
R2 represents 4-piperazin-1-yl or 4-(4-methylpiperazin-1-yl);
or
W represents oxazole, R3 represents optionally substituted methyl;
R1 represents fluoro or chloro,
R2 represents methyl,
or
R1 represents hydrogen, fluoro, chloro, methyl;
R2 represents piperazin-1-yl, 4-methylpiperazin-1-yl,
or
R1 represents fluoro, chloro or methyl;
R2 represents furan-2-yl,
or
R1 represents hydrogen, fluoro, chloro, methyl;
R2 represents furan-2-yl,
R3 represents (tetrahydrofuran-2-yl)methyl,
or
R1 represents hydrogen, fluoro, chloro, methyl;
R2 represents thiophen-2-yl,
R3 represents 2-methoxyethyl,
or
R1 represents fluoro of chloro,
R2 represents thiophen-2-yl,
R3 represents methyl.

The preferable methyl-amines are compounds 1.1-1.8, where W represents optionally substituted 1,2-phenylene (1.1); 1,2-naphthalinene (1.2.1, 1.2.2, 1.3); 1,2-indolizinene (1.4.1, 1.4.2); 3,4-quinolinene (1.5*И* 1.7), 5,6-quinolinene (1.6) or 4,5-oxazolene (1.8),

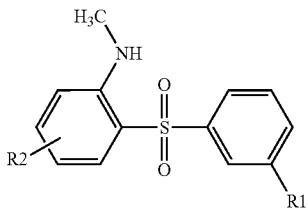

1.1

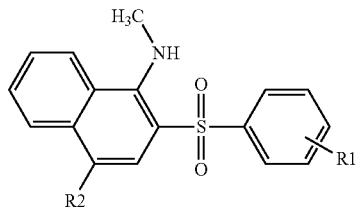

1.2.1

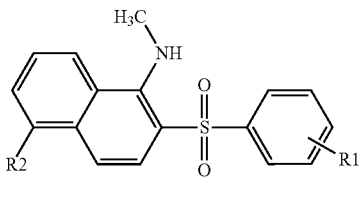

1.2.2

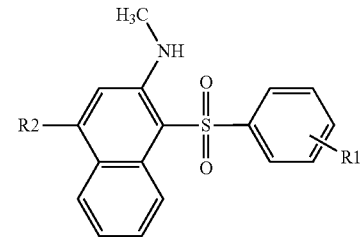

1.3

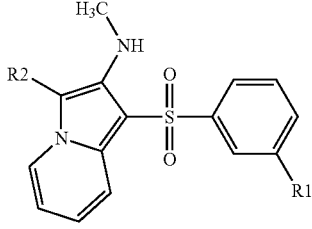

1.4.1

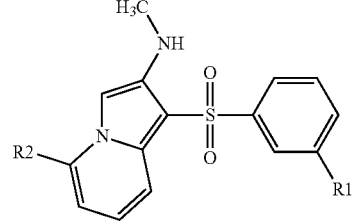

1.4.2

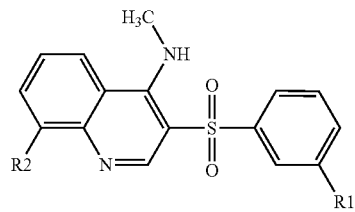

1.5

-continued

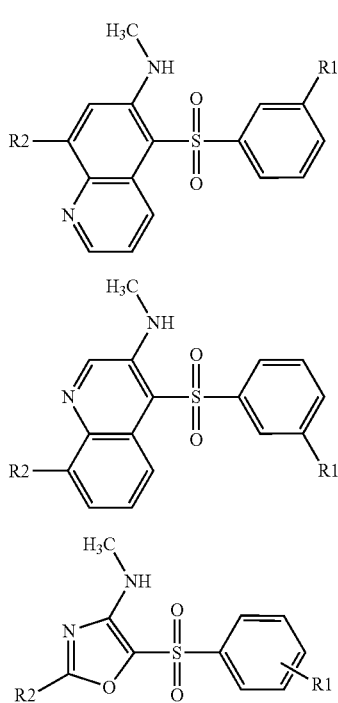

wherein R1 and R2 have the above meanings for the appropriate meaning of W.

The preferable methyl-amines are also compounds of the general formulas 1.1-1.8, where R1=H, 3-F or 3-Cl.

The preferable methyl-amines are also compounds of the general formulas 1.1-1.8, where R2 represents hydrogen, methyl, piperazin-1-yl or 4-methylpiperazin-1-yl.

The more preferable methyl-amines of the general formula 1.1 are compounds selected from the group consisting of:
methyl-[3-(piperazin-1-yl-6-(3-chlorophenylsulfonyl)phenyl]-amine 1.1(2),
methyl-[3-(4-methyl-piperazin-1-yl)-6-(3-chlorophenylsulfonyl)phenyl]-amine 1.1(5),

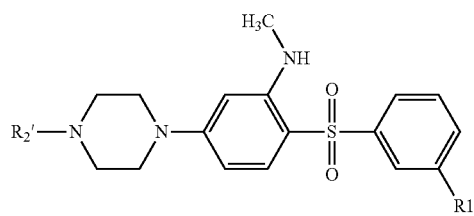

1.1(2): R1 = 3-Cl, R₂' = H.
1.1(5): R1 = 3-Cl, R₂' = CH₃.

methyl-(4-piperazin-1-yl-6-phenylsulfonylphenyl)-amine 1.1(7),
methyl-[4-piperazin-1-yl-6-(3-chlorophenylsulfonyl)phenyl]-amine 1.1(8),
methyl-[4-piperazin-1-yl-6-(3-fluorophenylsulfonyl)phenyl]-amine 1.1(9),
methyl-[4-(4-methylpiperazin-1-yl)-6-phenylsulfonylphenyl]-amine 1.1(10),
methyl-[4-(4-methylpiperazin-1-yl)-6-(3-chlorophenylsulfonyl)phenyl]-amine 1.1(11),
methyl-[4-(4-methylpiperazin-1-yl)-6-(3-fluorophenylsulfonyl)phenyl]-amine 1.1(12),

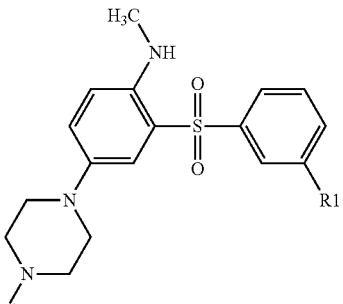

1.1(7): R1 = H, R'₂ = H
1.1(8): R1 = Cl, R'₂ = H
1.1(9): R1 = F, R'₂ = H
1.1(10): R1 = H, R'₂ = CH₃
1.1(11): R1 = Cl, R'₂ = CH₃
1.1(12): R1 = F, R'₂ = CH₃

N-methyl-N-[4-(phenylsulfonyl)-1,1'-biphenyl-3-yl]amine 1.1(13),
methyl-(5-pyridin-3-yl-2-phenylsulfonylphenyl)-amine 1.1(14).

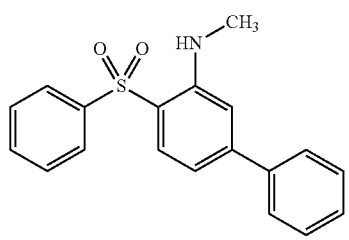 [SMILES: CNc1cc(-c2ccccc2)ccc1S(=O)(=O)c1ccccc1]

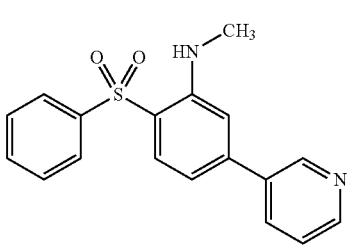 [SMILES: CNc1cc(-c2cccnc2)ccc1S(=O)(=O)c1ccccc1]

The more preferable methyl-amines of the general formulas 1.2.1 and 1.2.2 are the compounds selected from the group consisting of:
methyl-(4-piperazin-1-yl-2-phenylsulfonylnaphthalen-1-yl)-amine 1.2.1(1),
methyl-[4-piperazin-1-yl-2-(3-chlorophenylsulfonyl)naphthalen-1-yl]-amine 1.2.1(2),
methyl-[4-piperazin-1-yl-2-(3-fluorophenylsulfonyl)naphthalen-1-yl]-amine 1.2.1(3),
methyl-[4-(4-methylpiperazin-1-yl)-2-phenylsulfonylnaphthalen-1-yl)-amine 1.2.1(4),
methyl-[4-(4-methylpiperazin-1-yl)-2-(3-chlorophenylsulfonyl)naphthalen-1-yl]-amine 1.2.1(5),
methyl-[4-(4-methylpiperazin-1-yl)-2-(3-fluorophenylsulfonyl)naphthalen-1-yl]-amine 1.2.1(6),

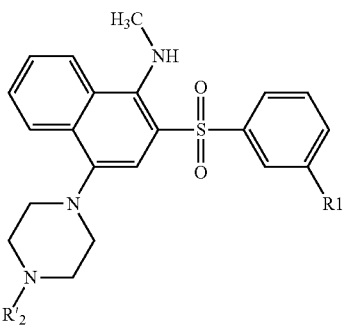

1.2.1(1-6)

1.2.1(1): R1 = H, R'$_2$ = H;
1.2.1(2): R1 = Cl, R'$_2$ = H;
1.2.1(3): R1 = F, R'$_2$ = H;
1.2.1(4): R1 = H, R'$_2$ = CH$_3$;
1.2.1(5): R1 = Cl, R'$_2$ = CH$_3$;
1.2.1(6): R1 = F, R'$_2$ = CH$_3$;

methyl-(5-piperazin-1-yl-2-phenylsulfonylnaphthalen-1-yl)-amine 1.2.2(1),
methyl-[5-piperazin-1-yl-2-(3-chlorophenylsulfonyl)naphthalen-1-yl]-amine 1.2.2(2),
methyl-[5-piperazin-1-yl-2-(3-fluorophenylsulfonyl)naphthalen-1-yl]-amine 1.2.2(3),
methyl-[5-(4-methylpiperazin-1-yl)-2-phenylsulfonylnaphthalen-1-yl]-amine 1.2.2(4),
methyl-[5-(4-methylpiperazin-1-yl)-2-(3-chlorophenylsulfonyl)naphthalen-1-yl]-amine 1.2.2(5),
methyl-[5-(4-methylpiperazin-1-yl)-2-(3-fluorophenylsulfonyl)naphthalen-1-yl]-amine 1.2.2(6),

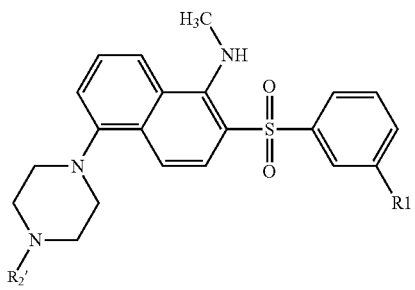

1.2.2(1-6)

1.2.2(1): R1 = H, R$_2$' = H.
1.2.2(2): R1 = 3-Cl, R$_2$' = H.
1.2.2(3): R1 = 3-F, R$_2$' = H.
1.2.2(4): R1 = H, R$_2$' = CH$_3$.
1.2.2(5): R1 = 3-Cl, R$_2$' = CH$_3$.
1.2.2(6): R1 = 3-F, R$_2$' = CH$_3$.

The more preferable methyl-amines of the general formula 1.3 are the compounds selected from the group consisting of:
methyl-(4-piperazin-1-yl-1-phenylsulfonylnaphthalen-2-yl)-amine 1.3(1),
methyl-[4-piperazin-1-yl-1-(1-chlorophenylsulfonyl)naphthalen-2-yl]-amine 1.3(2),
methyl-[4-piperazin-1-yl-1-(1-fluorophenylsulfonyl)naphthalen-2-yl]-amine 1.3(3),
methyl-[4-(4-methylpiperazin-1-yl)-1-phenylsulfonylnaphthalen-2-yl]-amine 1.3(4),
methyl-[4-(4-methylpiperazin-1-yl)-1-(3-chlorophenylsulfonyl)naphthalen-2-yl]-amine 1.3(5),
methyl-[4-(4-methylpiperazin-1-yl)-1-(3-fluorophenylsulfonyl)naphthalen-2-yl]-amine 1.3(6).

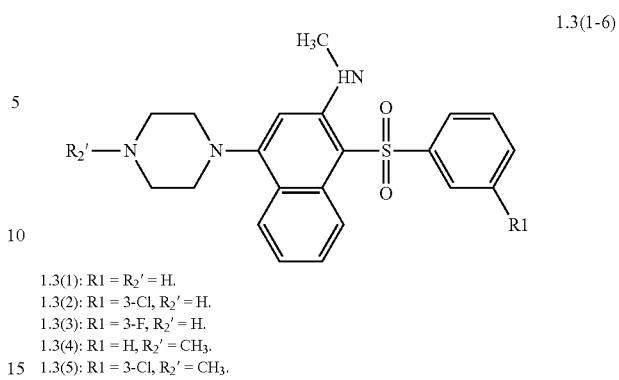

1.3(1-6)

1.3(1): R1 = R$_2$' = H.
1.3(2): R1 = 3-Cl, R$_2$' = H.
1.3(3): R1 = 3-F, R$_2$' = H.
1.3(4): R1 = H, R$_2$' = CH$_3$.
1.3(5): R1 = 3-Cl, R$_2$' = CH$_3$.
1.3(6): R1 = 3-F, R$_2$' = CH$_3$.

The more preferable methyl-amines of the general formulas 1.4.1 and 1.4.2 are the compounds selected from the group consisting of
methyl-(1-phenylsulfonylindolizin-2-yl)-amine 1.4.1(1),
methyl-[1-(3-chlorophenylsulfonyl)indolizin-2-yl]-amine 1.4.1(2),
methyl-[1-(3-fluorophenylsulfonyl)indolizin-2-yl]-amine 1.4.1(3),
methyl-(3-methyl-1-phenylsulfonylindolizin-2-yl)-amine 1.4.1(4),
methyl-[3-methyl-1-(3-chlorophenylsulfonyl)indolizin-2-yl]-amine 1.4.1(5),
methyl-[3-methyl-1-(3-fluorophenylsulfonyl)indolizin-2-yl]-amine 1.4.1(6),
methyl-(3-piperazin-1-yl-1-phenylsulfonylindolizin-2-yl)-amine 1.4.1(7),
methyl-[3-piperazin-1-yl-1-(3-chlorophenylsulfonyl)indolizin-2-yl]-amine 1.4.1(8),
methyl-[3-piperazin-1-yl-1-(3-fluorophenylsulfonyl)indolizin-2-yl]-amine 1.4.1(9),
methyl-[3-(4-methylpiperazin-1-yl)-1-phenylsulfonylindolizin-2-yl]-amine 1.4.1(10),
methyl-[3-(4-methylpiperazin-1-yl)-1-(3-chlorophenylsulfonylindolizin-2-yl]-amine 1.4.1(11),
methyl-[3-(4-methylpiperazin-1-yl)-1-(3-fluorophenylsulfonylindolizin-2-yl]-amine 1.4.1(12),

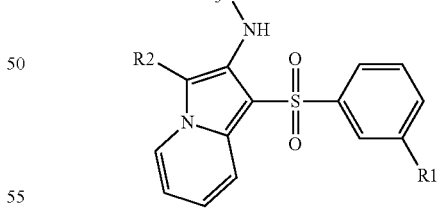

1.4.1(1-12)

1.4.1(1): R1 = R2 = H,
1.4.1(2): R1 = 3-Cl, R2 = H,
1.4.1(3): R1 = 3-F, R2 = H,
1.4.1(4): R1 = H, R2 = CH$_3$,
1.4.1(5): R1 = 3-Cl, R2 = CH$_3$,
1.4.1(6): R1 = 3-F, R2 = CH$_3$,
1.4.1(7): R1 = H, R2 = piperazin-1-yl;
1.4.1(8): R1 = 3-Cl, R2 = piperazine-1-yl;
1.4.1(9): R1 = 3-F, R2 = piperazine-1-yl;
1.4.1(10): R1 = H, R2 = 4-methylpiperazine-1-yl;
1.4.1(11): R1 = 3-Cl, R2 = 4-methylpiperazine-1-yl;
1.4.1(12): R1 = 3-F, R2 = 4-methylpiperazine-1-yl;

methyl-(5-methyl-1-phenylsulfonylindolizin-2-yl)-amine 1.4.2(1), methyl-[5-methyl-1-(3-chlorophenylsulfonyl)indolizin-2-yl]-amine 1.4.2(2), methyl-[5-methyl-1-(3-fluorophenylsulfonyl)indolizin-2-yl]-amine 1.4.2(3), methyl-(5-piperazin-1-yl-1-phenylsulfonylindolizin-2-yl)-amine 1.4.2(4), methyl-[5-piperazin-1-yl-1-(3-chlorophenylsulfonyl)indolizin-2-yl]-amine 1.4.2(5), methyl-[5-piperazin-1-yl-1-(3-fluorophenylsulfonyl)indolizin-2-yl]-amine 1.4.2(6), methyl-[5-(4-methylpiperazin-1-yl)-1-phenylsulfonylindolizin-2-yl]-amine 1.4.2(7), methyl-[5-(4-methylpiperazin-1-yl)-1-(3-chlorophenylsulfonyl)indolizin-2-yl]-amine 1.4.2(8), methyl-[5-(4-methylpiperazin-1-yl)-1-(3-fluorophenylsulfonyl)indolizin-2-yl]-amine 1.4.2(9),

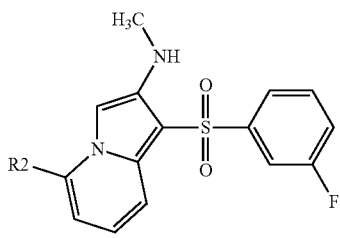

1.4.2(1-9)

1.4.2(1): R1 = H, R2 = CH$_3$,
1.4.2(2): R1 = 3-Cl, R2 = CH$_3$,
1.4.2(3): R1 = 3-F, R2 = CH$_3$,
1.4.2(4): R1 = H, R2 = piperazin-1-yl;
1.4.2(5): R1 = 3-Cl, R2 = piperazine-1-yl;
1.4.2(6): R1 = 3-F, R2 = piperazine-1-yl;
1.4.2(7): R1 = H, R2 = 4-methylpiperazine-1-yl;
1.4.2(8): R1 = 3-Cl, R2 = 4-methylpiperazine-1-yl;
1.4.2(9): R1 = 3-F, R2 = 4-methylpiperazine-1-yl;

The more preferable methyl-amines of the general formulas 1.5 are the compounds selected from the group consisting of methyl-(8-piperazin-1-yl-3-phenylsulfonylquinolin-4-yl)-amine 1.5(1), methyl-[8-piperazin-1-yl-3-(3-chlorophenylsulfonyl)quinolin-4-yl]-amine 1.5(2), methyl-[8-piperazin-1-yl-3-(3-fluorophenylsulfonyl)quinolin-4-yl]-amine 1.5(3), methyl-[8-(4-methylpiperazin-1-yl)-3-phenylsulfonylquinolin-4-yl]-amine 1.5(4), methyl-[8-(4-methylpiperazin-1-yl)-3-(3-chlorophenylsulfonyl)quinolin-4-yl]-amine 1.5(5), methyl-[8-(4-methylpiperazin-1-yl)-3-(3-fluorophenylsulfonyl)quinolin-4-yl]-amine 1.5(6),

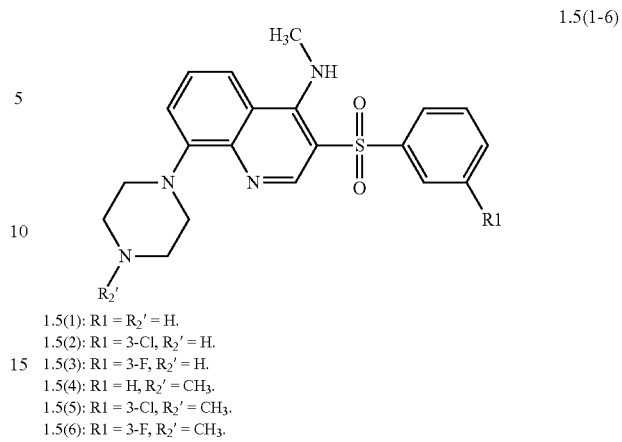

1.5(1-6)

1.5(1): R1 = R$_2$' = H.
1.5(2): R1 = 3-Cl, R$_2$' = H.
1.5(3): R1 = 3-F, R$_2$' = H.
1.5(4): R1 = H, R$_2$' = CH$_3$.
1.5(5): R1 = 3-Cl, R$_2$' = CH$_3$.
1.5(6): R1 = 3-F, R$_2$' = CH$_3$.

The more preferable methyl-amines of the general formulas 1.6 are the compounds selected from the group consisting of methyl-(8-piperazin-1-yl-5-phenylsulfonylquinolin-6-yl)-amine 1.6(1), methyl-[8-piperazin-1-yl-5-(3-chlorophenylsulfonyl)quinolin-6-yl]-amine 1.6(2), methyl-[8-piperazin-1-yl-5-(3-fluorophenylsulfonyl)quinolin-6-yl]-amine 1.6(3), methyl-[8-(4-methylpiperazin-1-yl)-5-phenylsulfonylquinolin-6-yl]-amine 1.6(4), methyl-[8-(4-methylpiperazin-1-yl)-5-(3-chlorophenylsulfonyl)quinolin-6-yl]-amine 1.6(5), methyl-[8-(4-methylpiperazin-1-yl)-5-(3-fluorophenylsulfonyl)quinolin-6-yl]-amine 1.6(6).

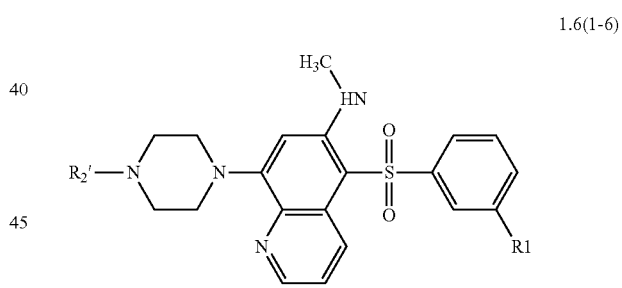

1.6(1-6)

1.6(1): R1 = R$_2$' = H.
1.6(2): R1 = 3-Cl, R$_2$' = H.
1.6(3): R1 = 3-F, R$_2$' = H.
1.6(4): R1 = H, R$_2$' = CH$_3$.
1.6(5): R1 = 3-Cl, R$_2$' = CH$_3$.
1.6(6): R1 = 3-F, R$_2$' = CH$_3$.

The more preferable methyl-amines of the general formulas 1.7 are the compounds selected from the group consisting of methyl-(8-piperazin-1-yl-4-phenylsulfonylquinolin-3-yl)-amine 1.7(1), methyl-[8-piperazin-1-yl-4-(3-chlorophenylsulfonyl)quinolin-3-yl]-amine 1.7(2), methyl-[8-piperazin-1-yl-4-(3-fluorophenylsulfonyl)quinolin-3-yl]-amine 1.7(3), methyl-[8-(4-methylpiperazin-1-yl)-4-phenylsulfonylquinolin-3-yl]-amine 1.7(4), methyl-[8-(4-methylpiperazin-1-yl)-4-(3-chlorophenylsulfonyl)quinolin-3-yl]-amine 1.7(5), methyl-[8-(4-methylpiperazin-1-yl)-4-(3-fluorophenylsulfonyl)quinolin-3-yl]-amine 1.7(6).

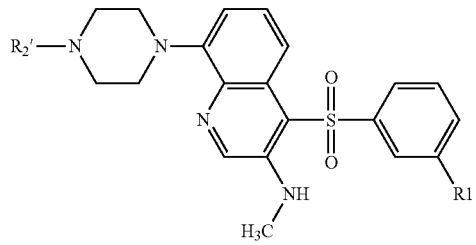

1.7(1): R1 = R2′ = H.
1.7(2): R1 = 3-Cl, R2′ = H.
1.7(3): R1 = 3-F, R2′ = H.
1.7(4): R1 = H, R2′ = CH3.
1.7(5): R1 = 3-Cl, R2′ = CH3.
1.7(6): R1 = 3-F, R2′ = CH3.

The more preferable methyl-amines of the general formulas 1.8 are the compounds selected from the group consisting of
methyl-[2-methyl-4-(3-chlorophenylsulfonyl)oxazol-5-yl]-amine 1.8(2),
methyl-[2-methyl-4-(3-fluorophenylsulfonyl)oxazol-5-yl]-amine 1.8(3),
methyl-(2-piperazin-1-yl-4-phenylsulfonyloxazol-5-yl)-amine 1.8(4),
methyl-[2-piperazin-1-yl-4-(3-chlorophenylsulfonyl)oxazol-5-yl]-amine 1.8(5),
methyl-[2-piperazin-1-yl-4-(3-fluorophenylsulfonyl)oxazol-5-yl]-amine 1.8(6),
methyl-[2-(4-methylpiperazin-1-yl)-4-phenylsulfonyloxazol-5-yl]-amine 1.8(7),
methyl-[2-(4-methylpiperazin-1-yl)-4-(3-chlorophenylsulfonyl)oxazol-5-yl]-amine 1.8(8),
methyl-[2-(4-methylpiperazin-1-yl)-4-(3-fluorophenylsulfonyl)oxazol-5-yl]-amine 1.8(9).

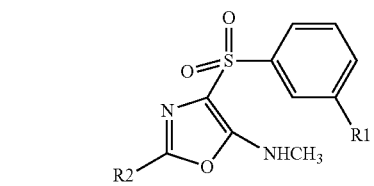

1.8.(2): R1 = 3-Cl, R2 = CH3,
1.8.(3): R1 = 3-F, R2 = CH3,
1.8.(4): R1 = H, R2 = piperazin-1-yl;
1.8.(5): R1 = 3-Cl, R2 = piperazine-1-yl;
1.8.(6): R1 = 3-F, R2 = piperazine-1-yl;
1.8.(7): R1 = H, R2 = 4-methylpiperazine-1-yl;
1.8.(8): R1 = 3-Cl, R2 = 4-methylpiperazine-1-yl;
1.8.(9): R1 = 3-F, R2 = 4-methylpiperazine-1-yl.

Substituted methyl-amines of the general formula 1 were prepared using well-known reactions. If as a result of the reaction one product was formed predominantly, it was isolated from the reaction mixture and subjected to purification by known methods, for example, recrystallization or chromatography. If there was a mixture of two compounds it was separated, for example, by means of preparative chromatography.

Methyl-(3-piperazin-1-yl-6-phenylsulfonylphenyl)-amine 1.1(2) was prepared starting from 2-nitro-1,4-difluorobenzene 2(1) according to the scheme 1 given below.

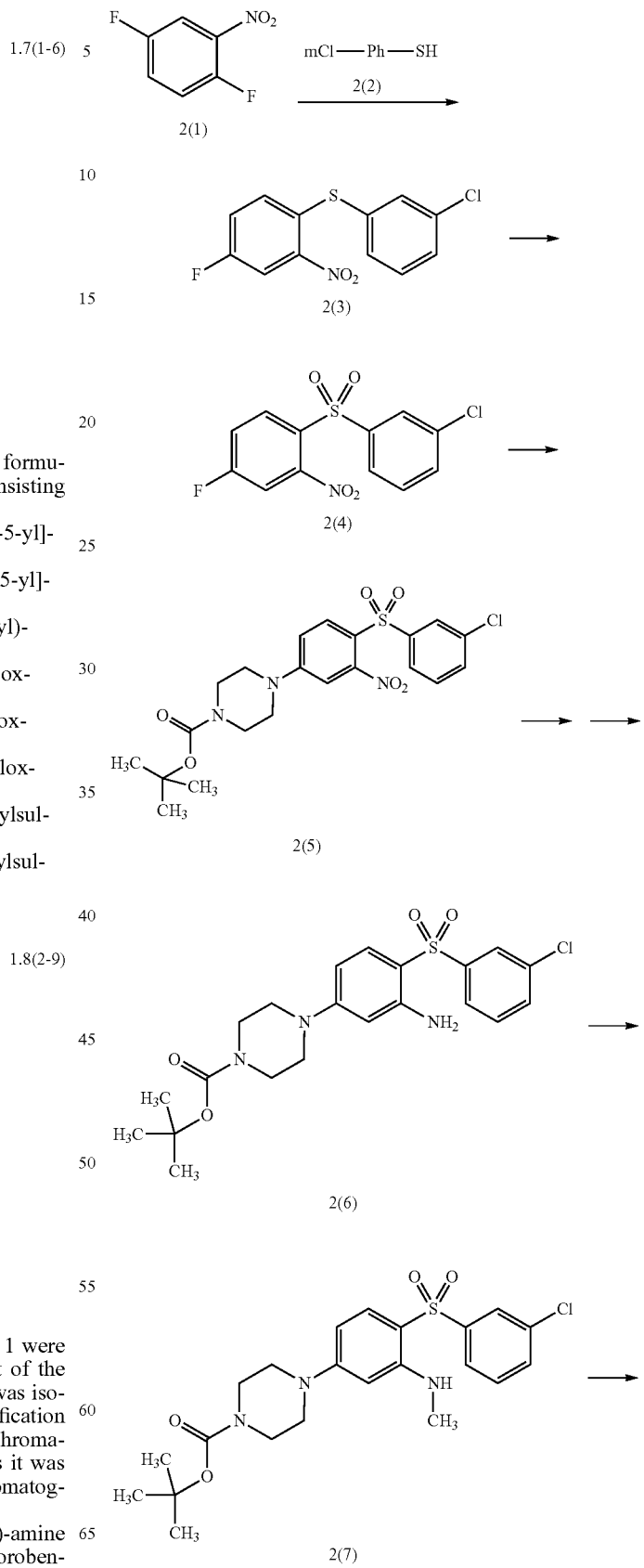

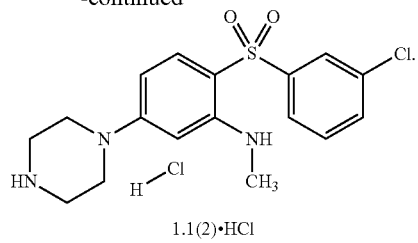

1.1(2)·HCl

Compound 1.1(5) was prepared according to analogous scheme using N-methylpiperazine instead of piperazine.

Compounds 1.1(7)-1.1(12) were synthesized according to analogous scheme using 2,4-difluoronitrobenzene as a starting material.

Methyl-(4-phenylsulfonyl-biphenyl-3-yl)-amine 1.1(13) was prepared starting from 2-nitro-4-iodo-chlorobenzene 4(1) according to scheme 2 given below.

Scheme 2

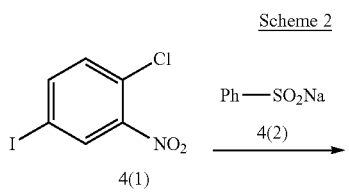
4(1)

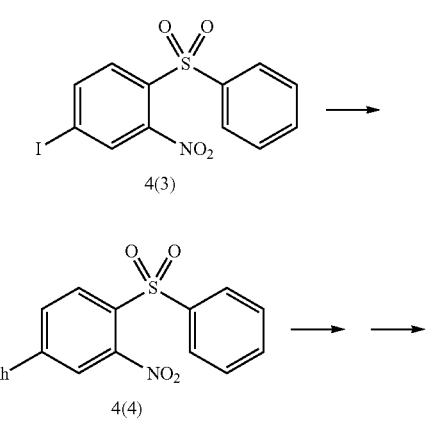

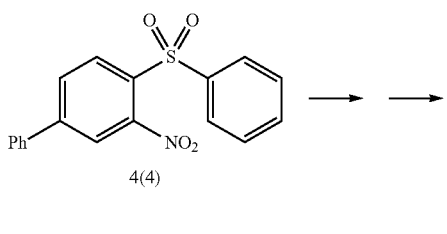

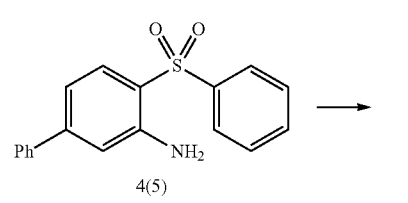

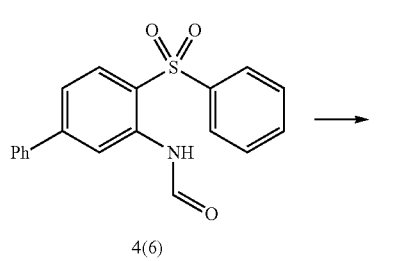
4(6)

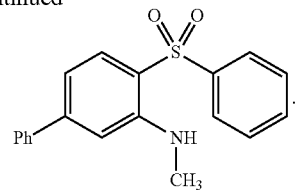
1.1(13)

Methyl-(5-pyridin-3-yl-2-phenylsulfonylphenyl)-amine 1.1(14) was prepared starting from 3-nitro-4-phenylsulfonyl-iodobebzene 4(3) according to scheme 3 given below.

Scheme 3.

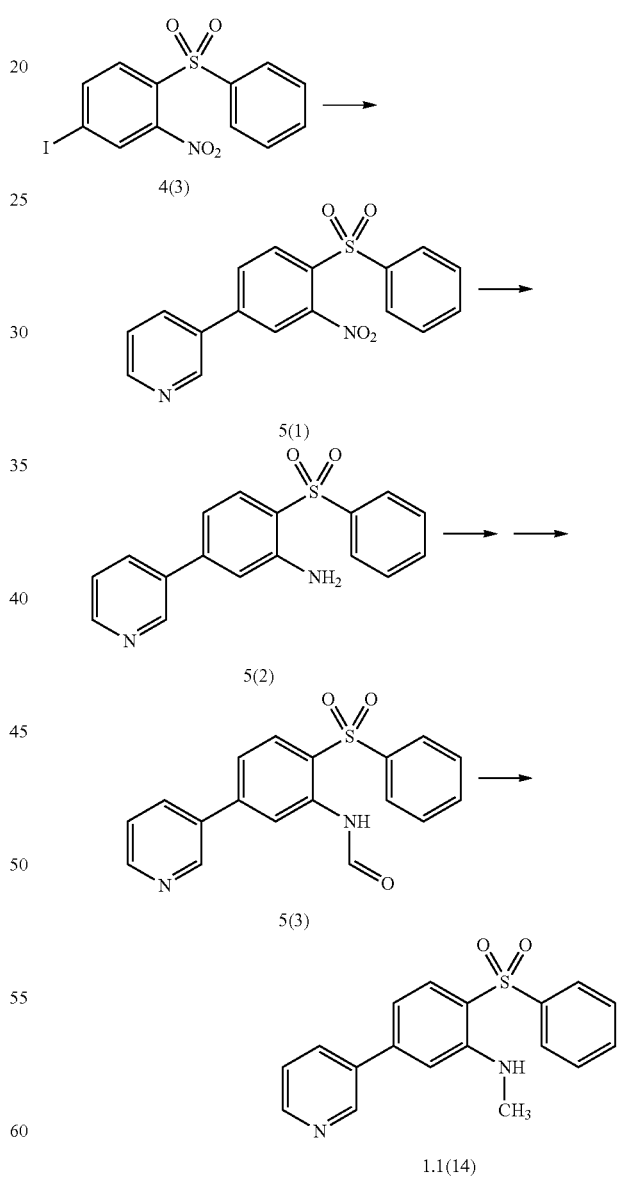

Methyl-(4-piperazin-1-yl-2-phenylsulfonylnaphthalen-1-yl)-amine 1.2.1(1) and its analogues 1.2.1(2)-1.2.1(3) were prepared starting from 2,4-dichloronaphthalene-1-amine according to scheme 4 given below:

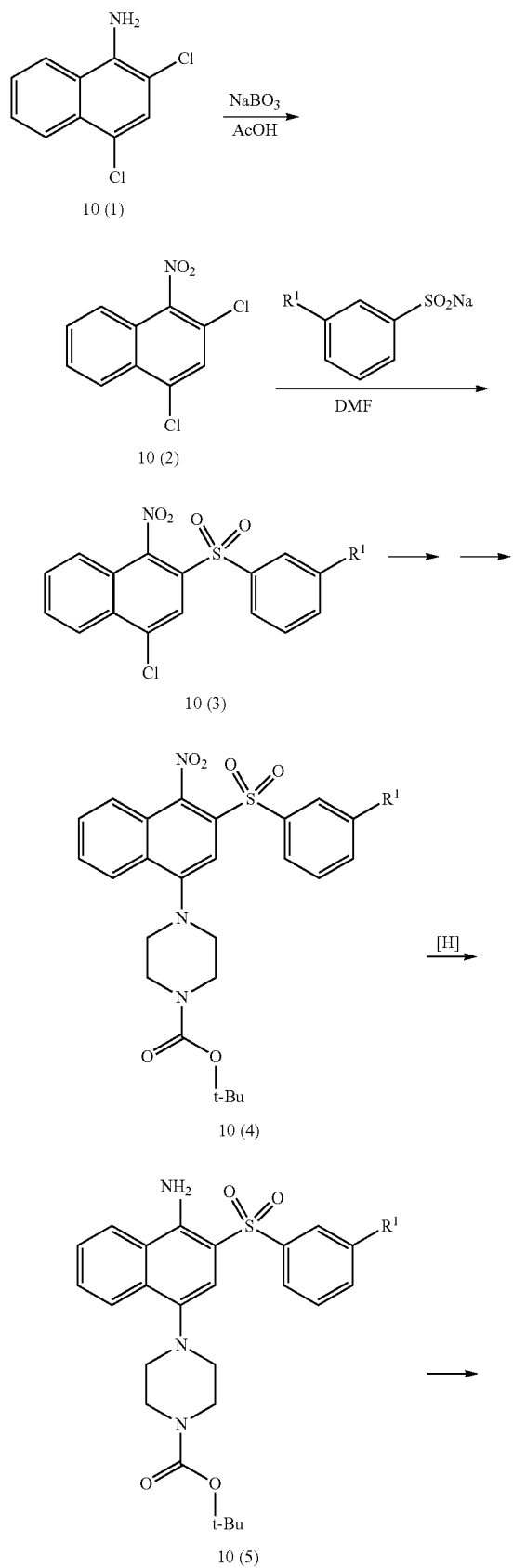
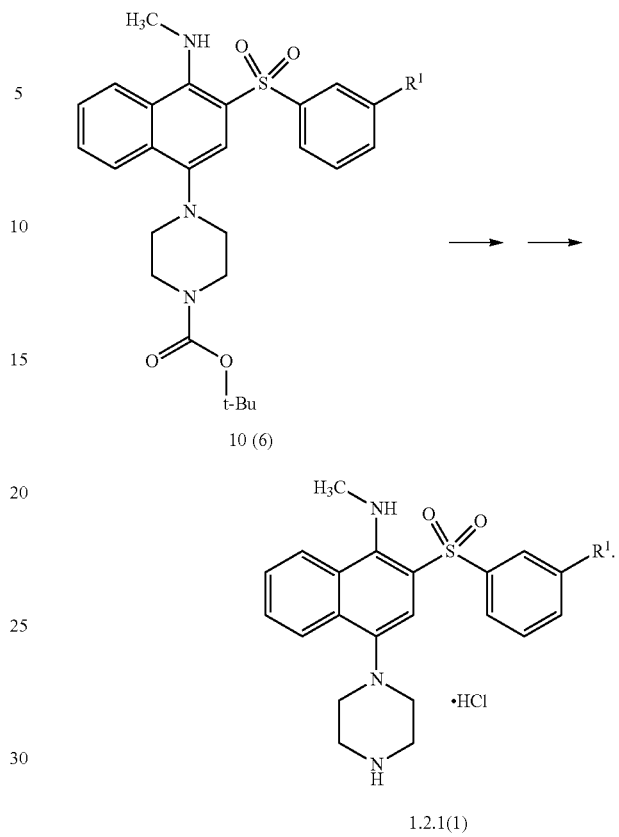
where R1 represents H, F, Cl.
Compounds 1.2.1(4)-1.2.1(6) were prepared according to the same scheme using N-methylpiperazine instead of piperazin.
Methyl-(5-piperazin-1-yl-2-phenylsulfanylnaphthalen-1-yl)-amine 1.2.2(1) and its analogues 1.2.2(2)-1.2.2(6) were prepared starting from N-(2-bromo-5-nitronaphthalen-1-yl) acetamide according to scheme 5 shown below:
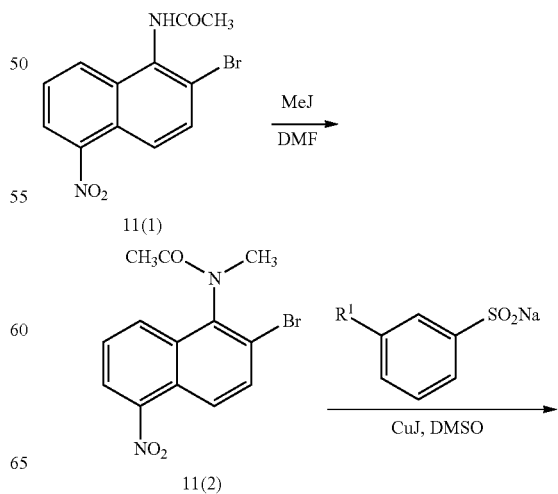

-continued
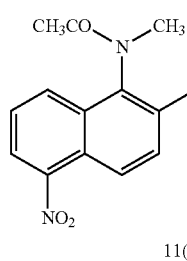
11(3)
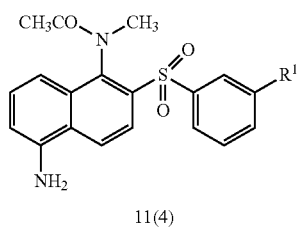
11(4)
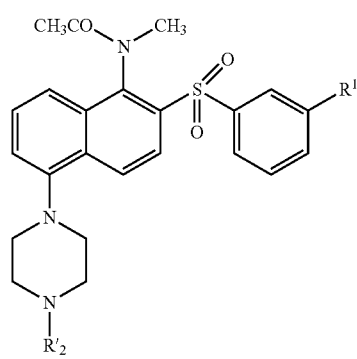
11(5)
R'$_2$ = H, Me
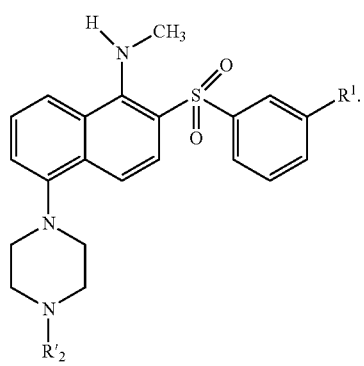
1.2.2(1)
R'$_2$ = H, Me
wherein R1 has the above meanings.
Compounds of the general formulas 1.3-1.3(1)-1.3(6) were prepared starting from 1,4-dichloro-2-nitronaphthalene according to scheme 6 given below:
Scheme 6
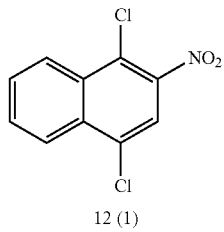 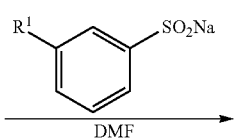
12 (1)
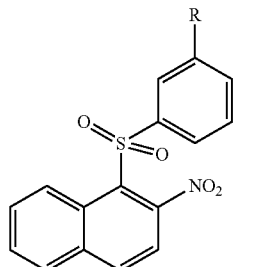 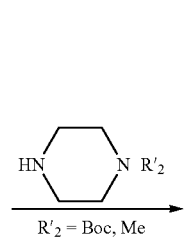
12 (2)
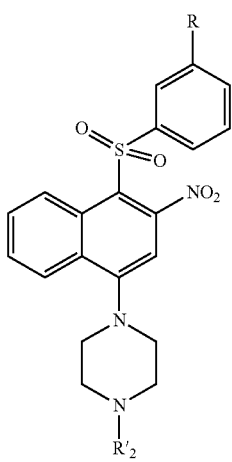 
12 (3)
R'$_2$ = Boc, Me
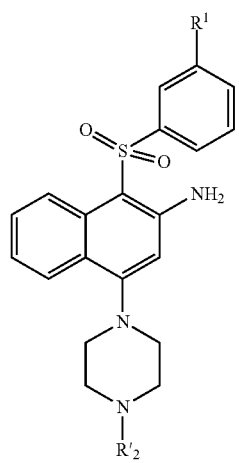 
12 (4)
R'$_2$ = Boc, Me

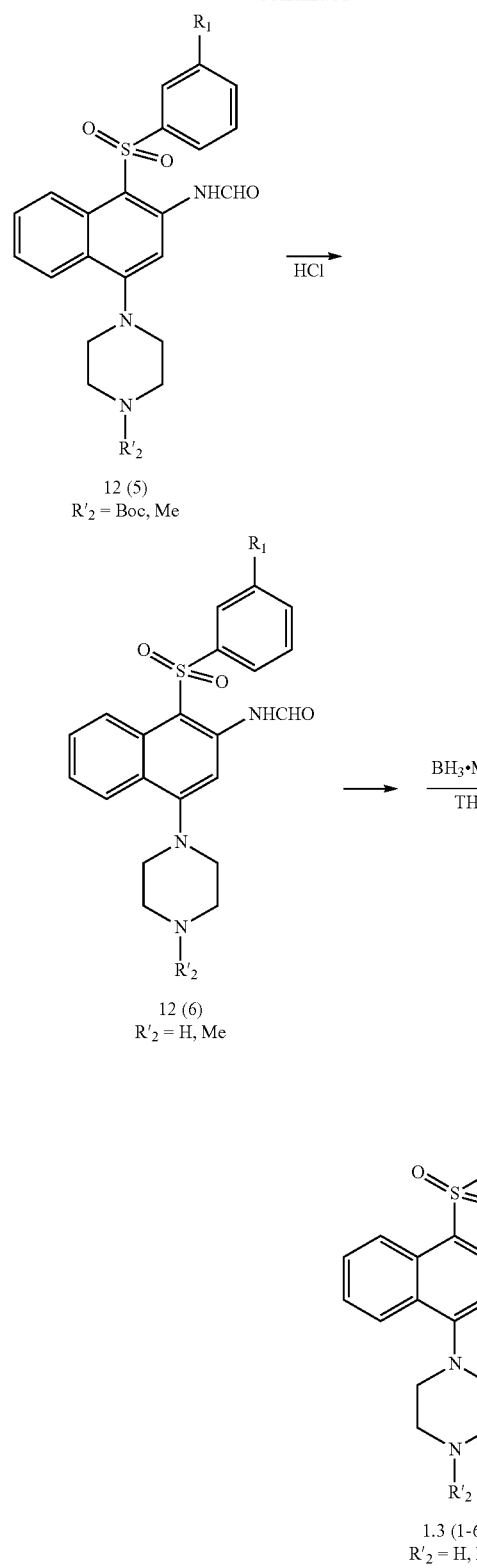
12 (5)
R'₂ = Boc, Me
12 (6)
R'₂ = H, Me
1.3 (1-6)
R'₂ = H, Me
wherein R1 has the above meanings.
Methyl-(1-phenylsulfonylindolizin-2-yl)-amine 1.4.1(1) was prepared starting from 2-(chloromethyl)pyridine 6(1) according to scheme 7 given below.
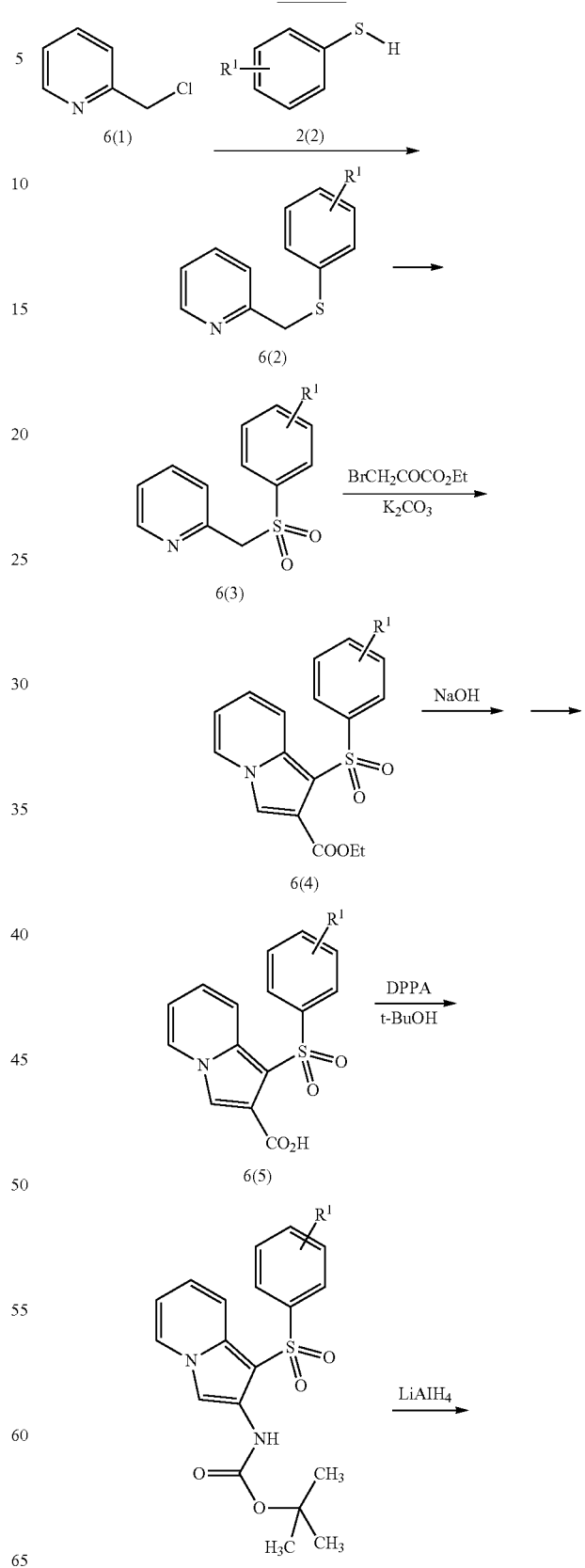
Scheme 7

25

-continued

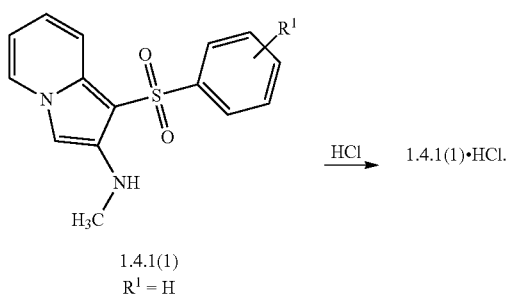

1.4.1(1)
R¹ = H

HCl → 1.4.1(1)·HCl.

wherein R¹ has the above meanings.

Compounds 1.4.1(2) and 1.4.1(3) were prepared according to analogous scheme using appropriately substituted thiophenols.

Methyl-(3-methyl-1-phenylsulfonylindolizin-2-yl)-amine 1.4.1(4) was prepared starting from compound 6(6) according to scheme 8 given below.

Scheme 8

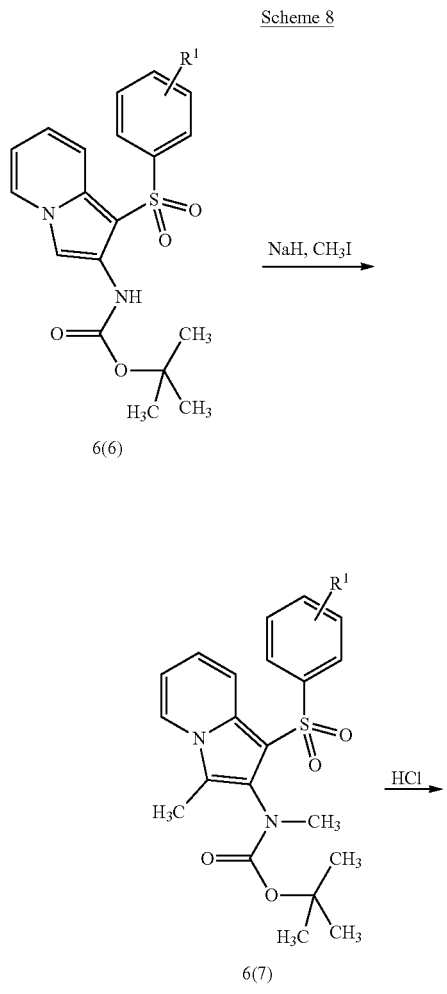

26

-continued

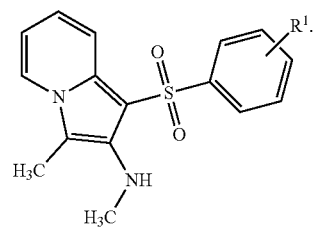

1.4.1(4)
R¹ = H wherein R¹ has the above meanings.

In analogous manner, compounds 1.4.1(5) and 1.4.1(6) were prepared starting from 3-chloro and 3-fluoro-thiophenols.

Compounds 1.4.1(7)-1.4.1(9) were prepared starting from ethyl 1-(phenylsulfonyl)indolizin-2-carboxylate according to scheme 9.

Scheme 9

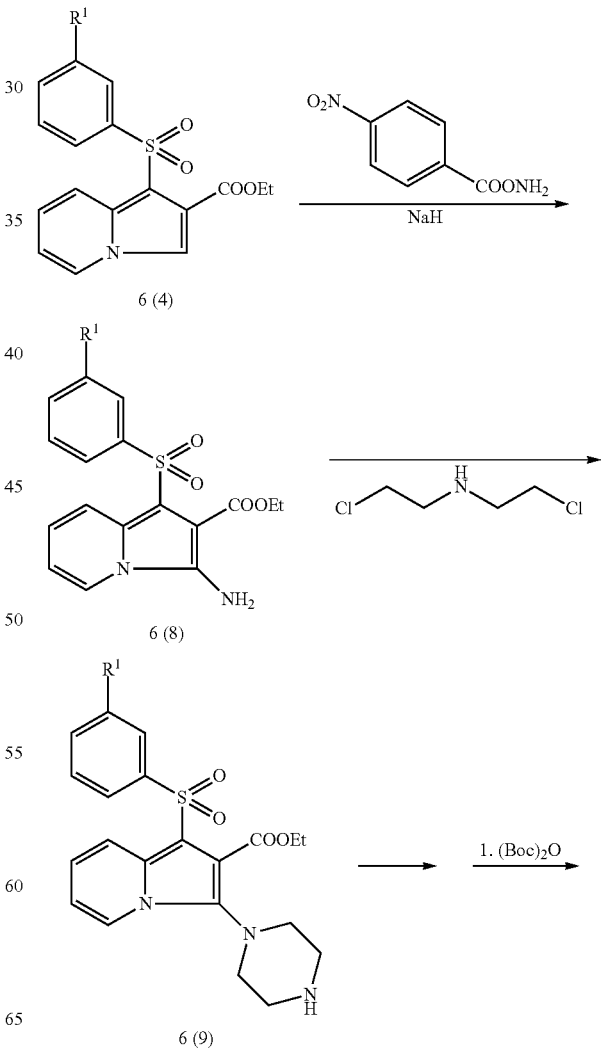

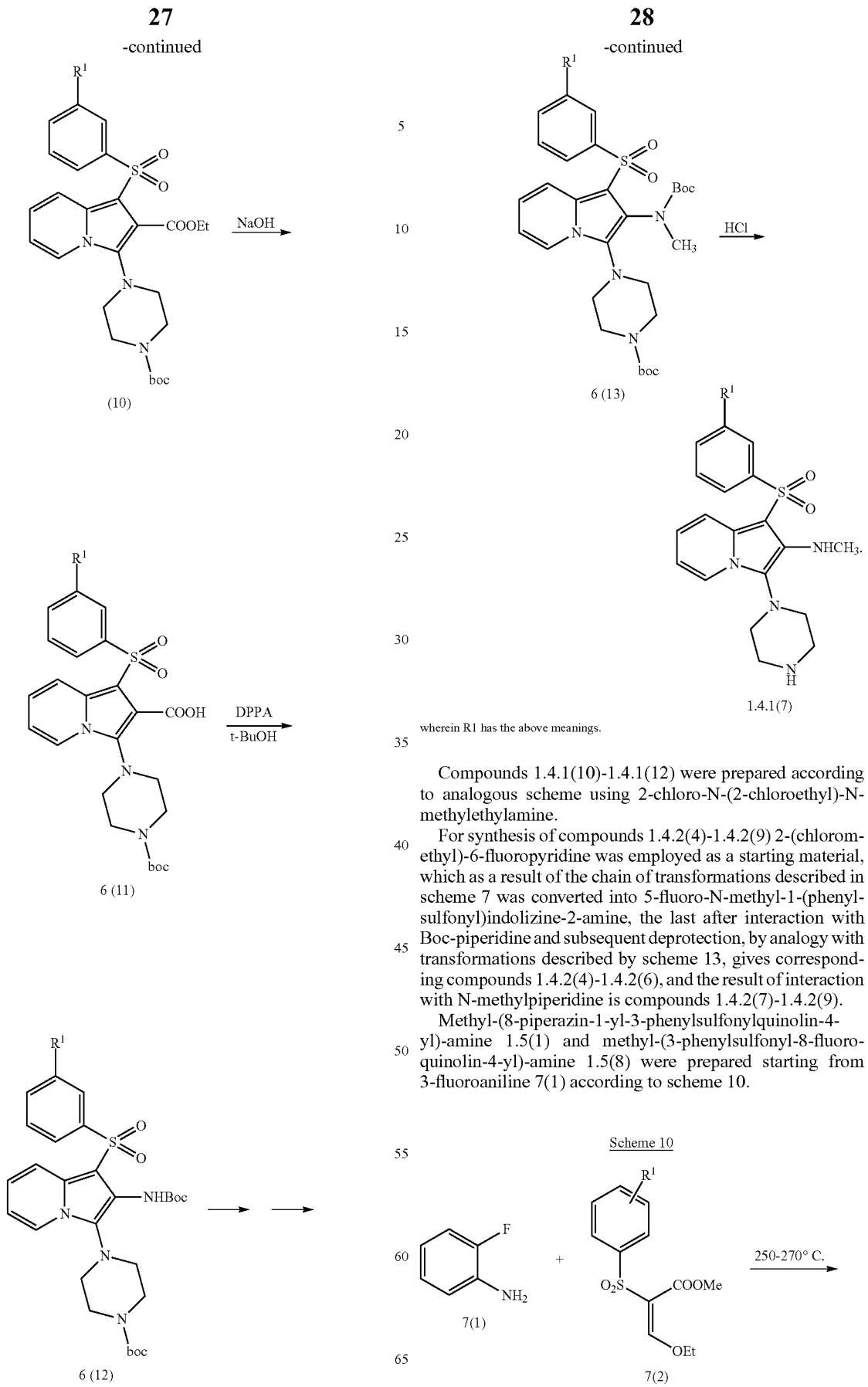

wherein R1 has the above meanings.

Compounds 1.4.1(10)-1.4.1(12) were prepared according to analogous scheme using 2-chloro-N-(2-chloroethyl)-N-methylethylamine.

For synthesis of compounds 1.4.2(4)-1.4.2(9) 2-(chloromethyl)-6-fluoropyridine was employed as a starting material, which as a result of the chain of transformations described in scheme 7 was converted into 5-fluoro-N-methyl-1-(phenylsulfonyl)indolizine-2-amine, the last after interaction with Boc-piperidine and subsequent deprotection, by analogy with transformations described by scheme 13, gives corresponding compounds 1.4.2(4)-1.4.2(6), and the result of interaction with N-methylpiperidine is compounds 1.4.2(7)-1.4.2(9).

Methyl-(8-piperazin-1-yl-3-phenylsulfonylquinolin-4-yl)-amine 1.5(1) and methyl-(3-phenylsulfonyl-8-fluoroquinolin-4-yl)-amine 1.5(8) were prepared starting from 3-fluoroaniline 7(1) according to scheme 10.

29
-continued
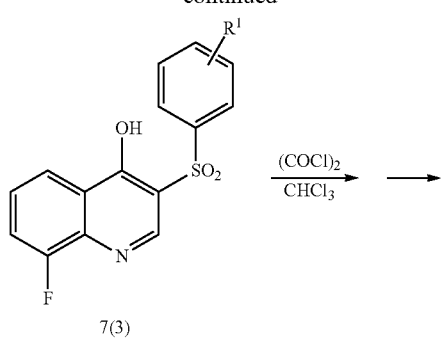
7(3)
↓ (COCl)₂ / CHCl₃
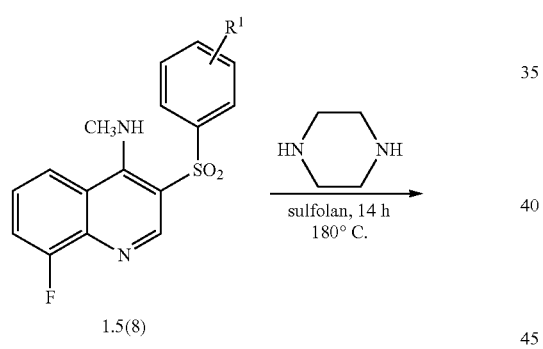
7(4)
↓ NH₂CH₃ / TGF, 12 h, r.t.
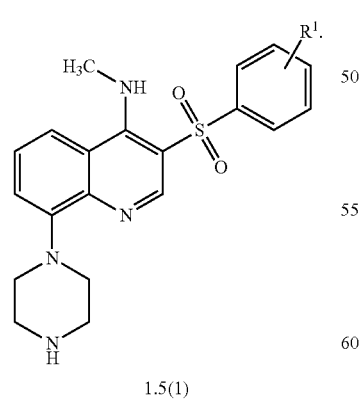
1.5(8)
↓ HN⌐NH piperazine / sulfolan, 14 h, 180° C.
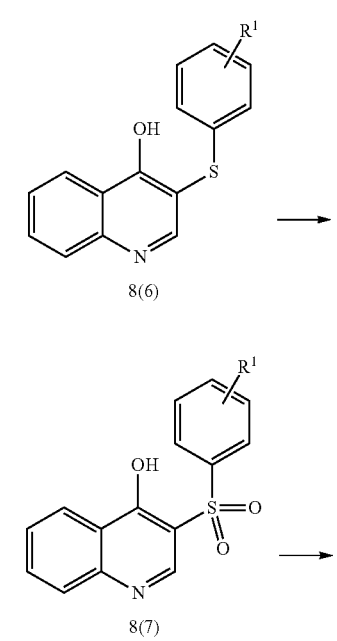
1.5(1)
Methyl-(3-phenylsulfonylquinolin-4-yl)-amine 1.5(7) was prepared starting from aniline 8(1) according to scheme 11 given below.
30
Scheme 11.
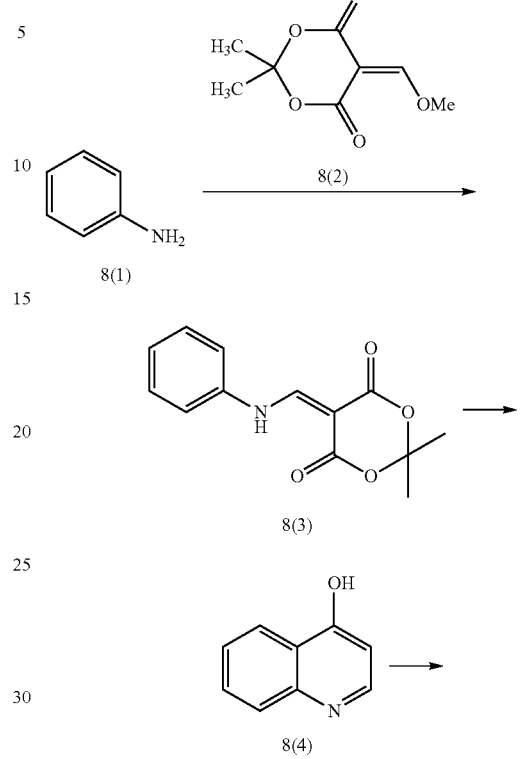

-continued
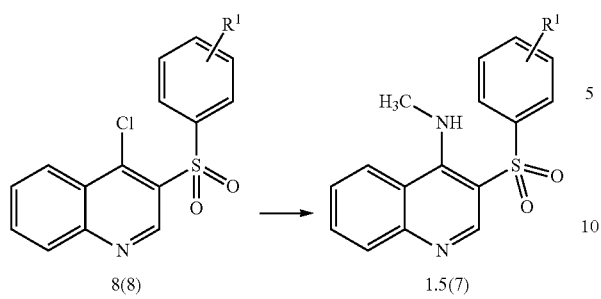
wherein R1 has the above meanings.
Compounds of the general formula 1.6-1.6(1)-1.6(6) were synthesized starting from 5,8-dichloro-6-nitroquinoline according to scheme 12.
-continued
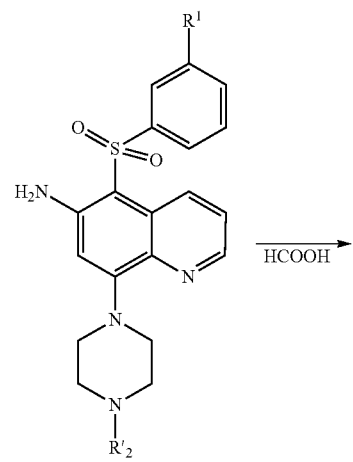
$R'_2$ = Boc, Me
13 (4)
Scheme 12
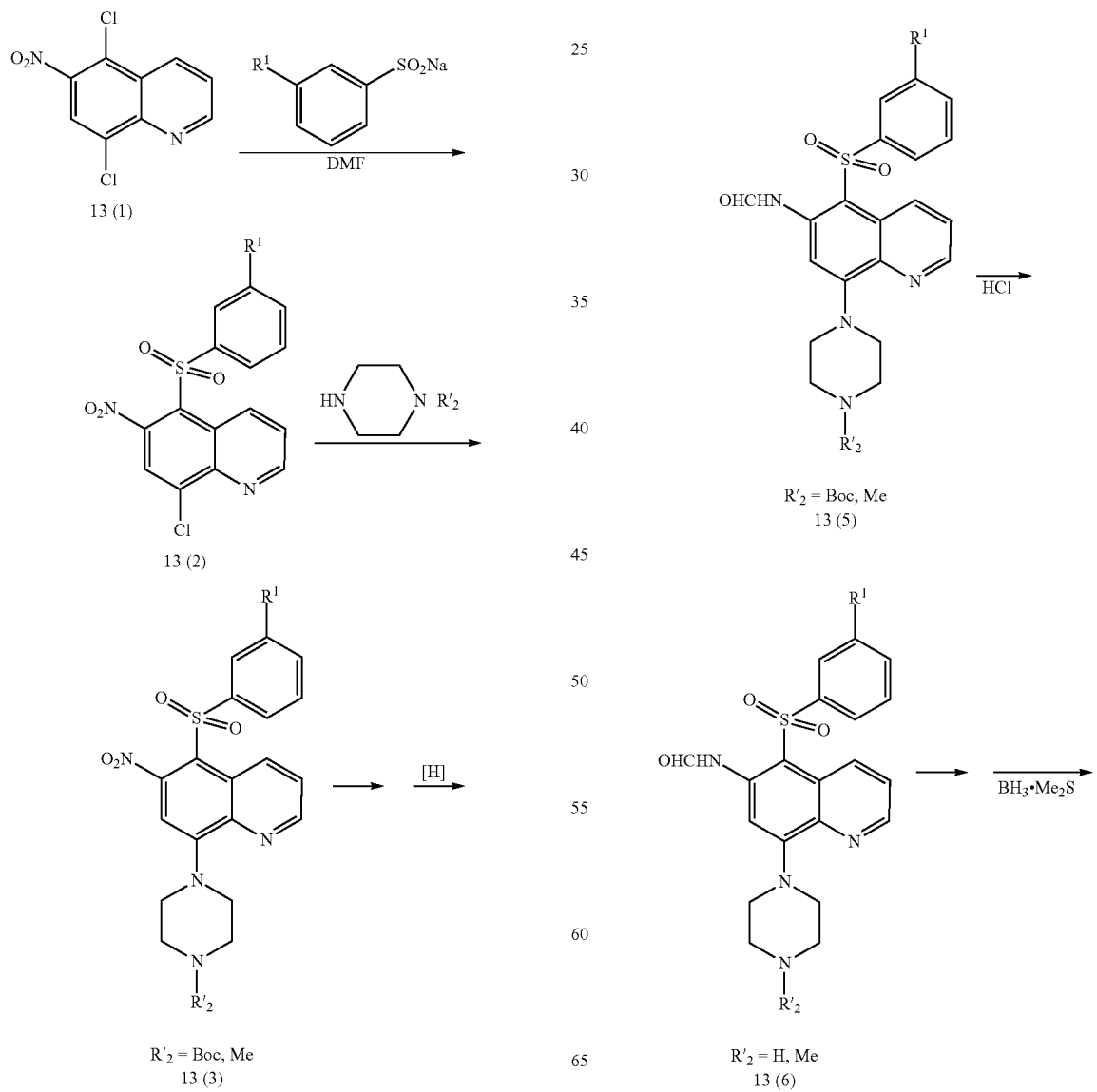

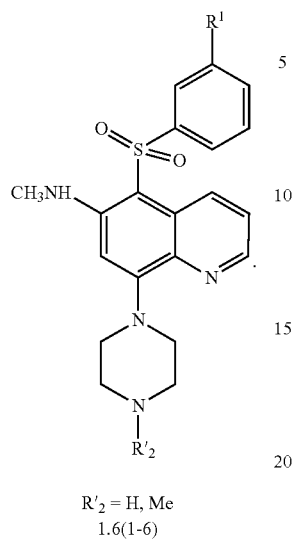
R'$_2$ = H, Me
1.6(1-6)
wherein R1 has the above meanings.
Compounds of the general formulas 1.7-1.7(1)-1.7(6) were synthesized starting from 4-chloro-8-fluoro-3-nitroquinoline according to scheme 13.
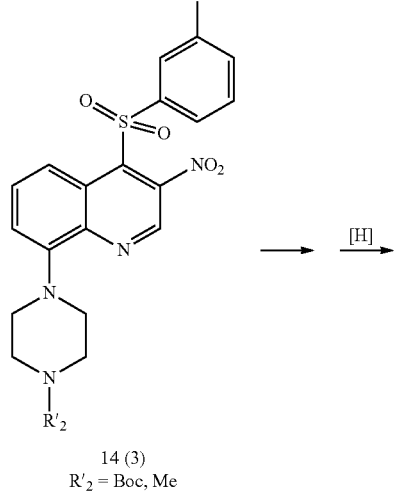
14 (3)
R'$_2$ = Boc, Me
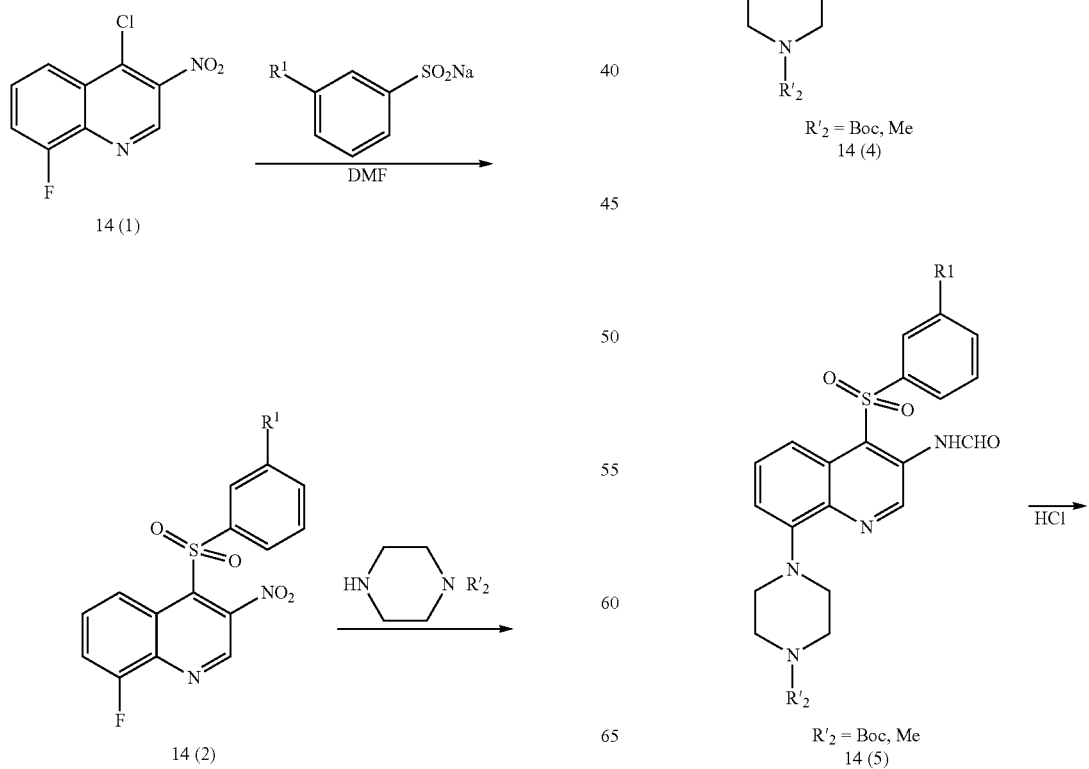

-continued

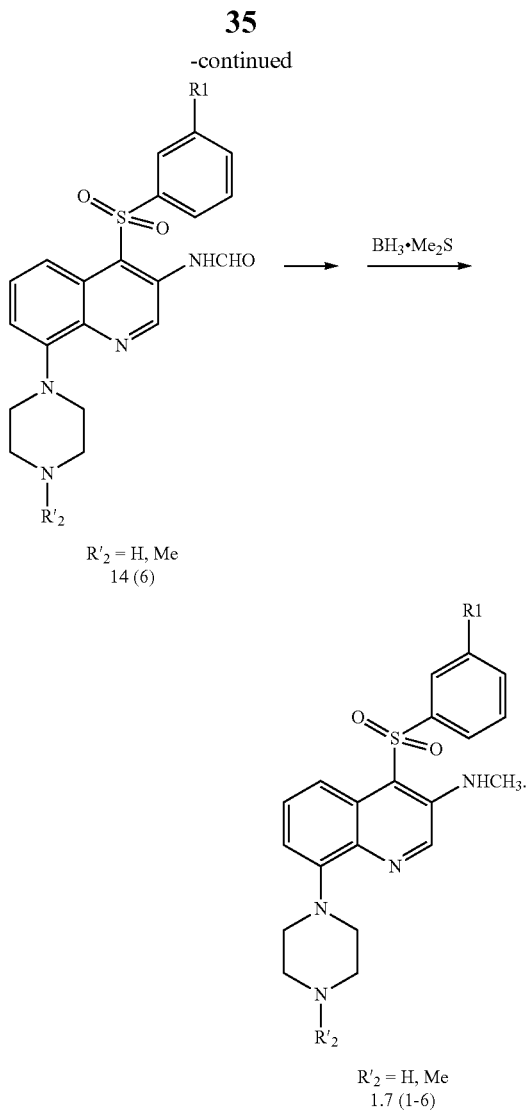

R'₂ = H, Me
14 (6)

wherein R1 has the above meanings.

Substituted methyl-(5-phenylsulfonyloxazol-4-yl)-amines 1.8 were prepared starting from amides 9(1) according to scheme 14.

Scheme 14

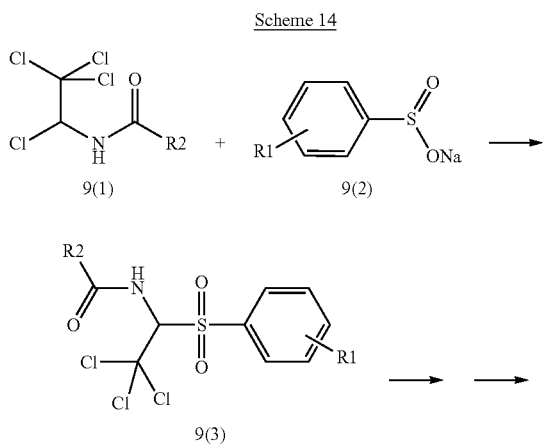

-continued

9(4)

1.8 wherein R2 represents methyl, 4-acetylpiperazin-1-yl.

The subject of the present invention is serotonin 5-HT$_6$ receptor antagonists representing substituted methyl-amines of the general formula 1, conceivably also in crystalline form or in the form of pharmaceutically acceptable salts.

The subject of the present invention is an active component for pharmaceutical compositions and medicaments representing at least one substituted methyl-amine of the general formula 1, conceivably in crystalline form or in the form of pharmaceutically acceptable salts exhibiting properties of serotonin 5-HT$_6$ receptor antagonist.

The subject of the present invention is also a pharmaceutical composition for prophylaxis and treatment of CNS diseases pathogenesis of which is associated with 5-HT$_6$ receptors including cognitive disorders and neurodegenerative diseases comprising an active component representing at least one substituted methyl-amine of the general formula 1, conceivably in crystalline form or in the form of pharmaceutically acceptable salts in pharmaceutically effective amount.

The more preferable is pharmaceutical composition mentioned above in the form of tablets, capsules, or injections, placed in pharmaceutically acceptable package.

The more preferable is also mentioned above pharmaceutical composition for prophylaxis and treatment of psychic disorders, schizophrenia, anxiety disorders, enhancement of mental capacities, and also for prophylaxis and treatment of obesity. The pharmaceutical composition may include pharmaceutically acceptable excipients. Pharmaceutically acceptable excipients mean diluents, auxiliary agents and/or carriers applied in the sphere of pharmaceutics. According to the invention pharmaceutical composition together with an active component of the general formula 1 may include other active ingredients provided that they do not give rise to undesirable effects, such as allergic reactions.

If needed, according to the present invention pharmaceutical compositions could be used in clinical practice in various forms prepared by mixing the said compositions with traditional pharmaceutical carries, for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

According to the present invention the carriers used in pharmaceutical compositions represent carriers which are used in the sphere of pharmaceutics for preparation of commonly used forms. Binding agents, greasing agents, disintegrators, solvents, diluents, stabilizers, suspending agents, colorless agents, taste flavors are used for peroral forms;

antiseptic agents, solubilizers, stabilizers are used in forms for injections; base materials, diluents, greasing agents, antiseptic agents are used in local forms.

The subject of the present invention is also a method for prophylaxis and treatment of CNS diseases pathogenesis of which is associated with 5-HT$_6$ receptors consisting in administration of active component or pharmaceutical composition mentioned above.

The pharmaceutical composition or active component could be introduced perorally or parenterally, for example, intravenous, subcutaneous, intraperitoneally or locally. Clinical dose of active component or pharmaceutical composition may be corrected depending on: therapeutic efficiency and bio-accessibility of active ingredients in patients' organism, rate of their exchange and removal from organism, and age, gender, and severity of patient's symptoms. Thus, the daily intake for adults normally being 10~500 mg, preferably 50~300 mg. Accordingly the above effective doses are to be taken into consideration while preparing pharmaceutical compositions of the present invention, each dose unit should contain 10~500 mg of an active component of the general formula 1, preferably 50~300 mg. Following the instructions of physician or pharmacist, these preparations could be taken several times over specified periods of time (preferably, from one to six times).

The subject of the present invention is also "molecular tools" for investigation of peculiarities of physiologically active compounds exhibiting the property to inhibit serotonin 5-HT$_6$ receptors, representing substituted methyl-amines of the general formula 1, conceivably also in crystalline form or in the form of pharmaceutically acceptable salts.

BEST EMBODIMENT OF THE INVENTION

The invention is illustrated by the following figures:

FIG. 1. Enhancement of memory disturbed by Scopolamine in male mice of BALB/c line under the influence of compounds 1.1(9), 1.5 (1) and 1.8(7) and reference substances (Tacrine and Memantine) in the test "Passive Avoidance of mice in the Shuttle Chamber". Latent period of the first entry into dark chamber.

Figure 2:
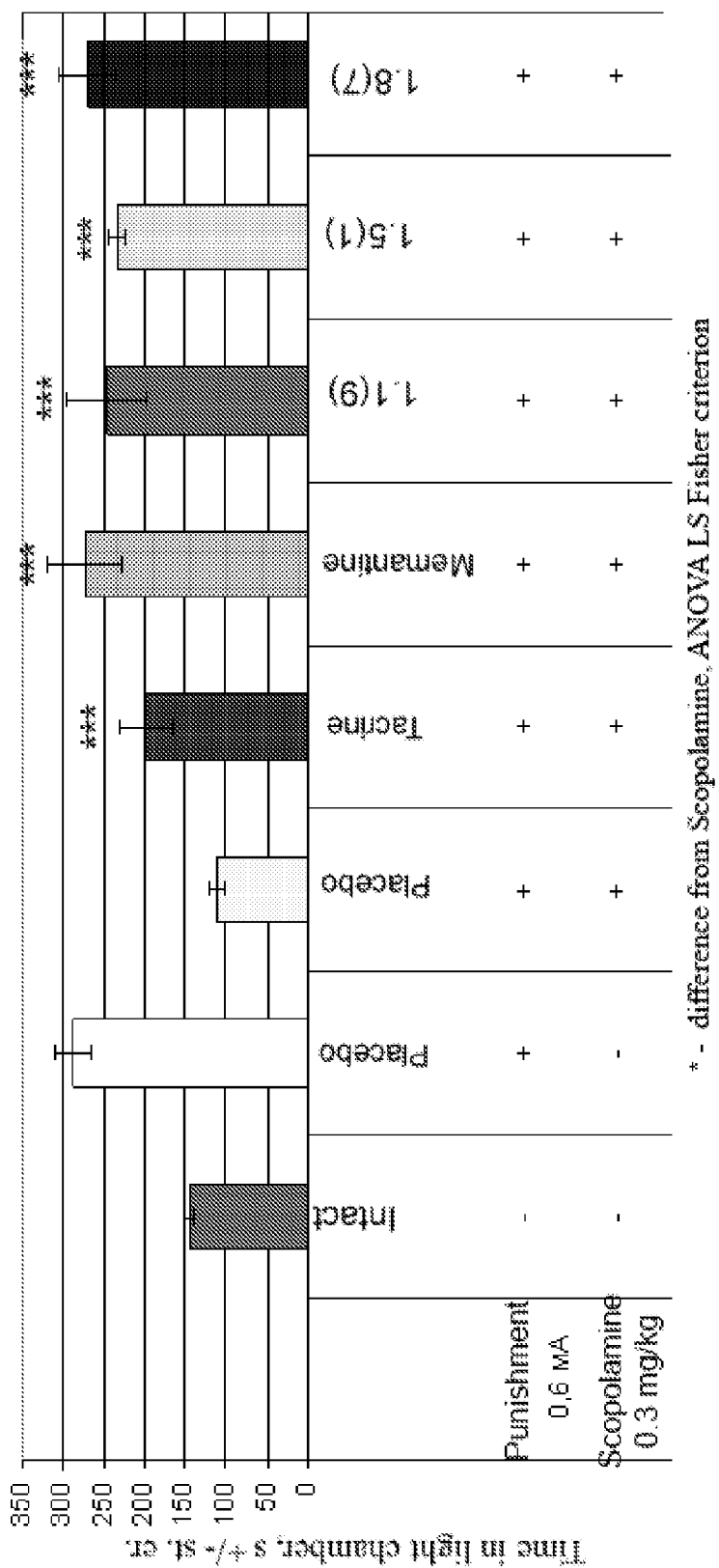

FIG. 2. Enhancement of memory disturbed by Scopolamine in male mice of BALB/c line, under the influence of 1.1(9), 1.5 (1) and 1.8(7) and reference substances (Tacrine and Memantine) in the test "Passive Avoidance of mice in the Shuttle Chamber". The time spent by the animals in the light chamber.

Figure 3:
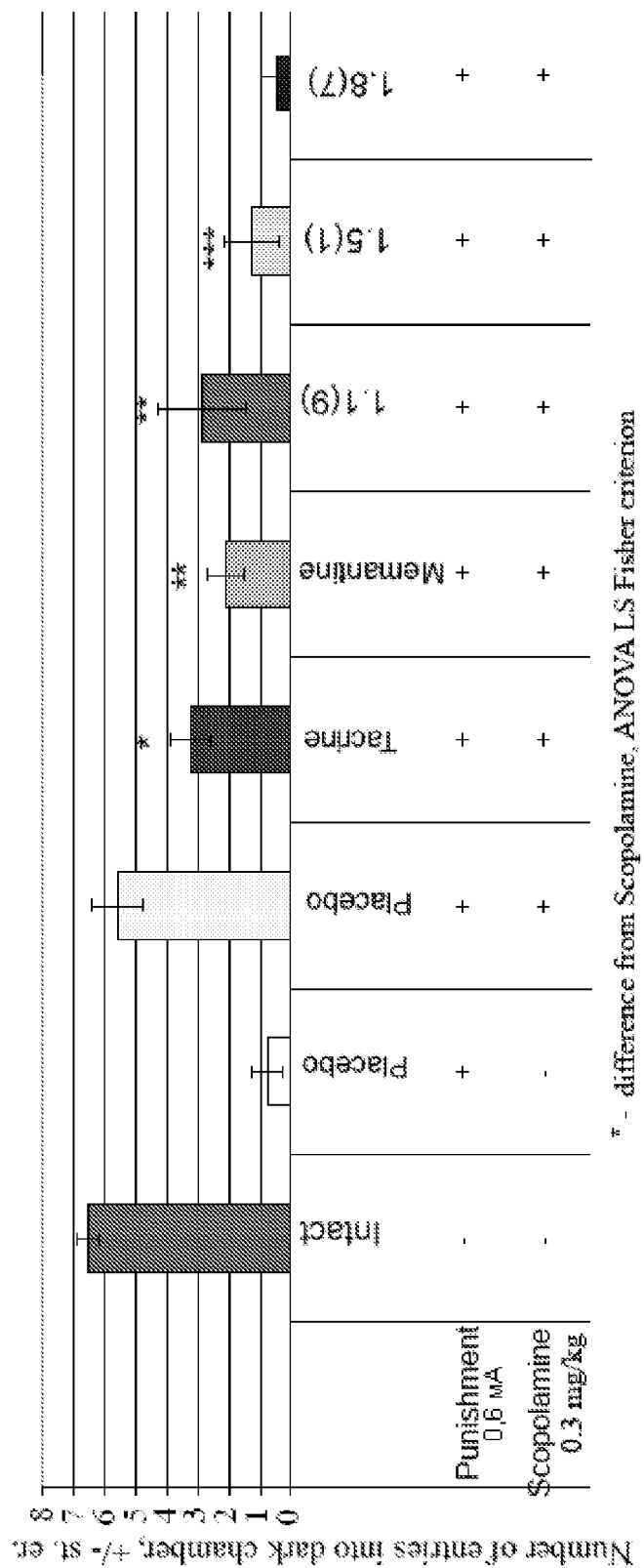

FIG. 3. Enhancement of memory disturbed by Scopolamine in male mice of BALB/c line, under the influence of compounds 1.1(9), 1.5 (1) and 1.8(7) and reference substances (Tacrine and Memantine) in the test "Passive Avoidance of mice in the Shuttle Chamber". The number of dark chamber entries.

Figure 4:
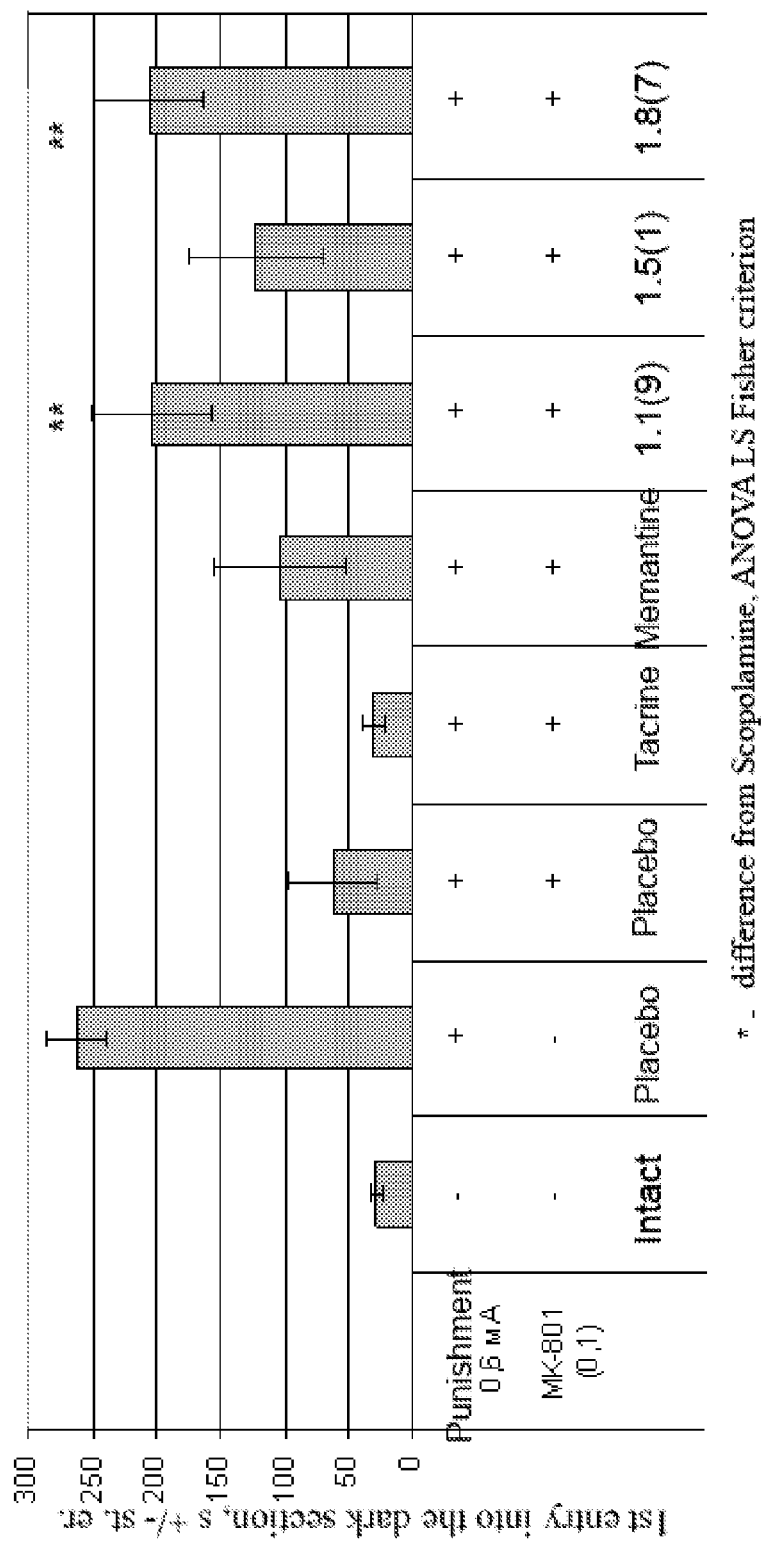

FIG. 4. Enhancement of memory disturbed by MK-801 in male mice of BALB/c line, under the influence of compounds 1.1(9), 1.5 (1) and 1.8(7) and reference substances (Tacrine and Memantine) in the test "Passive Avoidance of mice in the Shuttle Chamber". Latent period of the first entry into the dark chamber.

Figure 5:
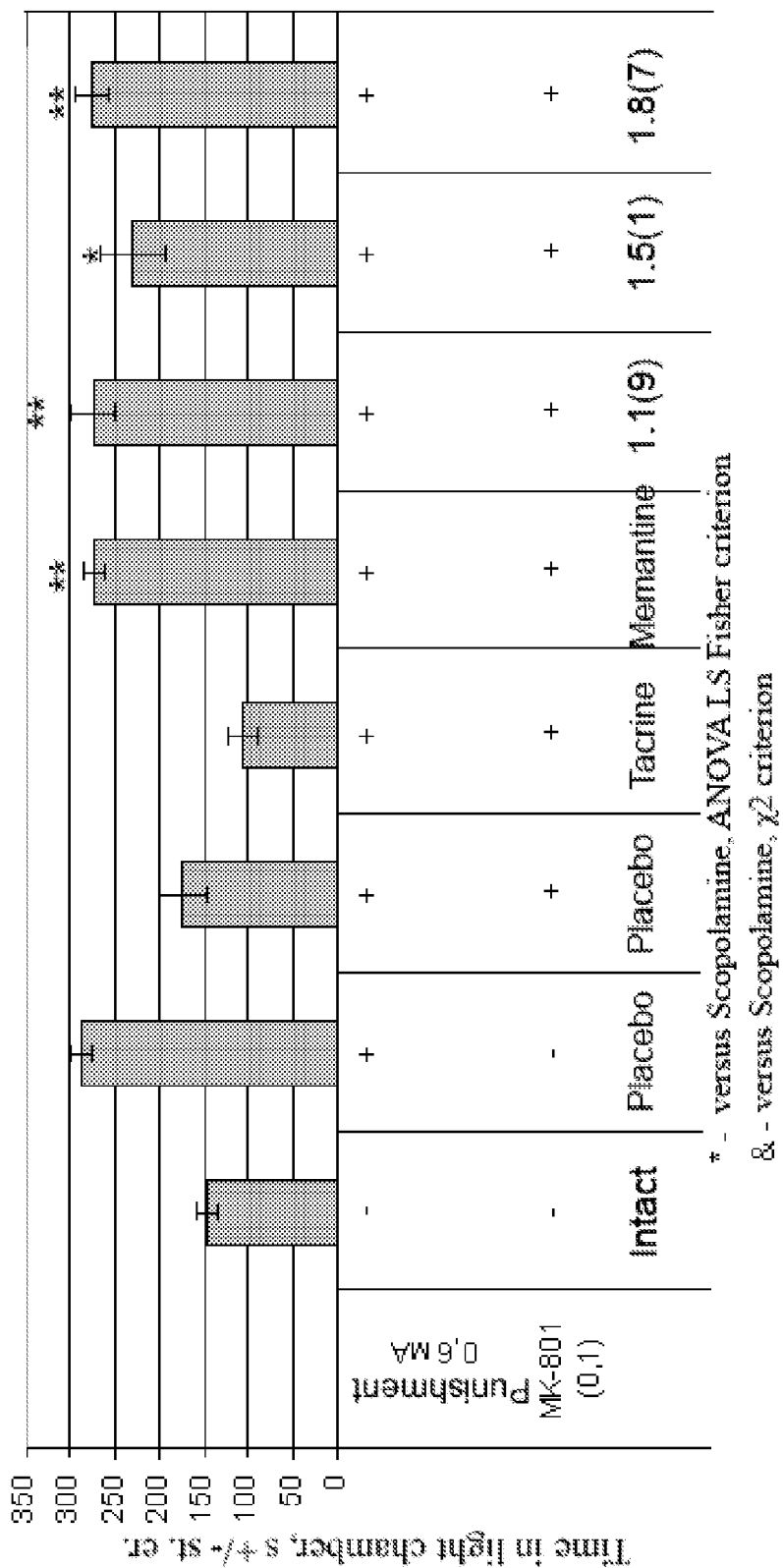

FIG. 5. Enhancement of memory disturbed by MK-801 in male mice of BALB/c line, under the influence of compounds 1.1(9), 1.5 (1) and 1.8(7) and reference substances (Tacrine and Memantine) in the test "Passive Avoidance of mice in the Shuttle Chamber". The time spent by the animals in the light chamber.

Figure 6:
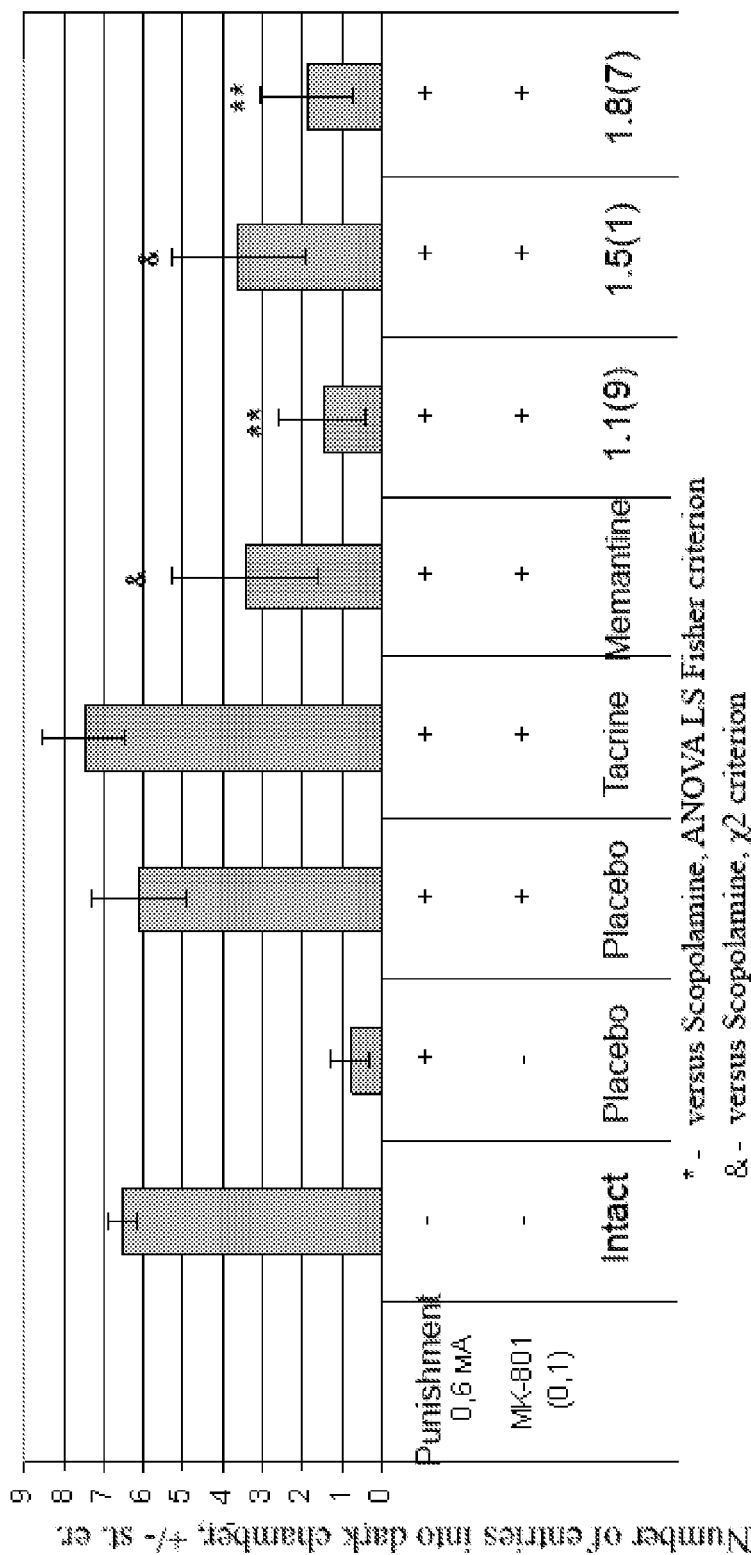

FIG. 6. Enhancement of memory disturbed by MK-801 in male mice of BALB/c line, under the influence of compounds 1.1(9), 1.5 (1) and 1.8(7) and reference substances (Tacrine and Memantine) in the test "Passive Avoidance of mice in the Shuttle Chamber". The number of dark chamber entries.

Figure 7:
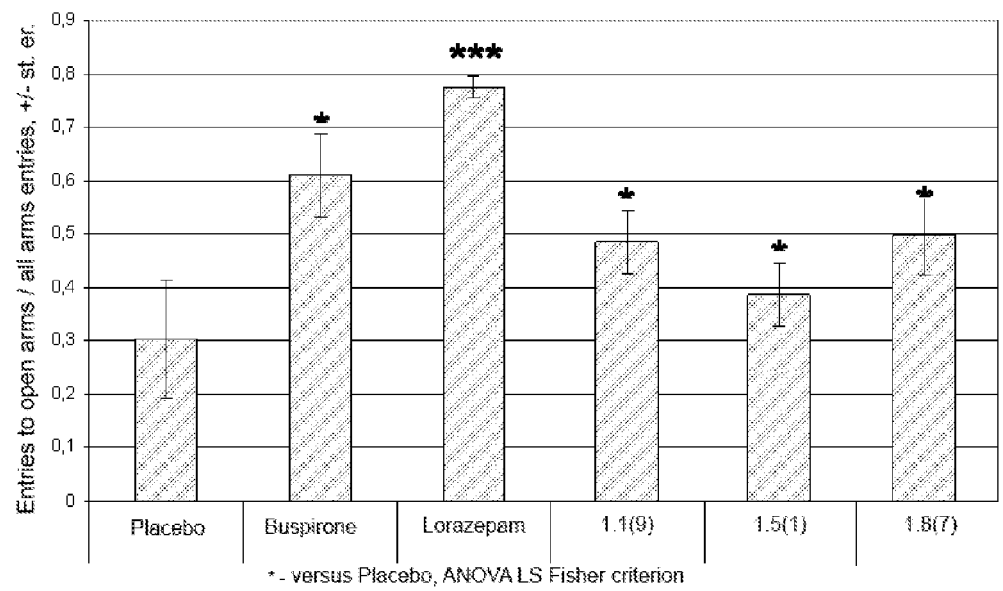

FIG. 7. Behavior of male mice of BALB/c line under the influence of compounds 1.1(9), 1.5 (1) and 1.8(7) and reference substances (Buspirone and Lorazepam) in the test "Mice Behavior in the Elevated Plus Maze". Ratio of open arm entries towards the overall number of entries to any arms.

Figure 8:
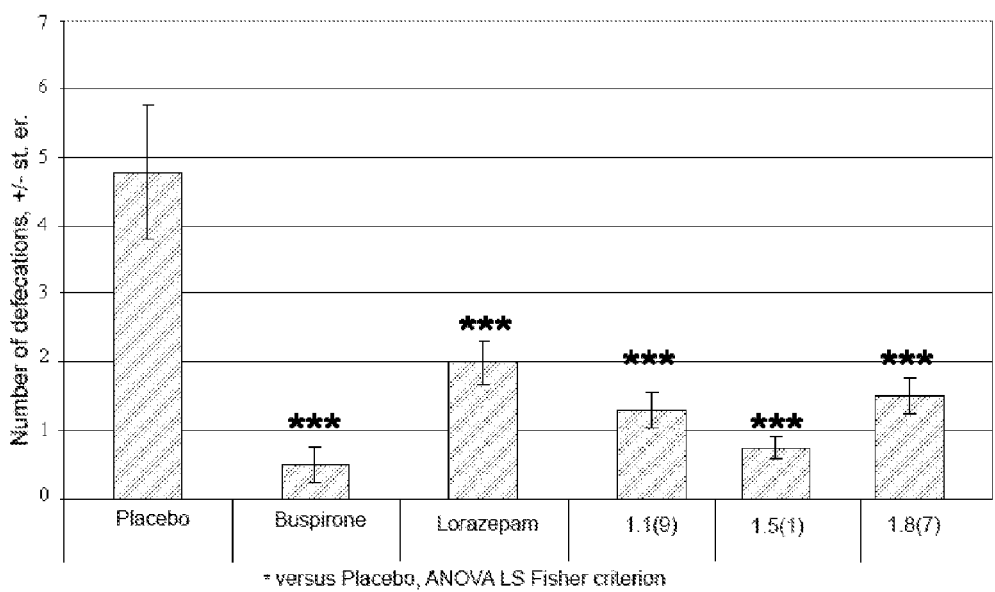

FIG. 8. Behavior of male mice of BALB/c line under the influence of compounds 1.1(9), 1.5 (1) and 1.8(7) and reference substances (Buspirone and Lorazepam) in the test "Mice Behavior in the Elevated Plus Maze". The number of defecations.

Figure 9:
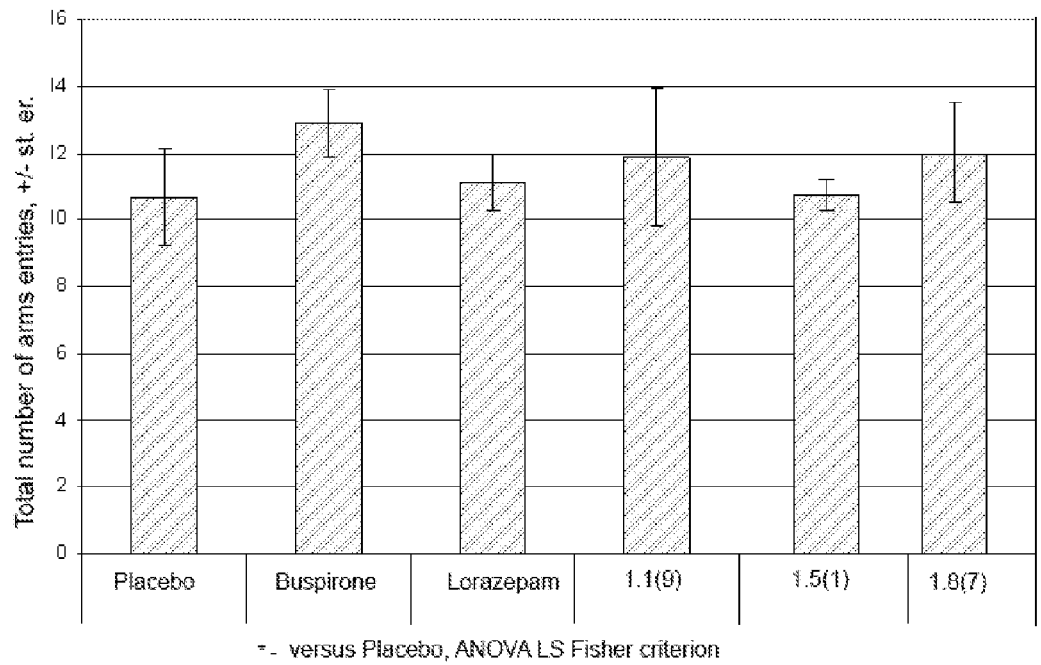

FIG. 9. Behavior of male mice of BALB/c line under the influence of compounds 1.1(9), 1.5 (1) and 1.8(7) and reference substances (Buspirone and Lorazepam) in the test "Mice Behavior in the Elevated Plus Maze". The total number of arm entries.

Figure 10:
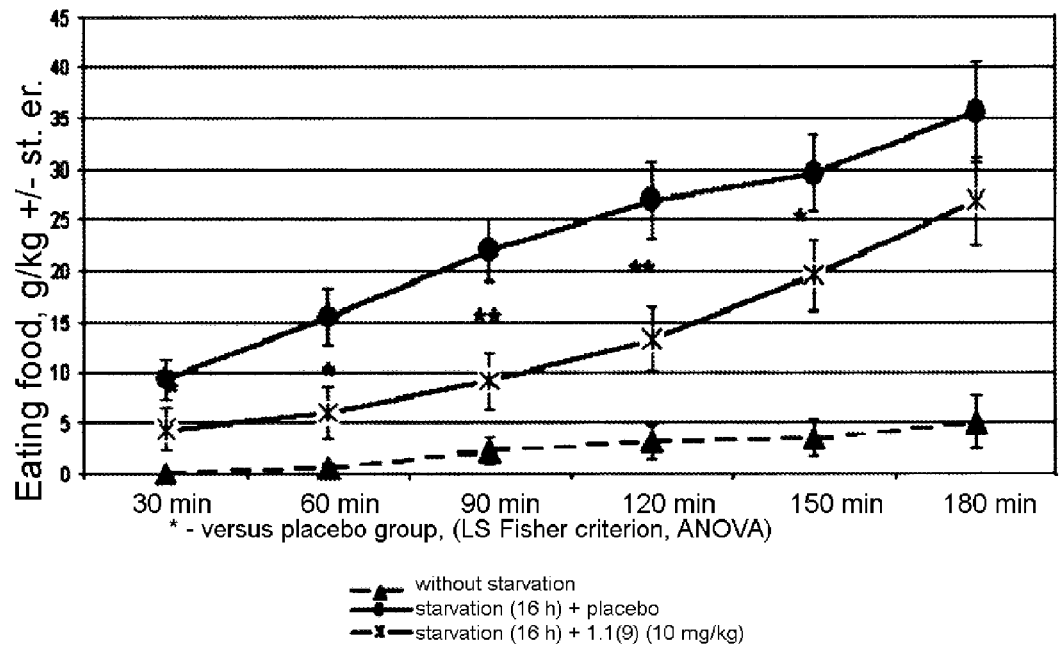

FIG. 10. Test results for appetite checkup in rats.

Figure 11:
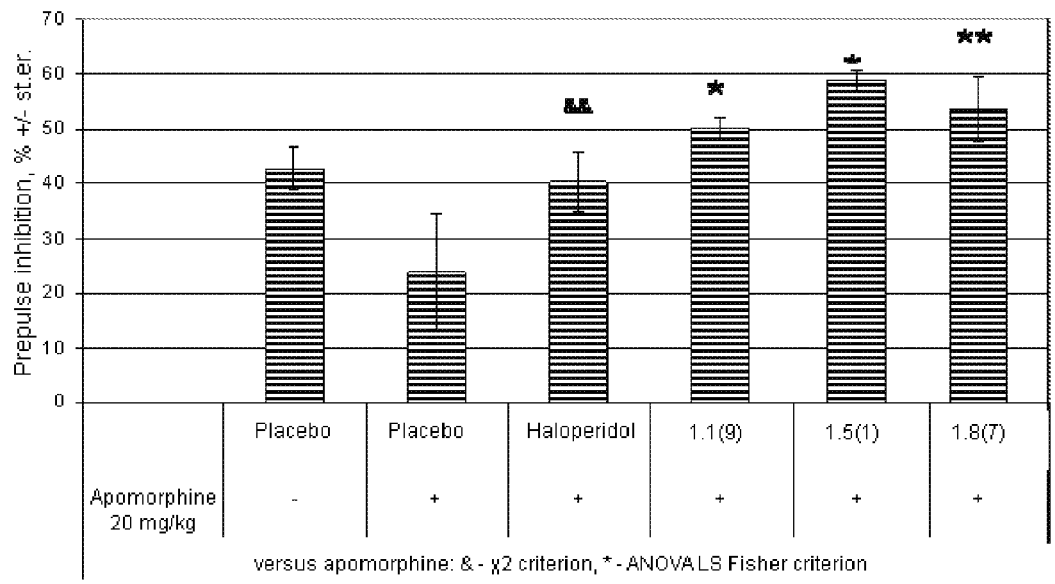

FIG. 11. The influence of compounds 1.1(9), 1.5 (1) and 1.8(7) on prepulse inhibition in reply to acoustic stimulus. Difference from the group of animals received placebo: *—according to LS—Fisher-test; &—according to chi square test.

Figure 12:
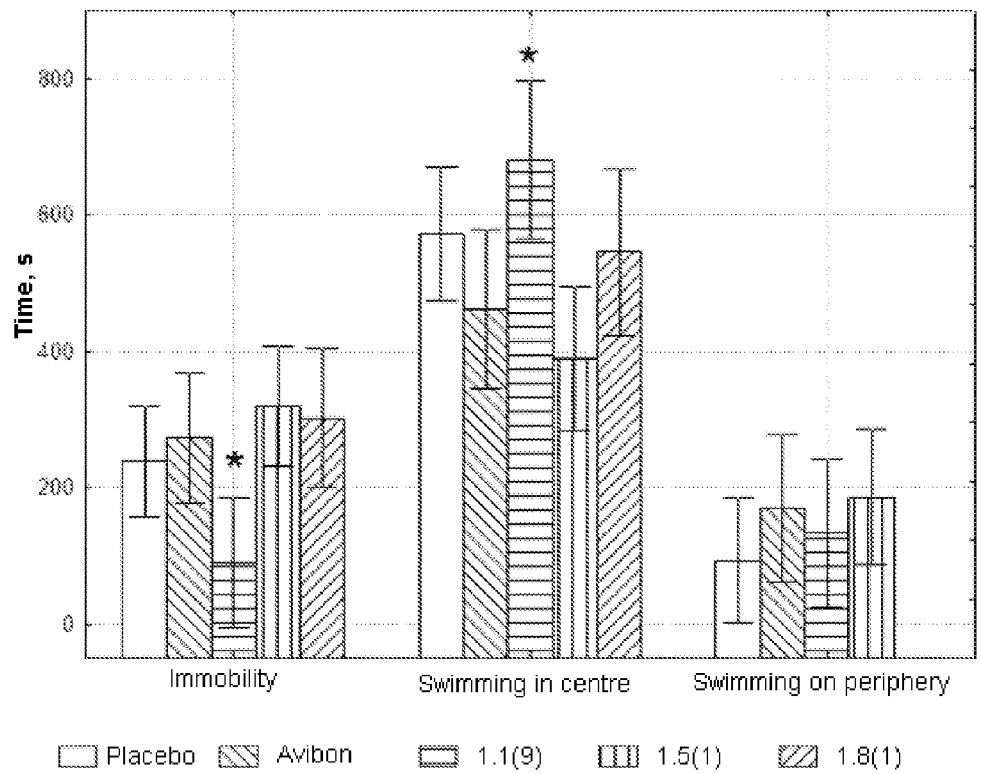

FIG. 12. Duration of depressive-like behavior and swimming of mice in the center and on the periphery of the vessel in the Porsolt's test (average value±standard error) after 4 days administration of compounds 1.1(9), 1.5 (1) and 1.8(7) in dose 1 mg/kg. Difference from the group of animals received placebo: *—p<0.05.

Figure 13:
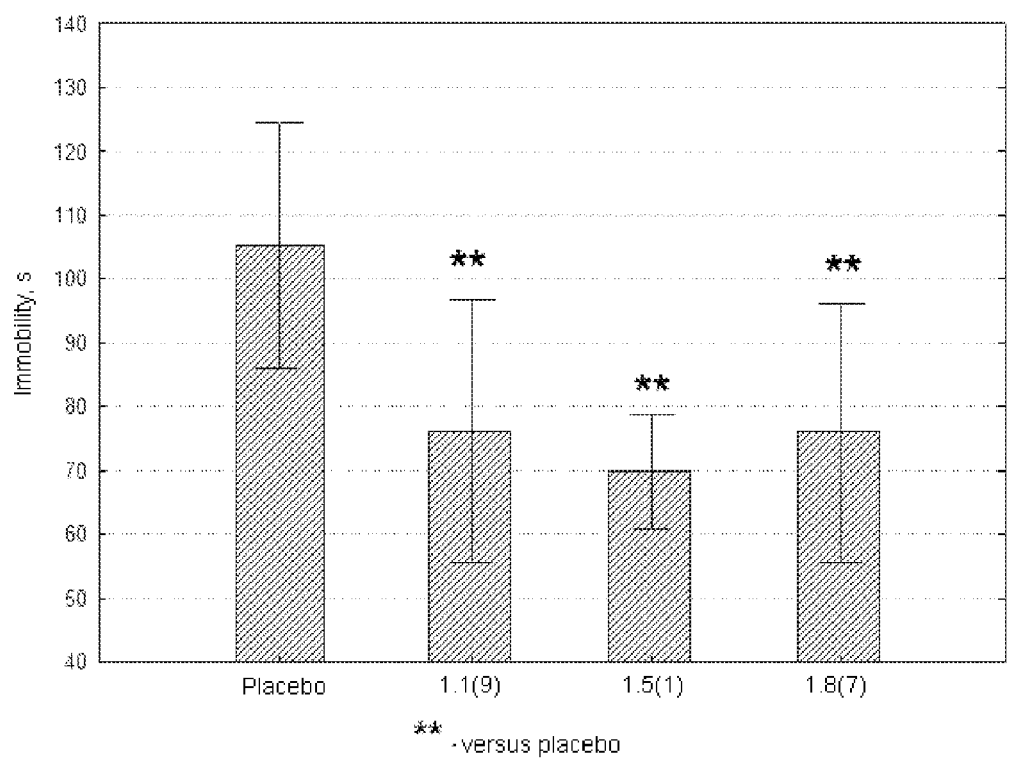

FIG. 13. Test results for compounds 1.1(9), 1.5 (1) and 1.8(7) in the tail suspension test.

Below the invention is described by means of specific examples, which illustrate but not limit the scope of the invention.

EXAMPLE 1

Synthesis of methyl-[3-piperazin-1-yl-6-(3-chlorophenylsulfonyl)phenyl]-amine hydrochloride 1.1 (2).HCl Compounds 2(3)-2(6) were prepared according to the methods given in US2004/0014966A1. Scheme 1

A mixture of tert-butyl-3-(3-methylamino)-4-(phenylsulfonylphenyl)piperazine-1-carboxylate 2(6) (218 mg, 0.5 mmol), 50% NaOH (0.13 g) water solution, toluene (0.22 ml), dimethyl sufate (53 mkl, 0.55 mmol) and tetrabutylammonium bromide (10 mg, 0.033 mmol) was stirred for 12 h. Then the reaction mixture was poured into 5% HCl water solution (10 ml) and extracted with $CH_2Cl_2$. Organic layer was separated, dried over $Na_2SO_4$, filtered and evaporated to dryness. Reaction product 2(7) was isolated by means of HPLC method, it was dissolved in a small amount of methanol, equivalent amount of 0.2 M HCl solution in methanol was added, and the reaction product 1.1(2).HCl was precipitated by ether and filtered off. Yield is 97%. LCMS (M+1) 367; $^1$H NMR (DMSO-D6, 400 MHz) δ 2.80 (s, 3H), 3.06 (m, 2H), 3.14 (d, d, $J_1$=3.5 Hz, $J_2$=4.5 Hz, 2H), 3.42 (m, 2H), 4.52 (s, 2H), 5.82 (t, $J_1$=0.39 Hz, $J_2$=0.42 Hz, $J_3$=8.8 Hz, 1H), 7.06 (s, 1H), 7.17 (s, 1H), 7.29 (d, $J_1$=0.51 Hz, $J_2$=8.04 Hz, 1H), 7.53 (s, 1H), 7.81 (s, 1H), 7.90 (s, 1H).

In analogous manner starting from 3-chloro-thiophenol 2(2) and N-methyl-piperazine compound 1.1(5) was prepared; in the synthesis of compounds 1.1(7)-1.1(9) 2,4-difluoronitrobenzene was used as a starting material. Methyl-[3-(4-methyl-piperazin-1-yl)-6-(3-chlorophenylsulfonyl)

phenyl]-amine 1.1(5), LCMS (M+1) 351; $^1$H NMR (DMSO-D6, 400 MHz) δ 2.30 (m, 3H), 2.52 (m, 2H), 2.59 (d.d, $J_1$=4.5 Hz, $J_2$=3.5 Hz, 2H), 2.8 (s, 3H), 3.11 (m, 2H), 3.18 (m, 2H), 5.82 (d.d, $J_1$=13.2 Hz, $J_2$=0.42 Hz, 1H), 6.39 (s, 1H), 7.07 (t, J=13.3 Hz, 1H), 7.18 (d.d., $J_1$=8.8 Hz, $J_2$=1.9 Hz, 1H), 7.29 (br.s., 1H), 7.53 (s, 1H), 7.81 (s, 1H), 7.90 (d, $J_1$=13.2 Hz, $J_2$=2.46 Hz, 1H), 9.0 (s, 1H); methyl-(4-piperazin-1-yl-6-phenylsulfonylphenyl)-amine 1.1(7), LCMS (M+1) 368; $^1$H NMR (DMSO-D6, 400 MHz) δ 2.8 (s, 1H), 3.05 (m, 2H), 3.14 (d.d, $J_1$=4.5 Hz, $J_2$=3.5 Hz, 2H), 3.35 (m, 2H), 3.42 (m, 2H), 4.52 (d, 2H), 5.83 (d, J=0.42 Hz, 1H), 7.10 (d.d, $J_1$=1.9 Hz, $J_2$=0.42 Hz, 1H), 7.17 (d.d, $J_1$=8.8 Hz, $J_2$=1.9 Hz, 1H), 7.37 (t, $J_1$=7.58 Hz, $J_2$=1.47 Hz, 1H), 7.65 (d, J=7.58 Hz, 1H), 7.79 (d.d, $J_1$=7.53 Hz, $J_2$=1.25 Hz, 1H); methyl-[4-piperazin-1-yl-6-(3-chlorophenylsulfonyl)phenyl]-amine 1.1(8), LCMS (M+1) 337; $^1$H NMR (DMSO-D6, 400 MHz) δ 2.8 (s, 3H), 3.05 (m, 2H), 3.14 (m, 2H), 3.34 (m, 2H), 3.42 (m, 2H), 4.52 (d, 2H), 5.83 (d, J=0.42 Hz, 1H), 7.06 (d.d, $J_1$=1.9 Hz, $J_2$=0.42 Hz, 1H), 7.19 (d.d, $J_1$=8.8 Hz, $J_2$=1.9 Hz, 1H), 7.29 (t, $J_1$=8.04 Hz, $J_2$=0.51 Hz, 1H), 7.52 (t, $J_1$=8.04 Hz, $J_2$=2.46 Hz, 1H), 7.8 (t, $J_1$=7.53 Hz, $J_2$=2.46 Hz, $J_3$=1.69 Hz, 1H), 7.90 (d, J=2.46 Hz, 1H); methyl-[4-piperazin-1-yl-6-(3-fluorophenylsulfonyl)phenyl]-amine 1.1(9), LCMS (M+1) 321; $^1$H NMR (DMSO-D6, 400 MHz) δ 2.8 (t, $J_1$=13.35 Hz, $J_2$=0.39 Hz, 3H), 3.04 (d.d, $J_1$=7.5 Hz, $J_2$=4.5 Hz, 2H), 3.14 (d.d, $J_1$=4.5 Hz, $J_2$=3.5 Hz, 2H), 3.33 (m, 2H), 3.42 (d, J=13.2 Hz, 2H), 4.52 (s, 2H), 5.83 (d, J=0.42 Hz, 1H), 7.12 (s, 1H), 7.18 (t, $J_1$=8.8 Hz, $J_2$=1.9 Hz, 1H), 7.27 (m, 1H), 7.33 (t, $J_1$=8.24 Hz, $J_2$=0.51 Hz, 1H), 7.62 (d, J=1.74 Hz, 1H), 7.70 (d, J=1.74 Hz, 1H); methyl-[4-(4-methylpiperazin-1-yl)-6-phenylsulfonylphenyl]-amine 1.1(10), LCMS (M+1) 346; $^1$H NMR (DMSO-D6, 400 MHz) δ 2.29 (t, $J_1$=13.35 Hz, $J_2$=0.99 Hz, 3H), 2.51 (m, 2H), 2.59 (m, 2H), 2.8 (t, $J_1$=13.35 Hz, $J_2$=0.39 Hz, 3H), 3.11 (m, 2H), 3.18 (m, 2H), 5.83 (d, J=0.42 Hz, 1H), 6.39 (s, 1H), 7.11 (s, 1H), 7.18 (t, $J_1$=8.80 Hz, $J_2$=1.90 Hz, 2H), 7.38 (m, 2H), 7.65 (d, J=7.58 Hz, 1H), 7.79 (t, $J_1$=7.53 Hz, $J_2$=1.25 Hz, 2H); methyl-[4-(4-methylpiperazin-1-yl)-6-(3-chlorophenylsulfonyl)phenyl]-amine 1.1(11), LCMS (M+1) 380; $^1$H NMR (DMSO-D6, 400 MHz) δ 2.29 (t, $J_1$=13.35 Hz, $J_2$=0.99 Hz, 3H), 2.51 (m, 2H), 2.59 (m, 2H), 2.8 (t, $J_1$=13.35 Hz, $J_2$=0.39 Hz, 3H), 3.11 (m, 2H), 3.18 (m, 2H), 5.84 (d, J=0.42 Hz, 1H), 6.39 (s, 1H), 7.06 (s, 1H), 7.20 (t, $J_1$=8.80 Hz, $J_2$=1.90 Hz, 1H), 7.29 (t, $J_1$=8.04 Hz, $J_2$=0.51 Hz, 1H), 7.52 (t, $J_1$=8.04 Hz, $J_2$=2.46 Hz, 1H), 7.80 (t, $J_1$=7.53 Hz, $J_2$=2.46 Hz, 1H), 7.89 (s, 1H); methyl-[4-(4-methylpiperazin-1-yl)-6-(3-fluorophenylsulfonyl)phenyl]-amine 1.1(12), LCMS (M+1) 364; $^1$H NMR (DMSO-D6, 400 MHz) δ 2.29 (t, $J_1$=13.35 Hz, $J_2$=0.99 Hz, 3H), 2.51 (m, 2H), 2.59 (m, 2H), 2.8 (t, $J_1$=13.35 Hz, $J_2$=0.39 Hz, 3H), 3.11 (m, 2H), 3.18 (m, 2H), 5.84 (d, J=0.42 Hz, 1H), 6.39 (s, 1H), 7.13 (s, 1H), 7.19 (m, 2H), 7.26 (m, 1H), 7.33 (t, $J_1$=8.24 Hz, $J_2$=0.51 Hz, 1H), 7.59 (d, J=1.74 Hz, 1H), 7.69 (t, $J_1$=7.53 Hz, $J_2$=1.69 Hz, 1H).

EXAMPLE 2

Synthesis of N-methyl-N-[4-(phenylsulfonyl)-1,1'-biphenyl-3-yl]amine 1.1(13). Scheme 2

A solution of 1-chloro-4-iodo-2-nitrobenzene 4(1) (5.64 g, 0.02 mol) and Na phenylsulfinate 4(2) (3.28 g, 0.02 mol) in DMF (80 ml) was stirred for 12 h at 120° C. Then, the reaction mixture was cooled, poured into water and extracted with ethyl acetate. Organic layer was dried over $Na_2SO_4$, filtered and evaporated to dryness. The mixture was separated by means of column chromatography, eluent—ethyl acetate: hexane 1:4. It gave 2.4 g (30.6%) 4-iodo-2-nitro-1-(phenylsulfonyl)benzene 4(3).

Argon was passed through a mixture of phenylboronic acid (186.5 mg, 1.52 mmol) and $Na_2CO_3$ (406.8 mg, 3.83 mmol) in water ethanol (water 3.8 ml, ethanol 13.7 ml) at stirring for 30 min at 90° C., then cooled to 80° C. and compound 4(3) (732.2 mg, 1.89 mmol) was added to the reaction mixture in argon current, inert gas was passed for another 10 min, then bis-triphenylphosphinepalladium dichloride (33.9 mg) was added and argon was passed for another 5 min. The reaction mixture was stirred for 2 h at 85° C. in argon atmosphere, cooled, gradually formed solid was filtered off. It was suspended in $CH_2Cl_2$, filtered again, mother liquor was evaporated to dryness. Ethyl acetate was added to the residue and the reaction product was filtered off, it gave 340 mg (52.7%) of 3-nitro-4-phenylsulfonylbiphenyl 4(4), which was reduced to amine 4(5) by Fe. Fe powder (260 mg, 4.65 mmol) was added in small portions to a suspension of compound 4(4) (315 mg, 0.93 mmol) in AcOH (3 ml) at stirring. The mixture was stirred at 70° C. for 3 h, cooled, water was added, the precipitated solid was filtered off, dried, washed with mixture of ethyl acetate:hexane 7:3, it gave 185 mg (64%) of 4-(phenylsulfonyl)biphenyl-3-amine 4(5).

A mixture of compound 4(5) (175 mg, 0.57 mmol) and formic acid (0.5 ml) was refluxed for 1 h and evaporated to dryness. $CHCl_3$ was added to the residue, organic layer was washed with 10% $NaHCO_3$ water solution, water, dried over $Na_2SO_4$, filtered and evaporated to dryness. Recrystallization from hexane gave 130 mg (67.7%) of N-(4-phenylsulfonyl)biphenyl-3-yl)formamide 4(6).

Borane-methyl sulfide complex (0.57 ml, 1.13 mmol, 2M) was added to a mixture of compound 4(6) (127 mg, 0.377 mmol) in anhydrous THF (2.3 ml). The mixture was stirred for 12 h at 20° C. It was washed with saturated $NaHCO_3$ solution, extracted with $CH_2Cl_2$, dried over $Na_2SO_4$, filtered and evaporated to dryness. Reaction product—N-methyl-N-[4-(phenylsulfonyl)-1,1'-biphenyl-3-yl]amine 1.1(13) was isolated by means of HPLC. LCMS (M+1) 324; $^1$H NMR ($CDCl_3$, 400 MHz) δ 7.94 (t, J=6.8 Hz, 3H), 7.57 (t, J=6.8 Hz, 3H), 7.45 (m, 5H), 6.96 (d.d, $J_1$=8.4 Hz, $J_2$=1.6 Hz, 1H), 6.83 (s, 1H), 6.45 (q, J=4.8 Hz, 1H), 2.93 (d, J=4.8 Hz, 3H).

EXAMPLE 3

Synthesis of methyl-(5-pyridin-3-yl-2-phenylsulfonylphenyl)-amine 1.1(14). Scheme 3

Argon was passed through a mixture of 3-pyridineboronic acid (187 mg, 1.53 mmol) and $Na_2CO_3$ (408 mg, 3.84 mmol) in water ethanol (water 3.74 ml, ethanol 14.96 ml) at stirring at 90° C. for 30 min and cooled to 80° C. 4-Iodo-2-nitro-1-(phenylsulfonyl)-benzene 4(3) (734 mg, 1.9 mmol) was added to the reaction mixture in argon current, inert gas was passed for another 10 min, then bis-triphenylphosphinepalladium dichloride (34 mg) was added and argon was passed for additional 5 min. The reaction mixture was stirred for 2 h at 85° C. in argon atmosphere, then, cooled, water was added, and precipitated solid was filtered off. The reaction product was extracted from mother liquor with $CH_2Cl_2$, organic layer was dried over $Na_2SO_4$, filtered and evaporated to dryness. The residue was suspended in $CH_2Cl_2$, filtered off, mother liquor was evaporated, the residue washed with diethyl ether, it gave 460 mg (70.5%) of 3-(3-nitro-4-(phenylsulfonyl)phenyl)pyridine 5(1).

Fe powder (444 mg, 7.94 mmol) was added in small portions to agitated suspension of compound 5(1) (540 mg, 1.58 mmol) in AcOH (6 ml). The mixture was stirred at 70° C. for 3 h, cooled, water was added and the reaction product was extracted with ethyl acetate. Organic layer was separated, dried over $Na_2SO_4$, filtered and evaporated. The residue was washed with ethyl acetate:hexane 7:3 mixture, it gave 290 mg (59%) of 2-(phenylsulfonyl)-5-(pyridin-3-yl)phenyl-amine 5(2). (The synthesis was carried out according to the method given in Heterocycles 1996, Vol. 43, I. 2, p. 471-474).

A mixture of compound 5(2) (280 mg, 0.91 mmol) and HCOOH (0.71 ml) was refluxed for 1 h, cooled, water solution of $NaHCO_3$ was added to pH=7. The precipitated solid was filtered off, it gave 270 mg (87%) of N-(2-(phenylsulfonyl)-5-(pyridin-3-yl)phenyl)formamide 5(3).

Di-iso-butyl-aluminum hydride (1.1 ml, 1.7 mmol, 1.5 M) was added to a mixture of compound 5(3) (252 mg, 0.75 mmol) in dry toluene (2 ml). The mixture was stirred for 24 h at 20° C. It was washed with saturated $NaHCO_3$ solution, extracted with $CH_2Cl_2$, dried over $Na_2SO_4$, filtered and evaporated to dryness. The reaction product—N-methyl-2-(phenylsulfonyl)-5-(pyridin-3-yl)phenylamine 1.1(14)—was isolated by means of HPLC method. LCMS (M+1) 325; $^1$H NMR (DMSO-D6, 400 MHz) δ 8.90 (s, 1H), 8.60 (s, 1H), 8.01 (m, 4H), 7.60 (m, 4H), 7.06 (d, J=6 Hz, 1H), 6.94 (s, 1H), 6.50 (s, 1H), 2.89 (s, 3H).

EXAMPLE 4

The General Method for Synthesis of Substituted methyl-(4-piperazin-1-yl-2-phenylsulfonylnaphthalen-1-yl)-amines 1.2.1(1)-1.2.1(3). Scheme 4

A solution of compound 10(1) (23.32 g, 0.11 mol) in glacial AcOH was added over a period of one hour to agitated suspension of sodium perborate tetrahydrate (91.3 g, 5 eq.), the temperature of the reaction mixture was keeping within the range of 50-60° C. The reaction mixture was stirred at this temperature for 2 h until separation of sodium borate was completed. The mixture was cooled to room temperature, inorganic salt was filtered off, and icy water was added. Crude nitro-compound was filtered off and purified by chromatography on short column, it gave compound 10(2), 19.69 g (74%).

A solution of 2,4-dichloro-1-nitronaphthalene (19.36 g, 0.08 mol) and Na phenylsulfinate 4(2) (13.12 g, 0.08 mol) in DMF (320 ml) was stirred for 12 h at 50° C. After the reaction was completed the mixture was cooled, poured into cold water and extracted with ethyl acetate. Organic layer was dried over $Na_2SO_4$, filtered and evaporated to dryness. The mixture was separated by means of column chromatography, eluent—ethyl acetate:hexane 1:4. It gave compound 10(3) 8.4 g, (30.6%).

A solution of 4-chloro-1-nitro-2-(phenylsulfonyl)naphthalene (6.74 g, 0.02 mol) 10(3) and Boc-piperazine (3.72 g, 0.02 mol) in DMF (80 ml) was stirred for 12 h at 120° C. After the reaction was completed the mixture was cooled, poured into cold water and extracted with ethyl acetate. Organic layer was dried over $Na_2SO_4$, filtered and evaporated to dryness. The mixture was separated by means of column chromatography, eluent—ethyl acetate:hexane 1:4, it gave compound 10(4), 4.37 g, (43.5%). The prepared tert-butyl 4-(4-nitro-3-(phenylsulfonyl)naphthalen-1-yl)piperazin-1-carboxylate 10(4) was reduced with Fe.

Fe powder (2.61 g, 0.0466 mol) was added in small portions towards agitated suspension of compound 10(4) (4.62 g, 0.0093 mol) in AcOH (30 ml). The reaction mixture was stirred at 70° C. for 3 h, cooled, diluted with water; the precipitated solid was filtered off, it gave compound 10(5), 3.35 g (77%).

A mixture of tert-butyl 4-(4-amino-3-(phenylsulfonyl)naphthalen-1-yl)piperazine-1-carboxylate 10(5) (2.34 g, 0.5 mmol), 50% NaOH (0.13 g) water solution, toluene (0.22 ml), dimethyl sulfate (53 mid, 0.55 mmol) and tetrabutylammonium bromide (10 mg, 0.033 mmol) was stirred for 12 h. After that the reaction mixture was poured into 5% HCl water solution (10 ml) and extracted with $CH_2Cl_2$. Organic layer was separated, dried over $Na_2SO_4$, filtered and evaporated to dryness. The reaction product—compound 10(6) was isolated by means of HPLC, the base was dissolved in a small amount of methanol, then equivalent amount of 0.2 M HCl solution in methanol was added. Reaction product 1.2.1(1) .HCl was precipitated with ether and filtered off. Yield was 97%. LCMS (M+1) 367; $^1$H NMR (DMSO-D6, 400 MHz) δ 3.06 (t, $J_1$=7.5 Hz, $J_2$=4.5 Hz, 2H), 3.14 (t, $J_1$=4.5 Hz, $J_2$=3.5 Hz, 2H), 3.42 (m, 2H), 3.50 (m, 2H), 3.69 (s, 3H), 5.45 (s, 2H), 7.21 (d.d, $J_1$=8.16 Hz, $J_2$=7.0 Hz, 1H), 7.30 (s, 1H), 7.38 (s, 1H), 7.65 (d, J=7.58 Hz, 1H), 7.80 (t, $J_1$=7.53 Hz, $J_2$=1.25 Hz, 1H), 8.12 (t, $J_1$=2.18 Hz, $J_2$=0.6 Hz, 1H), 8.29 (d, J=0.16 Hz, 1H).

Compounds 1.2.1(2) and 1.2.1(3) were prepared in analogous manner using 3-chloro- and 3-fluoro-substituted Na phenylsulfinate ($R^1$=Cl, F), respectively; methyl-[4-piperazin-1-yl-2-(3-chlorophenylsulfonyl)naphthalen-1-yl]-amine 1.2.1(2), LCMS (M+1) 401; $^1$H NMR (DMSO-D6, 400 MHz) δ 3.06 (m, 2H), 3.14 (t, $J_1$=4.5 Hz, $J_2$=3.5 Hz, 2H), 3.41 (m, 2H), 3.50 (d, J=4.5 Hz, 2H), 3.69 (s, 3H), 5.45 (s, 2H), 7.22 (m, 1H), 7.30 (t, $J_1$=8.16 Hz, $J_2$=0.28 Hz, 1H), 7.53 (m, 1H), 7.79 (t, $J_1$=7.53 Hz, $J_2$=2.46 Hz, 1H), 7.89 (d, J=2.46 Hz, 1H), 8.12 (d, J=2.18 Hz, 1H), 8.29 (m, 1H); methyl-[4-piperazin-1-yl-2-(3-fluorophenylsulfonyl)naphthalen-1-yl]-amine 1.2.1(3), LCMS (M+1) 385; $^1$H NMR (DMSO-D6, 400 MHz) δ 3.06 (d.d, $J_1$=8.16 Hz, $J_2$=0.28 Hz, 2H), 3.15 (m, 2H), 3.42 (m, 2H), 3.50 (m, 2H), 3.69 (s, 3H), 5.45 (s, 2H), 7.22 (d.d, $J_1$=8.16 Hz, $J_2$=7.0 Hz, 1H), 7.27 (m, 1H), 7.30 (d.d, $J_1$=8.16 Hz, $J_2$=0.28 Hz, 1H), 7.33 (d.d, $J_1$=8.24 Hz, $J_2$=0.51 Hz, 1H), 7.60 (d, J=1.74 Hz, 1H), 7.69 (t, $J_1$=7.53 Hz, $J_2$=1.69 Hz, 1H), 8.12 (m, 1H), 8.29 (m, 1H).

Compounds 1.2.1(4)-1.2.1(6) were prepared in analogous manner, using N-methylpiperazine instead of Boc-piperazine. Methyl-[4-(4-methylpiperazin-1-yl)-2-phenylsulfonyl-naphthalen-1-yl]-amine 1.2.1(4), LCMS (M+1) 396; $^1$H NMR (DMSO-D6, 400 MHz) δ 2.34 (t, $J_1$=13.35 Hz, $J_2$=0.99 Hz, 3H), 2.51 (m, 2H), 2.59 (m, 2H), 3.19 (m, 2H), 3.25 (m, 2H), 3.69 (d, J=13.35 Hz, 3H), 7.27 (m, 3H), 7.38 (t, $J_1$=7.53 Hz, $J_2$=0.55 Hz, 1H), 7.65 (d, J=7.58 Hz, 1H), 7.79 (d, J=7.58 Hz, 2H), 8.12 (d, J=2.18 Hz, 1H), 8.24 (s, 1H), 8.29 (t, $J_1$=8.16 Hz, $J_2$=0.60 Hz, 1H); methyl-[4-(4-methylpiperazin-1-yl)-2-(3-chlorophenylsulfonyl)naphthalen-1-yl]-amine 1.2.1(5), LCMS (M+1) 430; $^1$H NMR (DMSO-D6, 400 MHz) δ 2.34 (t, $J_1$=13.35 Hz, $J_2$=0.99 Hz, 3H), 2.51 (m, 2H), 2.59 (m, 2H), 3.19 (m, 2H), 3.25 (m, 2H), 3.69 (d, J=13.35 Hz, 3H), 7.19 (t, $J_1$=8.16 Hz, $J_2$=2.18 Hz, 1H), 7.29 (t, $J_1$=8.16 Hz, $J_2$=2.18 Hz, 1H), 7.30 (t, $J_1$=8.16 Hz, $J_2$=2.18 Hz, 1H), 7.51 (t, $J_1$=8.04 Hz, $J_2$=2.46 Hz, 1H), 7.78 (d, J=7.53 Hz, 1H), 7.88 (s, 1H), 8.12 (d, J=0.60 Hz, 1H), 8.24 (s, 1H), 8.29 (m, 1H); methyl-[4-(4-methylpiperazin-1-yl)-2-(3-fluorophenylsulfonyl)naphthalen-1-yl]-amine 1.2.1(6), LCMS (M+1) 414; $^1$H NMR (DMSO-D6, 400 MHz) δ 2.34 (t, $J_1$=13.35 Hz, $J_2$=0.99 Hz, 3H), 2.51 (m, 2H), 2.59 (m, 2H), 3.19 (m, 2H), 3.25 (m, 2H), 3.69 (d, J=13.35 Hz, 3H), 7.21 (t, $J_1$=8.16 Hz, $J_2$=2.18 Hz, 1H), 7.27 (t, $J_1$=8.24 Hz, $J_2$=1.74 Hz, 1H), 7.30 (m, 2H), 7.60 (s, 1H), 7.71 (d.d, $J_1$=7.53 Hz, $J_2$=1.69 Hz, 1H), 8.11 (d, J=0.60 Hz, 1H), 8.24 (s, 1H), 8.29 (m, 1H).

EXAMPLE 5

General Method for Synthesis of Substituted methyl-(5-piperazin-1-yl-2-phenylsulfonylnaphthalen-1-yl)-amines 1.2.2-compounds 1.2.2(1)-1.2.2(6). Scheme 5

N-(2-Bromo-5-nitronaphthalen-1-yl)acetamide 11(1) (8.2 g, 30.7 mmol) was added to a suspension of 60% NaH (1.6 mg, 40 mmol) in DMF (30 ml) and mixture was stirred for 1 h at 50° C. The reaction mixture was cooled to room temperature, then methyl iodide (5 ml) was added. The mixture was stirred at room temperature for 15 h. The reaction solution was poured onto icy water and extracted with ethyl acetate. Organic layer was washed with salted water and evaporated at reduced pressure. The obtained residue was purified by column chromatography on silica, eluent hexane/ethyl acetate, from 4:1 to 3:2, it gave compound 11(2), 9.9 g, (96%).

A mixture of N-(2-bromo-5-nitronaphthalen-1-yl)-N-methylacetamide 11(2) (7.83 g, 0.024 mol), Na phenylsulfinate (19.92 g, 0.12 mol), and CuJ (22.95 g, 0.12 mol) in NMP (100 ml) was heated at 150° C. in argon current for 3 h. After cooling to room temperature the reaction mixture was diluted with methanol and filtered. The filtrate was evaporated and product was purified by column flash chromatography, eluent—$CH_2Cl_2$/MeOH/$NH_4OH$, it gave compound 11(3), 7.29 g, (78%). The prepared N-methyl-N-(5-nitro-2-(phenylsulfonyl)naphthalen-1-yl)acetamide 11(3) was reduced with Fe.

Fe powder (5.22 g, 0.0932 mol) was added in small portions towards agitated suspension of compound 11(3) (7.15 g, 0.0186 mol) in AcOH (60 ml). The reaction mixture was stirred at 70° C. for 3 h, cooled, diluted with water; precipitated solid was filtered off, it gave compound 11(4), 5.07 g (77%).

A mixture of N-(5-amino-2-(phenylsulfonyl)naphthalen-1-yl)-N-methylacetamide 11(4) (3.54 g, 1 mmol), bis-(2-chloroethyl)-amine hydrochloride (0.18 g, 1 mmol), $K_2CO_3$ (0.14 g, 1 mmol), KJ (0.08 g, 0.5 mmol) and n-butanol (5 ml) was stirred at reflux for 72 h. After cooling to room temperature the solvent was evaporated, the residue was treated with water (20 ml) and extracted with $CH_2Cl_2$. Purification was carried out by means of flash chromatography, eluent—$CH_2Cl_2$:2N methanol $NH_3$ 96:4, it gave compound 11(5) R'$_2$=H, 3.64 g, (86%).

A solution of N-methyl-N-(2-(phenylsulfonyl)-5-(piperazin-1-yl)naphthalen-1-yl)acetamide 11(5) (1.2 g, 2.8 mmol) and concentrated HCl (16.1 ml) in a mixture of water (16.1 ml) and ethanol (16.1 ml) was refluxed for 7 h at stirring. After the reaction was completed the solution was cooled, poured into 10% KOH solution (100 ml) and extracted with $CH_2Cl_2$. Organic layer was washed with water, NaCl saturated solution and dried over $Na_2SO_4$. The solvent was distilled at reduced pressure, the residue was purified by HPLC method, it gave compound 1.2.2(1) R'$_2$=H, 0.9 g (82%). LCMS (M+1) 382; $^1$H NMR (DMSO-D6, 400 MHz) δ 3.06 (m, 2H), 3.14 (m, 2H), 3.42 (m, 2H), 3.50 (s, 1H), 3.69 (s, 1H), 5.45 (s, 2H), 6.91 (d.d, $J_1$=7.89 Hz, $J_2$=1.16 Hz, 1H), 7.13 (d, J=8.27 Hz, 1H), 7.38 (d.d, $J_1$=7.58 Hz, $J_2$=1.47 Hz, 1H), 7.65 (d, J=7.58 Hz, 1H), 7.78 (m, 1H), 7.92 (d, J=8.7 Hz, 1H), 8.23 (m, 1H), 8.29 (m, 1H).

Compounds 1.2.2(2)-1.2.2(6) were prepared in analogous manner using 3-chloro- and 3-fluoro-substituted Na phenylsulfinate ($R^1$=Cl, F) and also 2-chloro-N-(2-chloroethyl)-N-methylethylamine; methyl-[5-piperazin-1-yl-2-(3-chlorophenylsulfonyl)naphthalen-1-yl]-amine 1.2.2(2), LCMS (M+1) 416; $^1$H NMR (DMSO-D6, 400 MHz) δ 3.06 (m, 2H), 3.16 (d.d, $J_1$=4.50 Hz, $J_2$=3.50 Hz, 2H), 3.41 (m, 2H), 3.50 (m, 2H), 3.69 (s, 3H), 5.45 (s, 2H), 6.91 (d.d, $J_1$=7.89 Hz, $J_2$=1.16 Hz, 1H), 7.15 (d, J=8.27 Hz, 1H), 7.29 (d.d, $J_1$=8.04 Hz, $J_2$=0.51 Hz, 1H), 7.53 (m, 1H), 7.79 (d.d, $J_1$=7.53 Hz, $J_2$=2.46 Hz, 1H), 7.91 (m, 1H), 8.19 (d, J=8.7 Hz, 1H), 8.29 (d, J=8.27 Hz, 1H); methyl-[5-piperazin-1-yl-2-(3-fluorophenylsulfonyl)naphthalen-1-yl]-amine 1.2.2(3), LCMS (M+1) 400; $^1$H NMR (DMSO-D6, 400 MHz) δ 3.06 (m, 2H), 3.16 (m, 2H), 3.43 (m, 2H), 3.50 (m, 2H), 3.69 (s, 3H), 5.45 (s, 2H), 6.91 (d.d, $J_1$=7.89 Hz, $J_2$=1.16 Hz, 1H), 7.13 (d, J=8.27 Hz, 1H), 7.27 (m, 1H), 7.60 (m, 1H), 7.69 (d.d, $J_1$=7.53 Hz, $J_2$=1.74 Hz, 1H), 7.91 (m, 1H), 8.23 (m, 1H), 8.28 (d, J=8.70 Hz, 1H); methyl-[5-(4-methylpiperazin-1-yl)-2-phenylsulfonylnaphthalen-1-yl]-amine 1.2.2(4), LCMS (M+1) 396; $^1$H NMR (DMSO-D6, 400 MHz) δ 2.34 (d.d, $J_1$=13.35 Hz, $J_2$=0.99 Hz, 3H), 2.51 (t, $J_1$=7.50 Hz, $J_2$=4.50 Hz, 2H), 2.59 (t, $J_1$=4.50 Hz, $J_2$=3.50 Hz, 2H), 3.19 (m, 2H), 3.27 (m, 2H), 3.69 (d, J=13.35 Hz, 3H), 6.93 (d, J=7.89 Hz, 1H), 7.15 (d, J=8.27 Hz, 1H), 7.38 (d, J=8.27 Hz, 1H), 7.63 (d, J=7.58 Hz, 1H), 7.78 (t, $J_1$=7.53 Hz, $J_2$=2.15 Hz, 1H), 7.91 (d.d, $J_1$=8.70 Hz, $J_2$=0.60 Hz, 1H), 8.21 (m, 1H), 8.24 (m, 1H), 8.28 (m, 1H); methyl-[5-(4-methylpiperazin-1-yl)-2-(3-chlorophenylsulfonyl)naphthalen-1-yl]-amine 1.2.2(5), LCMS (M+1) 430; $^1$H NMR (DMSO-D6, 400 MHz) δ 2.34 (t, $J_1$=13.35 Hz, $J_2$=0.99 Hz, 3H), 2.51 (t, $J_1$=7.50 Hz, $J_2$=4.50 Hz, 2H), 2.59 (m, 2H), 3.19 (m, 2H), 3.27 (m, 2H), 3.69 (d, J=13.35 Hz, 3H), 6.92 (m, 1H), 7.13 (d, J=13.35 Hz, 1H), 7.29 (d, J=8.04 Hz, 1H), 7.53 (m, 1H), 7.79 (d.d, $J_1$=7.53 Hz, $J_2$=2.46 Hz, 1H), 7.88 (d, J=2.46 Hz, 1H), 7.91 (m, 1H), 8.18 (m, 1H), 8.24 (m, 1H), 8.29 (m, 1H); methyl-[5-(4-methylpiperazin-1-yl)-2-(3-fluorophenylsulfonyl)naphthalen-1-yl]-amine 1.2.2(6), LCMS (M+1) 414; $^1$H NMR (DMSO-D6, 400 MHz) δ 2.34 (t, $J_1$=13.35 Hz, $J_2$=0.99 Hz, 3H), 2.51 (m, 2H), 2.59 (m, 2H), 3.19 (m, 2H), 3.27 (d, J=10.83 Hz, 2H), 3.69 (d, J=13.35 Hz, 3H), 6.93 (d, J=7.89 Hz, 1H), 7.13 (d, J=8.27 Hz, 1H), 7.27 (m, 1H), 7.33 (d.d, $J_1$=8.24 Hz, $J_2$=0.51 Hz, 1H), 7.60 (d, J=1.74 Hz, 1H), 7.70 (d.d, $J_1$=7.53 Hz, $J_2$=1.69 Hz, 1H), 8.23 (m, 1H), 8.28 (m, 1H), 8.29 (t, $J_1$=8.27 Hz, $J_2$=1.16 Hz, 3H).

EXAMPLE 6

General Method for Preparation of Substituted methyl-(4-piperazin-1-yl-1-phenylsulfonylnaphthalen-2-yl)-amines 1.3-1.3(1-6). Scheme 6

A solution of 1,4-dichloro-2-nitronaphthalene 12(1) (4.84 g, 0.02 mol) and Na phenylsulfinate 4(2) (3.28 g, 0.02 mol) in DMF (80 ml) was stirred for 12 h at 50° C. After the reaction was completed the mixture was cooled, poured into cold water and extracted with ethyl acetate. Organic layer was dried over $Na_2SO_4$, filtered and evaporated to dryness. The mixture was separated by means of column chromatography, eluent—ethyl acetate:hexane 1:4. It gave compound 12(2) 4.8 g, (69%).

A solution of 4-chloro-2-nitro-1-(phenylsulfonyl)naphthalene 12(2) (4.8 g, 0.014 mol) and Boc-piperazine (2.65 g, 0.014 mol) in DMF (60 ml) was stirred for 12 h at 120° C. After the reaction was completed the mixture was cooled, poured into cold water and extracted with ethyl acetate. Organic layer was dried over $Na_2SO_4$, filtered and evaporated to dryness. The mixture was separated by means of column chromatography, eluent—ethyl acetate:hexane 1:4. It gave compound 12(3) (R'$_2$=Boc), 4.8 g (52%). The prepared tert-butyl 4-(3-nitro-4-(phenylsulfonyl)naphthalen-1-yl)piperazine-1-carboxylate 12(3) was reduced with Fe.

Fe powder (2.7 g, 0.048 mol) was added in small portions towards agitated suspension of compound 12(3) (4.8 g, 0.0096 mol) in AcOH (30 ml). The reaction mixture was stirred at 70° C. for 3 h, cooled, diluted with water; precipitated solid was filtered off, it gave compound 12(4) 2.34 g (63%).

A mixture of tert-butyl 4-(3-amino-4-(phenylsulfonyl) naphthalen-1-yl)piperazine-1-carboxylate 12(4) (1.5 g, 3 mmol) and formic acid (1.5 ml) was boiled for 1 h and evaporated at reduced pressure. $CHCl_3$ was added to the residue, the solution was washed with 10% $NaHCO_3$ water solution. Organic layer was separated, dried over $Na_2SO_4$, filtered and evaporated to dryness. The reaction product was recrystallized from hexane; it gave compound 12(5), 1.34 g (90.5%).

A solution of tert-butyl 4-(3-formamido-4-(phenylsulfonyl)naphthalen-1-yl)piperazine-1-carboxylate 12(5) (1.2 g, 2.4 mmol) in dioxane (3 ml) was poured into 5% HCl water solution (20 ml), kept for 15 min and extracted with $CH_2Cl_2$. Organic layer was separated, dried over $Na_2SO_4$, filtered and evaporated to dryness at reduced pressure. The product was isolated by means of HPLC, it gave compound 12(6), 0.89 g, (94%).

Borane-methyl sulfide complex (3.3 ml, 6.6 mmol, 2M) was added to N-(1-(phenylsulfonyl)-4-(piperazin-1-yl)naphthalen-2-yl)formamide 12(6) (0.89 g, 2.2 mmol) in anhydrous THF (17 ml) and the resultant mixture was stirred for 12 h at room temperature. Saturated $NaHCO_3$ solution was added and the mixture was extracted with $CH_2Cl_2$. Organic layer was separated, dried over $Na_2SO_4$, filtered and evaporated to dryness at reduced pressure. The final product was recrystallized from ethyl acetate, it gave compound 1.3(1), 0.54 g, (64.9%). LCMS (M+1) 382; $^1$H NMR (DMSO-D6, 400 MHz) δ 2.80 (t, $J_1$=13.35 Hz, $J_2$=0.39 Hz, 3H), 3.06 (m, 2H), 3.14 (m, 2H), 3.42 (m, 2H), 3.53 (m, 2H), 6.02 (m, 2H), 6.06 (m, 1H), 7.31 (d, J=7.00 Hz, 2H), 7.38 (m, 2H), 7.61 (d.d, $J_1$=7.58 Hz, $J_2$=1.25 Hz, 1H), 7.67 (m, 1H), 7.78 (d.d, $J_1$=8.70 Hz, $J_2$=1.40 Hz, 1H), 7.83 (m, 2H), 8.40 (t, $J_1$=8.16 Hz, $J_2$=2.18 Hz, 1H).

Compounds 1.3(2)-1.3(6) were prepared in analogous manner using 3-chloro- and 3-fluoro-substituted Na phenylsulfinate ($R^1$=Cl, F), and also N-methylpiperazine; methyl-[4-piperazin-1-yl-1-(1-chlorophenylsulfonyl)naphthalen-2-yl]-amine 1.3(2), LCMS (M+1) 416; $^1$H NMR (DMSO-D6, 400 MHz) δ 2.80 (t, $J_1$=13.35 Hz, $J_2$=0.39 Hz, 3H), 3.08 (m, 2H), 3.13 (m, 2H), 3.42 (m, 2H), 3.48 (m, 2H), 6.02 (m, 2H), 6.06 (m, 1H), 7.29 (d, J=7.00 Hz, 2H), 7.52 (t, $J_1$=8.04 Hz, $J_2$=1.69 Hz, 1H), 7.67 (m, 1H), 7.79 (d.d, $J_1$=8.70 Hz, $J_2$=1.40 Hz, 1H), 7.86 (d, J=2.46 Hz, 1H), 8.41 (t, $J_1$=8.16 Hz, $J_2$=2.18 Hz, 1H); methyl-[4-piperazin-1-yl-1-(1-fluorophenylsulfonyl)naphthalen-2-yl]-amine 1.3(3), LCMS (M+1) 400; $^1$H NMR (DMSO-D6, 400 MHz) δ 2.80 (t, $J_1$=13.35 Hz, $J_2$=0.39 Hz, 3H), 3.06 (m, 2H), 3.14 m, 2H), 3.42 (m, 2H), 3.50 (m, 2H), 6.02 (t, $J_1$=4.50 Hz, $J_2$=1.52 Hz, 2H), 6.06 (d.d, $J_1$=7.50 Hz, $J_2$=4.50 Hz, 1H), 7.31 (m, 3H), 7.58 (m, 1H), 7.67 (m, 2H), 7.78 (d.d, $J_1$=8.70 Hz, $J_2$=1.40 Hz, 1H), 8.42 (t, $J_1$=8.16 Hz, $J_2$=2.18 Hz, 1H); methyl-[4-(4-methylpiperazin-1-yl)-1-phenylsulfonylnaphthalen-2-yl]-amine 1.3(4), LCMS (M+1) 396; $^1$H NMR (DMSO-D6, 400 MHz) δ 2.34 (t, $J_1$=13.35 Hz, $J_2$=0.99 Hz, 3H), 2.51 (m, 2H), 2.59 (m, 2H), 2.80 (t, $J_1$=13.35 Hz, $J_2$=0.39 Hz, 3H), 3.15 (m, 2H), 3.28 (m, 2H), 6.07 (s, 1H), 7.31 (t, $J_1$=7.00 Hz, $J_2$=1.43 Hz, 2H), 7.38 (t, $J_1$=7.58 Hz, $J_2$=1.47 Hz, 2H), 7.67 (m, 2H), 7.83 (d, J=7.53 Hz, 2H), 8.40 (t, $J_1$=8.16 Hz, $J_2$=2.18 Hz, 1H); methyl-[4-(4-methylpiperazin-1-yl)-1-(3-chlorophenylsulfonyl)naphthalen-2-yl]-amine 1.3(5), LCMS (M+1) 430; $^1$H NMR (DMSO-D6, 400 MHz) δ 2.34 (t, $J_1$=13.35 Hz, $J_2$=0.99 Hz, 3H), 2.51 (m, 2H), 2.60 (m, 2H), 2.80 (t, $J_1$=13.35 Hz, $J_2$=0.39 Hz, 3H), 3.16 (m, 2H), 3.27 (m, 2H), 6.07 (s, 1H), 7.28 (t, $J_1$=8.04 Hz, $J_2$=1.69 Hz, 2H), 7.31 (t, $J_1$=7.00, Hz, $J_2$=0.1 Hz, 2H), 7.53 (t, $J_1$=8.04 Hz, $J_2$=1.69 Hz, 1H), 7.67 (m, 1H), 7.83 (d, J=7.53 Hz, 2H), 7.87 (s, 1H), 8.42 (t, $J_1$=8.16 Hz, $J_2$=2.18 Hz, 1H); methyl-[4-(4-methylpiperazin-1-yl)-1-(3-fluorophenylsulfonyl) naphthalen-2-yl]-amine 1.3(6), LCMS (M+1) 414; $^1$H NMR (DMSO-D6, 400 MHz) δ 2.34 (t, $J_1$=13.35 Hz, $J_2$=0.99 Hz, 3H), 2.51 (m, 2H), 2.60 (m, 2H), 2.80 (t, $J_1$=13.35 Hz, $J_2$=0.39 Hz, 3H), 3.19 (m, 2H), 3.27 (m, 2H), 6.07 (s, 1H), 7.26 (t, $J_1$=8.24 Hz, $J_2$=1.69 Hz, 2H), 7.32 (m, 2H), 7.59 (t, $J_1$=8.04 Hz, $J_2$=1.69 Hz, 1H), 7.69 (d, J=7.53 Hz, 1H), 7.80 (d, J=8.70 Hz, 1H), 8.42 (t, $J_1$=8.16 Hz, $J_2$=2.18 Hz, 1H).

EXAMPLE 7

Synthesis of methyl-(1-phenylsulfonylindolizin-2-yl)-amine 1.4.1(1). Scheme 7

Thiophenol 2(2) (2.77 g, 0.025 mol), cesium carbonate (24.65 g, 0.075 mol) and catalytical amount of cesium fluoride were added successively to a solution of 2-chloromethylpyridine 6(1) (1.13 g, 0.017 mol) in absolute DMF (28 ml). The reaction mixture was stirred at 50-60° C. for 2 h in argon current and left for night at 20° C. Solvent was removed in vacuo, the residue was dissolved in water, the reaction product was extracted with $CH_2Cl_2$, dried over $MgSO_4$, solvent was evaporated in vacuo. It gave 2-phenylsulphanylmethylpyridine 6(2), 3.2 g, (95%).

3-Chloroperoxybenzoic acid (5.7 g, 0.033 mol) was added in portions to a solution of compound 6(2) (3.06 g, 0.0152 mol) in dry $CH_2Cl_2$ (82.6 ml) previously cooled to 0° C., keeping the temperature in the range of −5-0° C. After addition was completed the reaction mixture was stirred at the same temperature for 6 h, diluted with ethyl acetate (98 ml) and saturated $NaHCO_3$ (152 ml) solution; organic layer was separated, washed additionally with saturated $NaHCO_3$ solution, dried over $Na_2SO_4$, the solvent was removed in vacuo, the residue was purified by flash-chromatography (eluent $CHCl_3$-ethyl acetate, 5:1). It gave 2-(phenylsulfonylmethyl)-pyridine 6(3), 2 g, (57%).

Ethyl bromopyruvate (4.52 g, 0.026 mol) was added to a solution of sulfone 6(3) (1.87 g, 0.008 mol) in THF (26.8 ml), the reaction mixture was stirred at reflux for 18 h, at that salt precipitated, the reaction mass was cooled, $K_2CO_3$ (2.2 g, 0.016 mol) was added and the resultant mixture was refluxed for 24 h, then cooled, diluted 5-fold with water; precipitated solid was filtered off, washed with water and dried. It gave ethyl 1-(phenylsulfonyl)indolizine-2-carboxylate 6(4), 1.85 g, (70%).

A solution of KOH (0.35 g, 0.00625 mol) in water (6.25 ml) was added to a suspension of ester 6(4) (1.65 g, 0.005 mol) in methanol (6.25 ml), the reaction mixture was stirred at 50° C. until full (about 8 h) dissolving of the solid; cooled, diluted with water and acidified with conc. HCl; precipitated solid was filtered off, washed with water and dried. It gave 1-(phenylsulfonyl)indolizine-2-carxylic acid 6(5), 1.02 g, (68%).

Diphenylphosphoryl azide (0.0033 mol) was added to a solution of acid 6(5) (1.01 g, 0.0033 mol) and triethylamine (0.34 g, 0.0033 mol) in tert-butanol (23.5 ml) in argon current. The reaction mixture was boiled for 20 h, the solvent was evaporated in vacuo, the residue was dissolved in benzene, washed with citric acid solution, water, and saturated $NaHCO_3$ solution. Organic layer was separated, dried over $Na_2SO_4$, the solvent was removed in vacuo, the residue was purified by flash-chromatography (eluent benzene-ethyl acetate, 20:1). It gave tert-butyl 1-(phenylsulfonyl)indolisin-2-yl carbamate, 0.83 g, (67%).

N-Boc-Aminoindazole 6(6) (0.74 g, 0.002 mol) was added to a suspension of lithium aluminum hydride (0.38 g, 0.01 mol) in absolute THF (50 ml) using external cooling with water. After the addition was completed the cooling was taken away, the reaction mixture was refluxed for 12 h, cooled, decomposed with water, stirred for 1 h; inorganic solid was filtered off; solvent was removed in vacuo; the residue was purified chromatographically (eluent—benzene-ethyl acetate, 25:1). It gave 0.26 g (45%) of methyl-1-(phenylsulfonylindolizin-2-yl)-amine 1.4.1(1). LCMS (M+1) 287; $^1$H NMR (DMSO-D6, 400 MHz) δ 8.27 (d, J=6.4 Hz, 1H), 7.91 (d,d, $J_1$=8 Hz, $J_2$=1.2 Hz, 2H), 7.28 (d, J=8.8 Hz, 1H), 7.54 (m, 3H), 7.09 (t d, $J_1$=7.2 Hz, $J_2$=1.2 Hz, 1H), 6.95 (s, 1H), 6.77 (d t, $J_1$=6.8 Hz, $J_2$=1.2 Hz, 1H), 5.39 (q, J=4.8 Hz, 1H), 2.73 (d, J=5.2 Hz, 3H). Amine 1.4.1(1) was dissolved in HCl solution in dioxane, the mixture was stirred for 1 h, diluted with ether, the precipitated solid was filtered off, washed with ether, and dried. It gave methyl-(5-methyl-1-phenylsulfonylindolizin-2-yl)-amine hydrochloride 1.4.1(1).HCl with quantitative yield (0.29 g).

Compounds 1.4.1(2) and 1.4.1(3) were prepared in analogous manner starting from 3-chloro- or 3-fluoro-thiophenols, respectively; methyl-[1-(3-chlorophenylsulfonyl)indolizin-2-yl]-amine 1.4.1(2), LCMS (M+1) 321; $^1$H NMR (DMSO-D6, 400 MHz) δ 2.98 (d, J=13.35 Hz, 3H), 6.47 (t, $J_1$=6.78 Hz, $J_2$=1.25 Hz, 1H), 7.31 (d,d, $J_1$=9.50 Hz, $J_2$=6.70 Hz, 1H), 7.37 (d,d, $J_1$=8.04 Hz, $J_2$=0.51 Hz, 1H), 7.52 (d,d, $J_1$=8.04 Hz, $J_2$=2.46 Hz, 1H), 7.95 (t, $J_1$=7.53 Hz, $J_2$=2.46 Hz, 1H), 8.06 (d,d, $J_1$=9.50 Hz, $J_2$=1.25 Hz, 1H), 8.14 (s, 1H), 8.44 (d, J=1.18 Hz, 1H); methyl-[1-(3-fluorophenylsulfonyl)indolizin-2-yl]-amine 1.4.1(3), LCMS (M+1) 305; $^1$H NMR (DMSO-D6, 400 MHz) δ 2.98 (d, J=13.35 Hz, 3H), 6.47 (t, $J_1$=6.78 Hz, $J_2$=1.25 Hz, 1H), 7.27 (m, 1H), 7.33 (d,d, $J_1$=9.50 Hz, $J_2$=1.01 Hz, 1H), 7.41 (m, 1H), 7.76 (d, J=1.74 Hz, 1H), 7.86 (d, J=7.53 Hz, 1H), 8.06 (d,d, $J_1$=9.50 Hz, $J_2$=1.25 Hz, 1H), 8.14 (s, 1H), 8.43 (d, J=1.18 Hz, 1H).

EXAMPLE 8

Synthesis of methyl-(3-methyl-1-phenylsulfonylindolizin-2-yl)-amine 1.4.1(4). Scheme 8

Sodium hydride (0.022 mol) as 60% suspension in mineral oil was added in small portions to a solution of N-Boc-aminoindazole 6(6) (3.72 g, 0.01 mol) in THF (100 ml) in argon current. The reaction mixture was stirred at 20° C. for 1 h, then CH$_3$I (4.26 g, 0.03 mol) was added and stirring was continued at 40° C. for 12 h, reaction mixture was diluted with water, precipitated solid was filtered off, washed with water and dried. It gave 3.2 g (80%) of tert-butyl methyl-(3-methyl-1-(phenylsulfonyl)indolizin-2-yl)carbamate 6(7).

Conc. HCl solution (12 ml) was added to a suspension of compound 6(7) (3.2 g, 0.008 mol) in iso-propanol (50 ml), the reaction mixture was stirred at 40° C. for 2 h, solvent was evaporated in vacuo, the residue was neutralized with NaHCO$_3$ water solution, precipitated solid was filtered off, washed with water and dried, it gave 2.26 g (94%) of methyl-(3-methyl-1-phenylsulfonyl)indolizin-2-yl)-amine 1.4.1(4). LCMS (M+1) 301; $^1$H NMR (DMSO-D6, 400 MHz) δ 2.51 (d, J=2.88 Hz, 3H), 2.98 (d, J=13.35 Hz, 3H), 6.72 (t, $J_1$=6.70 Hz, $J_2$=1.25 Hz, 1H), 7.08 (d, J=1.18 Hz, 1H), 7.30 (t, $J_1$=9.50 Hz, $J_2$=1.75 Hz, 1H), 7.44 (m, 1H), 7.60 (d, J=7.58 Hz, 1H), 7.90 (d, J=9.50 Hz, 1H), 8.0 (t, $J_1$=7.53 Hz, $J_2$=1.25 Hz, 1H).

Compounds 1.4.1(5) and 1.4.1(6) were prepared in analogous manner starting from 3-chloro- and 3-fluoro-thiophenols; methyl-[3-methyl-1-(3-chlorophenylsulfonyl)indolizin-2-yl]-amine 1.4.1(5), LCMS (M+1) 335; $^1$H NMR (DMSO-D6, 400 MHz) δ 2.51 (d, J=2.88 Hz, 3H), 2.97 (d, J=13.35 Hz, 3H), 6.74 (t, $J_1$=6.70 Hz, $J_2$=1.25 Hz, 1H), 7.08 (m, 1H), 7.28 (t, $J_1$=9.50 Hz, $J_2$=1.75 Hz, 1H), 7.39 (t, $J_1$=8.04 Hz, $J_2$=0.51 Hz, 1H), 7.53 (t, $J_1$=8.04 Hz, $J_2$=2.46 Hz, 1H), 7.89 (d, J=9.50 Hz, 2H), 8.02 (d, J=2.46 Hz, 1H); methyl-[3-methyl-1-(3-fluorophenylsulfonyl)indolizin-2-yl]-amine 1.4.1(6), LCMS (M+1) 319; $^1$H NMR (DMSO-D6, 400 MHz) δ 2.51 (d, J=2.88 Hz, 3H), 2.97 (d, J=13.35 Hz, 3H), 6.74 (t, $J_1$=6.70 Hz, $J_2$=1.25 Hz, 1H), 7.07 (d, J=1.18 Hz, 1), 7.27 (d, J=8.24 Hz, 1H), 7.41 (t, $J_1$=8.2 Hz, $J_2$=0.51 Hz, 1H), 7.74 (s, 1H), 7.84 (d, J=7.53 Hz, 1), 7.90 (t, $J_1$=9.5 Hz, $J_2$=1.18 Hz, 1H).

EXAMPLE 9

General Method for Preparation of Substituted methyl-(3-piperazin-1-yl-1-phenylsulfonylindolizin-2-yl)-amines 1.4.1(7)-1.4.1(9). Scheme 9

A solution of ethyl 1-(phenylsulfonyl)indolizin-2-carboxylate 6(4) (3.62 g, 0.0116 mol) in DMF (100 ml) was added during 5 min to a suspension of sodium hydride (0.56 g, 0.014 mol) at a temperature in the range of 0-10° C. The mixture was warmed to room temperature and stirred for 2 h. A solution of O-(4-nitrobenzoyl)hydroxylamine (2.51 g, 0.013 mol) in DMF (17.5 ml) was added during 1 h to the prepared solution previously cooled to −5° C. During this time additional amount of DMF was added in order to agitate arising thick solid. Obtained suspension was warmed to room temperature and stirred for 12 h, after that poured out into water (60 ml) and extracted with ethyl acetate (3×20 ml). Organic extracts were combined and evaporated to the volume of about 30 ml, washed with water and saturated salt solution, dried over MgSO$_4$ and evaporated to dryness; it gave compound 6(8) with nearly quantitative yield (4 g).

A mixture of ethyl 3-amino-1-(phenylsulfonyl)indolizine-2-carboxylate 6(8) (3.44 g, 10 mmol), bis-(2-chloroethyl)-amine hydrochloride (1.8 g, 10 mmol), K$_2$CO$_3$ (1.4 g, 10 mmol), KJ (0.8 g, 5 mmol) and n-butanol (50 ml) was stirred at reflux for 72 h. After cooling to room temperature the solvent was evaporated, the residue was treated with water (200 ml) and extracted with CH$_2$Cl$_2$. Purification was carried out by flash chromatography, eluent—CH$_2$Cl$_2$:2N methanol NH$_3$ 96:4, it gave 3.5 g (86%) of compound 6(9).

Triethylamine (1.12 ml, 8.1 mmol) and Boc$_2$O (1.47 g, 6.7 mmol) one after another were added to a solution of ethyl 1-(phenylsulfonyl)-3-(piperazin-1-yl)indolizine-2-carboxylate 6(9) (2.77 g, 6.7 mmol) in CH$_2$Cl$_2$ (20 ml). The obtained mixture was stirred for 3 h, washed with saturated NaHCO$_3$ solution and saturated salt solution; dried over MgSO$_4$, evaporated to dryness at reduced pressure; it gave 3.38 g of compound 6(10), yield is nearly quantitative.

KOH (7.5 mmol) solution in water (10.5 ml) was added to a suspension of ethyl 3-(4-(tert-butoxycarbonyl)piperazin-1-yl)-1-(phenylsulfonyl)indolizine-2-carboxylate 6(10) (3.07 g, 6 mmol) in methanol (15 ml), the reaction mixture was stirred at 50° C. until complete solid dissolution (about 8 h), cooled, diluted with water and acidified with conc. HCl. Precipitated solid was filtered off, washed with water and dried, it gave 1.98 g (68%) of compound 6(11).

Diphenylphosphoryl azide (4 mmol) was added to a solution of 3-(4-(tert-butoxycarbonyl)piperazin-1-yl)-1-(phenylsulfonyl)indolizine-2-carboxylic acid 6(11) (1.94 g, 4 mmol) and triethylamine (4 mmol) in tert-butanol (28 ml) in inert gas current. The reaction mixture was boiled at stirring for 20 h, solvent was removed in vacuo, the residue was dissolved in benzene, washed with citric acid solution, water and saturated NaHCO$_3$ solution. Organic layer was separated, dried over Na$_2$SO$_4$, solvent was removed in vacuo, the residue was purified by flash-chromatography, eluent—benzene:ethyl acetate, 20:1, it gave 1.5 g (67%) of carbamate 6(12).

Sodium hydride (5.7 mol) as 60% suspension in mineral oil was added in portions to a solution of tert-butyl 4-(2-(tert-butoxycarbonylamino)-1-(phenylsulfonyl)indolizin-3-yl)piperazine-1-carboxylate 6(12) (1.46 g, 2.63 mmol) in THF (28 ml) in the inert gas current. After the reaction mixture was stirred at 20° C. for 1 h methyl iodide (1.1 g, 7.8 mmol) was added and stirring was continued at 40° C. for 12 h. Then, the mixture was diluted with water, solid was filtered off, washed with water and dried, it gave 1.2 g (80%) of compound 6(13).

Conc. HCl (3 ml) was added to a suspension of tert-butyl 4-(2-tert-butoxycarbonyl(methyl)amino)-1-(phenylsulfonyl)indolizin-3-yl)piperazine-1-carboxylate 6(13) (1.14 g, 2 mmol) in iso-propanol (12.5 ml) and the reaction mixture was stirred at 40° C. for 2 h, then solvent was removed in vacuo, the residue was neutralized by addition of NaHCO$_3$ water solution. The precipitated solid was filtered off, washed with water and dried, it gave 0.69 g (94%) of compound 1.4.1(7). LCMS (M+1) 371; $^1$H NMR (DMSO-D6, 400 MHz) δ 2.93 (m, 2H), 2.95 (d, J=13.35 Hz, 3H), 3.04 (m, 2H), 3.73 (m, 2H), 3.85 (m, 2H), 6.38 (t, J$_1$=7.0 Hz, J$_2$=1.25 Hz, 1H), 7.09 (t, J$_1$=9.50 Hz, J$_2$=1.18 Hz, 1H), 7.21 (m, 2H), 7.43 (m, 3H), 7.61 (m, 1H), 7.91 (d, J=1.18 Hz, 1H), 8.01 (d, J=7.53 Hz, 1H).

Compounds 1.4.1(8) and 1.4.1(9) were prepared according to analogous procedures starting from ethyl 1-(3-chlorophenylsulfonyl)indolizine-2-carboxylate and ethyl 1-(3-fluorophenylsulfonyl)indolizine-2-carboxylate, respectively;

methyl-[3-piperazin-1-yl-1-(3-chlorophenylsulfonyl)indolizin-2-yl]-amine 1.4.1(8), LCMS (M+1) 405; $^1$H NMR (DMSO-D6, 400 MHz) δ 2.93 (m, 2H), 2.95 (d, J=13.35 Hz, 3H), 3.06 (m, 2H), 3.73 (m, 2H), 3.84 (m, 2H), 6.39 (t, J$_1$=7.0 Hz, J$_2$=1.25 Hz, 1H), 7.09 (t, J$_1$=9.50 Hz, J$_2$=1.18 Hz, 1H), 7.21 (m, 2H), 7.40 (m, 3H), 7.53 (t, J$_1$=8.04 Hz, J$_2$=2.46 Hz, 1H), 7.92 (m, 1H), 8.01 (s, 1H); methyl-[3-piperazin-1-yl-1-(3-fluorophenylsulfonyl)indolizin-2-yl]-amine 1.4.1(9), LCMS (M+1) 389; $^1$H NMR (DMSO-D6, 400 MHz) δ 2.93 (m, 2H), 2.95 (d, J=13.35 Hz, 3H), 3.05 (m, 2H), 3.71 (m, 2H), 3.86 (m, 2H), 6.40 (t, J$_1$=7.0 Hz, J$_2$=1.25 Hz, 1H), 7.09 (t, J$_1$=9.50 Hz, J$_2$=1.18 Hz, 1H), 7.21 (m, 1H), 7.29 (m, 1H), 7.41 (t, J$_1$=8.24 Hz, J$_2$=0.51 Hz, 1H), 7.76 (d, J=1.74 Hz, 1H), 7.85 (t, J$_1$=7.53 Hz, J$_2$=1.74 Hz, 1H), 7.93 (d, J=1.18 Hz, 1H).

Compounds 1.4.1(10)-1.4.1(12) were prepared according to analogous procedures using 2-chloro-N-(2-chloroethyl)-N-methylethylamine:

methyl-[3-(4-methylpiperazin-1-yl)-1-phenylsulfonylindolizin-2-yl]-amine 1.4.1(10), LCMS (M+1) 385; $^1$H NMR (DMSO-D6, 400 MHz) δ 2.32 (d, J=13.35 Hz, 3H), 2.51 (m, 2H), 3.05 (m, 2H), 2.62 (m, 2H), 2.95 (d, J=13.35 Hz, 3H), 4.11 (m, 2H), 4.21 (m, 2H), 6.39 (t, J$_1$=7.0 Hz, J$_2$=1.25 Hz, 1H), 7.09 (t, J$_1$=9.50 Hz, J$_2$=1.18 Hz, 1H), 7.44 (m, 2H), 7.60 (d, J=7.58 Hz, 1H), 7.91 (d, J=7.58 Hz, 1H), 7.91 (d, J=1.18 Hz, 1H), 8.00 (t, J$_1$=7.53 Hz, J$_2$=1.25 Hz, 1H); methyl-[3-(4-methylpiperazin-1-yl)-1-(3-chlorophenylsulfonylindolizin-2-yl]-amine 1.4.1(11), LCMS (M+1) 419; $^1$H NMR (DMSO-D6, 400 MHz) δ 2.32 (d, J=13.35 Hz, 3H), 2.55 (m, 2H), 2.61 (m, 2H), 2.95 (d, J=13.35 Hz, 3H), 4.15 (m, 2H), 4.22 (m, 2H), 6.39 (t, J$_1$=7.0 Hz, J$_2$=1.25 Hz, 1H), 7.07 (t, J$_1$=9.50 Hz, J$_2$=1.18 Hz, 1H), 7.40 (m, 2H), 7.53 (t, J$_1$=8.04 Hz, J$_2$=2.46 Hz, 1H), 7.93 (m, 2H), 8.05 (d, J=2.46 Hz, 1H); methyl-[3-(4-methylpiperazin-1-yl)-1-(3-fluorophenylsulfonylindolizin-2-yl]-amine 1.4.1(12), LCMS (M+1) 403; $^1$H NMR (DMSO-D6, 400 MHz) δ 2.32 (m, 3H), 2.51 (m, 2H), 2.62 (m, 2H), 2.95 (d, J=13.35 Hz, 3H), 4.14 (m, 2H), 4.21 (m, 2H), 6.39 (t, J$_1$=7.0 Hz, J$_2$=1.25 Hz, 1H), 7.09 (t, J$_1$=9.50 Hz, J$_2$=1.18 Hz, 1H), 7.27 (m, 1H), 7.41 (t, J$_1$=8.24 Hz, J$_2$=0.51 Hz, 1H), (m, 2H), 7.75 (d, J=1.74 Hz, 1H), 7.86 (t, J$_1$=7.53 Hz, J$_2$=1.74 Hz, 1H), (m, 2H), 7.93 (d, J=1.18 Hz, 1H).

Compounds 1.4.2(1)-1.4.2(3) were prepared starting from 2-(chloromethyl)-6-methylpyridine according to the method given in example 7 and scheme 7:

methyl-(5-methyl-1-phenylsulfonylindolizin-2-yl)-amine 1.4.2(1), LCMS (M+1) 301; $^1$H NMR (DMSO-D6, 400 MHz) δ 2.38 (t, J$_1$=2.88 Hz, J$_2$=0.38 Hz, 3H), 2.98 (d, J=13.35 Hz, 3H), 6.17 (t, J$_1$=7.0 Hz, J$_2$=1.25 Hz, 1H), 7.30 (d, J=9.50 Hz, 1H), 7.50 (m, 2H), 7.61 (d, J=7.58 Hz, 3H), 7.89 (t, J$_1$=9.50 Hz, J$_2$=1.25 Hz, 1H), 8.02 (m, 2H), 9.37 (s, 1H); methyl-[5-methyl-1-(3-chlorophenylsulfonyl)indolizin-2-yl]-amine 1.4.2(2), LCMS (M+1) 335; $^1$H NMR (DMSO-D6, 400 MHz) δ 2.38 (t, J$_1$=2.88 Hz, J$_2$=0.38 Hz, 3H), 2.98 (d, J=13.35 Hz, 3H), 6.17 (t, J$_1$=7.0 Hz, J$_2$=1.25 Hz, 1H), 7.29 (d, J=9.50 Hz, 1H), 7.37 (t, J$_1$=8.04 Hz, J$_2$=0.51 Hz, 1H), 7.53 (t, J$_1$=8.04 Hz, J$_2$=1.69 Hz, 1H), 7.90 (m, 2H), 8.02 (s, 1H), 9.37 (s, 1H); methyl-[5-methyl-1-(3-fluorophenylsulfonyl)indolizin-2-yl]-amine 1.4.2(3), LCMS (M+1) 319; $^1$H NMR (DMSO-D6, 400 MHz) δ 2.38 (t, J$_1$=2.88 Hz, J$_2$=0.38 Hz, 3H), 2.98 (d, J=13.35 Hz, 3H), 6.17 (t, J$_1$=7.0 Hz, J$_2$=1.25 Hz, 1H), 7.29 (m, 2H), 7.42 (t, J$_1$=8.24 Hz, J$_2$=0.51 Hz, 1H), 7.74 (d, J=1.74 Hz, 1H), 7.87 (m, 2H), 8.02 (m, 1H), 9.37 (s, 1H).

For the synthesis of compounds 1.4.2(4)-1.4.2(9) 2-(chloromethyl)-6-fluoropyridine was used as a starting material, which as a result of transformations described in example 7 was converted into 5-fluoro-N-methyl-1-(phenylsulfonyl)indolizine-2-amine, the latest at the interaction with Boc-piperazine and subsequent deprotection, by analogy with transformations described in example 14, gave corresponding compounds 1.4.2(4)-1.4.2(6), and interaction with N-methylpiperazine gave compounds 1.4.2(7)-1.4.2(9).

Methyl-(5-piperazin-1-yl-1-phenylsulfonylindolizin-2-yl)-amine 1.4.2(4), LCMS (M+1) 371; $^1$H NMR (DMSO-D6, 400 MHz) δ 2.93 (m, 2H), 2.98 (s, 3H), 3.04 (m, 2H), 3.37 (m, 2H), 3.51 (m, 2H), 5.96 (m, 2H), 6.14 (t, J$_1$=7.30 Hz, J$_2$=1.56 Hz, 1H), 7.08 (d, J=7.30 Hz, 1H), 7.47 (m, 3H), 7.60 (t, J$_1$=7.58 Hz, J$_2$=1.25 Hz, 1H), 8.01 (t, J$_1$=2.15 Hz, J$_2$=1.25 Hz, 1H), 8.34 (s, 1H); methyl-[5-piperazin-1-yl-1-(3-chlorophenylsulfonyl)indolizin-2-yl]-amine 1.4.2(5), LCMS (M+1) 405; $^1$H NMR (DMSO-D6, 400 MHz) δ 2.91 (m, 2H), 2.98 (d, J=13.35 Hz, 3H), 3.01 (m, 2H), 3.40 (m, 2H), 3.47 (m, 2H), 5.96 (m, 2H), 6.16 (t, J$_1$=7.30 Hz, J$_2$=1.56 Hz, 1H), 7.07 (d, J=7.30 Hz, 1H), 7.40 (m, 2H), 7.53 (t, J$_1$=8.04 Hz, J$_2$=1.69 Hz, 1H), 7.95 (t, J$_1$=2.46 Hz, J$_2$=1.69 Hz, 1H), 8.04 (t, J$_1$=2.46 Hz, J$_2$=0.51 Hz, 1H), 8.34 (s, 1H); methyl-[5-piperazin-1-yl-1-(3-fluorophenylsulfonyl)indolizin-2-yl]-amine 1.4.2(6), LCMS (M+1) 389; $^1$H NMR (DMSO-D6, 400 MHz) δ 2.91 (m, 2H), 2.98 (d, J=13.35 Hz, 3H), 3.04 (m, 2H), 3.37 (m, 2H), 3.50 (m, 2H), 5.96 (m, 2H), 6.15 (t, J$_1$=7.30 Hz, J$_2$=1.56 Hz, 1H), 7.08 (t, J$_1$=9.50 Hz, J$_2$=7.30 Hz, 1H), 7.29 (t, J$_1$=8.24 Hz, J$_2$=1.74 Hz, 1H), 7.44 (t, J$_1$=8.24 Hz, J$_2$=0.51 Hz, 1H), 7.74 (t, J$_1$=1.74 Hz, J$_2$=0.51 Hz, 1H), 7.83 (d, J=1.74 Hz, 1H), 8.34 (s, 1H); methyl-[5-(4-methylpiperazin-1-yl)-1-phenylsulfonylindolizin-2-yl]-amine 1.4.2(7), LCMS (M+1) 385; $^1$H NMR (DMSO-D6, 400 MHz) δ 2.32 (s, 3H), 2.52 (m, 2H), 2.62 (m, 2H), 2.98 (d, J=13.35 Hz, 3H), 3.76 (m, 2H), 3.89 (m, 2H), 6.15 (t, J$_1$=7.30 Hz, J$_2$=1.56 Hz, 1H), 7.07 (t, J$_1$=9.50 Hz, J$_2$=7.30 Hz, 1H), 7.46 (m, 3H), 7.62 (t, J$_1$=7.58 Hz, J$_2$=1.25 Hz, 1H), 8.02 (t, J$_1$=2.15 Hz, J$_2$=0.55 Hz, 1H), 8.34 (s, 1H), 9.37 (s, 1H); methyl-[5-(4-methylpiperazin-1-yl)-1-(3-chlorophenylsulfonyl)indolizin-2-yl]-amine 1.4.2(8), LCMS (M+1) 419; $^1$H NMR (DMSO-D6, 400 MHz) δ 2.32 (m, 3H), 2.54 (m, 2H), 2.61 (m, 2H), 2.98 (d, J=13.35 Hz, 3H), 3.80 (m, 2H), 3.87 (m, 2H), 6.14 (m, 1H), 7.08 (d, J=7.30 Hz, 1H), 7.41 (m, 2H), 7.51 (t, $J_1$=8.04 Hz, $J_2$=1.69 Hz, 1H), 7.96 (t, $J_1$=7.53 Hz, $J_2$=2.46 Hz, 1H), 8.03 (t, $J_1$=2.46 Hz, $J_2$=0.51 Hz, 1H), 8.34 (s, 1H), 9.37 (s, 1H); methyl-[5-(4-methylpiperazin-1-yl)-1-(3-fluorophenylsulfonyl)indolizin-2-yl]-amine 1.4.2(9), LCMS (M+1) 403; $^1$H NMR (DMSO-D6, 400 MHz) δ 2.32 (m, 3H), 2.51 (m, 2H), 2.59 (m, 2H), 2.98 (d, J=13.35 Hz, 3H), 3.80 (m, 2H), 3.88 (m, 2H), 6.16 (t, $J_1$=7.30 Hz, $J_2$=1.56 Hz, 1H), 7.08 (t, $J_1$=9.50 Hz, $J_2$=7.30 Hz, 1H), 7.24 (t, $J_1$=8.24 Hz, $J_2$=1.69 Hz, 1H), (m, 2H), 7.41 (m, 1H), 7.77 (t, $J_1$=1.74 Hz, $J_2$=0.51 Hz, 1H), 7.86 (d, J=1.74 Hz, 1H), 8.34 (s, 1H) 9.37 (s, 1H).

EXAMPLE 10

Synthesis of methyl-(3-phenylsulfonyl-8-fluoro-quinolin-4-yl)-amine 1.5(8). Scheme 10

2-Fluoroaniline 7(1) (3.82 g, 0.0344 mol) and methyl 2-phenylsulfonyl-3-ethoxy-acrylate 7(2) (9.59 g, 0.0355 mol) were mixed together in biphenyl ether (21.5 ml). The mixture was stirred in an opened flask for 6 h at 250-270° C. Ethanol was distilled during the first 30 min. After the reaction was completed (LCMS control) the mixture was cooled, the formed solid was filtered off, dissolved in ethanol and solution was boiled with charcoal. After filtration from charcoal ethanol was evaporated, the residue was subjected to chromatography on silica, eluent—gradient of solvent system $CHCl_3$:ethyl acetate=from 10:1 to 5:1. The residue after evaporation of fractions, comprising the final product was washed with ether, it gave 345 mg (3.3%) of 4-hydroxy-3-phenylsulfonyl-8-fluoroquinoline 7(3).

Compound 7(3) (340 mg, 1.12 mmol) was mixed with oxalyl chloride (1.92 ml, 2.84 g, 22.4 mmol) in $CHCl_3$ (12 ml). The mixture was refluxed for 3 h. The completeness of the reaction was controlled by TLC (solvent system is $CH_2Cl_2$: ethyl acetate=5:1, $R_f$=0.8). After the reaction was completed the excess of oxalyl chloride and $CHCl_3$ were distilled in vacuo. The residue was washed with ether, it gave 310 mg (85%) of 3-phenylsulfonyl-8-fluoro-4-chloroquinoline 7(4).

A solution of methylamine in THF (835 mkl, 1.99 mmol) (conc. 74 mg/ml) was added to a suspension of compound 7(4) (305 mg, 0.949 mmol) in THF (6.1 ml). The reaction was carried out at 20° C. at stirring for 12 h (LCMS control). After it was completed the formed solid was filtered off, dissolved in $CH_2Cl_2$, washed with water, dried over $Na_2SO_4$ and evaporated, it gave 250 mg (83%) of methyl-(3-phenylsulfonyl-8-fluoroquinolin-4-yl)-amine 1.5(8): LCMS (M+1) 317; $^1$H NMR ($CDCl_3$, 400 MHz) δ 9.04 (s, 1H), 8.05 (d, J=8.0 Hz, 1H), 7.93 (d, J=7.6 Hz, 2H), 7.8 (br.s, 1H), 7.59 (m, 1H), 7.52 (m, 2H), 7.42 (m, 1H), 7.34 (m, 1H), 3.45 (d, J=5.2 Hz, 3H).

EXAMPLE 11

Synthesis of methyl-(8-piperazin-1-yl-3-phenylsulfonylquinolin-4-yl)-amine dihydrochloride 1.5(1).2HCl. Scheme 10

Compound 1.5(8) (210 mg, 0.665 mmol) and piperazine (572 mg, 6.65 mmol) were dissolved in sulpholane (7.5 ml). The reaction was carried out at 180° C. for 14 h (LCMS control). After it was completed the reaction mass was mixed with water, the product was extracted with $CH_2Cl_2$, extract was dried over $Na_2SO_4$ and evaporated. Further purification was carried out by HPLC method, it gave 172 mg of the product in the form of trifluoroacetate, which was dissolved in acetone (5 ml) and dihydrochloride was precipitated by 180 mkl of HCl solution in dioxane (3M). It gave 103 mg (66%) of methyl-(8-piperazin-1-yl-3-phenylsulfonylquinolin-4-yl)-amine dihydrochloride 1.5(1).2HCl: LCMS (M+1) 383; $^1$H NMR (DMSO-$d_6$, 400 MHz) δ 9.46 (br.s, 2H), 8.91 (s, 1H), 8.40 (d, J=7.6 Hz, 1H), 8.14 (d, J=6.8 Hz, 2H), 7.82 (t, J=7.2 Hz, 1H), 7.78 (d, J=7.2 Hz, 1H), 7.68 (m, 3H), 3.49 (br.m, 7H), 3.20 (br.m, 4H).

Compounds 1.5(2)-1.5(6) were prepared in analogous manner starting from methyl 2-(3-chlorophenylsulfonyl)-3-ethoxy-acrylate and methyl 2-(3-fluorophenylsulfonyl)-3-ethoxy-acrylate, and also N-methylpiperazine; methyl-[8-piperazin-1-yl-3-(3-chlorophenylsulfonyl)quinolin-4-yl]-amine 1.5(2), LCMS (M+1) 417; $^1$H NMR (DMSO-D6, 400 MHz) δ 3.06 (m, 2H), 3.14 (m, 2H), 3.42 (m, 2H), 3.50 (m, 2H), 3.69 (d, J=13.35 Hz, 3H), 5.85 (m, 2H), 6.54 (t, $J_1$=7.80 Hz, $J_2$=1.46 Hz, 1H), 6.94 (d.d, $J_1$=7.90 Hz, $J_2$=0.28 Hz, 1H), 7.38 (t, $J_1$=8.04 Hz, $J_2$=0.51 Hz, 1H), 7.52 (d.d, $J_1$=8.04 Hz, $J_2$=2.46 Hz, 1H), 7.92 (t, $J_1$=7.53 Hz, $J_2$=1.69 Hz, 1H), 8.01 (d, $J_2$=2.46 Hz, 1H), 8.15 (d, J=7.90 Hz, 1H), 8.78 (s, 1H); methyl-[8-piperazin-1-yl-3-(3-fluorophenylsulfonyl)quinolin-4-yl]-amine 1.5(3), LCMS (M+1) 401; $^1$H NMR (DMSO-D6, 400 MHz) δ 3.06 (m, 2H), 3.14 (m, 2H), 3.42 (m, 2H), 3.50 (m, 2H), 3.69 (d, J=13.35 Hz, 3H), 5.85 (m, 2H), 6.53 (t, $J_1$=7.80 Hz, $J_2$=1.46 Hz, 1H), 6.96 (d.d, $J_1$=7.90 Hz, $J_2$=0.28 Hz, 1H), 7.27 (m, 1H), 7.42 (d.d, $J_1$=8.24 Hz, $J_2$=0.51 Hz, 1H), 7.71 (d, J=1.74 Hz, 1H), 7.82 (t, $J_1$=7.53 Hz, $J_2$=1.69 Hz, 1H), 8.16 (t, $J_1$=7.90 Hz, $J_2$=1.46 Hz, 1H), 8.84 (s, 1H); methyl-[8-(4-methylpiperazin-1-yl)-3-phenylsulfonylquinolin-4-yl]-amine 1.5(4), LCMS (M+1) 397; $^1$H NMR (DMSO-D6, 400 MHz) δ 2.28 (t, $J_1$=13.35 Hz, $J_2$=0.99 Hz, 3H), 2.54 (m, 2H), 2.61 (m, 2H), 3.40 (m, 2H), 3.48 (m, 2H), 3.69 (d, J=13.35 Hz, 3H), 6.55 (t, $J_1$=7.80 Hz, $J_2$=1.46 Hz, 1H), 6.94 (d.d, $J_1$=7.90 Hz, $J_2$=0.28 Hz, 1H), 7.47 (m, 2H), 7.60 (d.d, $J_1$=7.58 Hz, $J_2$=1.25 Hz, 1H), 7.97 (t, $J_1$=7.53 Hz, $J_2$=1.25 Hz, 1H), 8.16 (m, 1H), 8.82 (s, 1H), 9.04 (s, 1H); methyl-[8-(4-methylpiperazin-1-yl)-3-(3-chlorophenylsulfonyl)quinolin-4-yl]-amine 1.5(5), LCMS (M+1) 431; $^1$H NMR (DMSO-D6, 400 MHz) δ 2.28 (t, $J_1$=13.35 Hz, $J_2$=0.99 Hz, 3H), 2.55 (m, 2H), 2.62 (m, 2H), 3.43 (m, 2H), 3.52 (m, 2H), 3.69 (d, J=13.35 Hz, 3H), 6.55 (t, $J_1$=7.80 Hz, $J_2$=1.46 Hz, 1H), 6.96 (d.d, $J_1$=7.90 Hz, $J_2$=0.28 Hz, 1H), 7.38 (t, $J_1$=8.04 Hz, $J_2$=0.51 Hz, 1H), 7.53 (d.d, $J_1$=8.04 Hz, $J_2$=2.46 Hz, 1H), 7.93 (t, $J_1$=7.53 Hz, $J_2$=1.69 Hz, 1H), 8.02 (s, 1H), 8.16 (t, $J_1$=7.90 Hz, $J_2$=1.46 Hz, 1H), 8.78 (s, 1H), 9.04 (s, 1H); methyl-[8-(4-methylpiperazin-1-yl)-3-(3-fluorophenylsulfonyl)quinolin-4-yl]-amine 1.5(6), LCMS (M+1) 415; $^1$H NMR (DMSO-D6, 400 MHz) δ 2.28 (t, $J_1$=13.35 Hz, $J_2$=0.99 Hz, 3H), 2.55 (m, 2H), 2.63 (m, 2H), 3.43 (m, 2H), 3.52 (m, 2H), 3.69 (d, J=13.35 Hz, 3H), 6.55 (t, $J_1$=7.80 Hz, $J_2$=1.46 Hz, 1H), 6.94 (d.d, $J_1$=7.90 Hz, $J_2$=0.28 Hz, 1H), 7.27 (t, $J_1$=8.61 Hz, $J_2$=1.74 Hz, 1H), 7.42 (d.d, $J_1$=8.24 Hz, $J_2$=0.51 Hz, 1H), 7.71 (t, $J_1$=12.08 Hz, $J_2$=1.74 Hz, 1H), 7.82 (d, J=7.53 Hz, 1H), 8.14 (m, 1H), 8.84 (s, 1H), 9.04 (s, 1H).

EXAMPLE 12

Synthesis of methyl-(3-phenylsulfonylquinolin-4-yl)-amine 1.5(7). Scheme 11

4-Hydroxyquinoline 8(4) was prepared from aniline 8(1) according to the method described in *J. Org. Chem.* 2000, 23, 8005, 3-bromo-4-hydroxyquinoline 8(5)—according to the procedure given in *J. Am. Chem. Soc.* 1946, 1229-1231.

A solution of compound 8(5) (3.01 g, 0.135 mol) and K thiophenolate 2(2) (2 g, 0.135 mol) in dimethyl sulfoxide (40 ml) was heated at 120° C. in a microwave oven for 3 h. After the reaction was completed the mixture was poured into water, precipitated solid was filtered off. The product was isolated by means of column chromatography (eluent—ethyl acetate:hexane 7:3). It gave 1.55 g (45%) of 3-phenylthio-quinolin-4-ol 8(6).

A solution of compound 8(6) (1.4 g, 5.55 mmol) and perhydrol (3.78 ml, 33.3 mmol) in AcOH (60 ml) was stirred at 75° C. for 12 h. Then, the reaction mixture was cooled, water was added, precipitated solid was filtered off, it gave 1.32 g (83%) of 3-(phenylsulfonyl)quinoline-4-ol 8(7).

A solution of compound 8(7) (0.85 g, 3 mmol) in POCl$_3$ (3 ml) was heated on a water bath for 0.5 h, cooled, poured onto water, aqua ammonia (5 ml) was added. The product was extracted with ether and after the appropriate treatment it was recrystallized from hexane. It gave 0.86 g (88.8%) of 4-chloro-3-(phenylsulfonyl)quinoline 8(8).

A mixture of compound 8(8) (600 mg, 2 mmol), 20% methylamine solution (320 mg, 2 mmol), triethylamine (280 mkl) in iso-propanol (20 ml) was refluxed for 12 h, cooled, the precipitated solid was filtered off, it gave 280 mg (46.9%) of methyl-(3-phenylsulfonylquinolin-4-yl)-amine 1.5(7): LCMS (M+1) 299; $^1$H NMR (CDCl$_3$, 400 MHz) □ 9.01 (s, 1H), 8.26 (d, J=8 Hz, 1H), 7.94 (m, 3H), 7.73 (t, J=7.6 Hz, 2H), 7.67 (br.s., 1H), 7.59 (t, J=7.6 Hz, 1H), 7.51 (t, J=7.6 Hz, 2H), 7.42 (t, J=7.6 Hz, 1H), 3.45 (d, J=5.6 Hz, 3H).

EXAMPLE 13

The General Method for Preparation of Substituted methyl-(8-piperazin-1-yl-5-phenylsulfonylquinolin-6-yl)-amines 1.6(1-6). Scheme 12

A solution of 5,8-dichloro-6-nitroquinoline 13(1) (6.02 g, 0.0248 mol) and Na phenylsulfinate 4(2) (4.06 g, 0.0248 mol) in DMF (100 ml) was stirred at 120° C. for 12 h. The reaction mixture was cooled, poured into water and extracted with ethyl acetate. Organic layer was dried over Na$_2$SO$_4$, filtered and evaporated to dryness under reduced pressure. The mixture was separated by means of column chromatography on silica, eluent—ethyl acetate:hexane 1:4, it gave 3.8 g (43.8%) of compound 13(2).

A solution of 8-chloro-6-nitro-5-(phenylsulfonyl)quinoline 13(2) (3.46 g, 9.93 mmol) and Boc-piperazine (18.45 g, 0.099 mol, 10 eq.) in sulfolane (11.25 ml) was stirred at 180° C. for 4 h. Completeness of the reaction was controlled by LCMS method. After the reaction was over the mixture was mixed with water, the product was extracted with CH$_2$Cl$_2$, the extract was dried over Na$_2$SO$_4$ and evaporated under reduced pressure. Further purification was carried out by HPLC method, it gave 3.27 g (66%) of compound 13(3) as trifluoroacetate. The prepared tert-butyl 4-(6-nitro-5-(phenylsulfonyl)quinolin-8-yl)piperazine-1-carboxylate 13(3) was reduced by Fe.

Fe powder (2.85 g, 0.051 mol) was added in small portions to agitated suspension of compound 13(3) (5.06 g, 0.01 mol) in AcOH (33 ml). The reaction mixture was stirred at 70° C. for 3 h, cooled, diluted with water; the precipitated solid was filtered off, it gave 3 g (63%) of compound 13(4).

A mixture of tert-butyl 4-(6-amino-5-(phenylsulfonyl) quinolin-8-yl)piperazine-1-carboxylate 13(4) (2.8 g, 6 mmol) and formic acid (3 ml) was refluxed for 1 h and evaporated at reduced pressure. CHCl$_3$ was added to the residue, the solution was washed with 10% NaHCO$_3$ water solution. Organic layer was separated, dried over Na$_2$SO$_4$, filtered and evaporated to dryness. The product was recrystallized from hexane, it gave 2.54 g (90.5%) of compound 13(5).

Conc. HCl (6 ml) was added to a suspension of tert-butyl 4-(6-formamido-5-(phenylsulfonyl)quinolin-8-yl)piperazine-1-carboxylate 13(5) (1.98 g, 4 mmol) in iso-propanol (25 ml) and the reaction mixture was stirred at 40° C. for 2 h, the solvent was removed in vacuo, the residue was neutralized with NaHCO$_3$ water solution. The precipitated solid was filtered off, washed with water and dried, it gave 1.49 g (94%) of compound 13(6) (R'$_2$=H).

Borane-methyl sulfide complex (3.3 ml, 6.6 mmol, 2M) was added to a mixture of N-(5-(phenylsulfonyl)-8-(piperazin-1-yl)quinolin-6-yl)formamide 13(6) (0.87 g, 2.2 mmol) in anhydrous THF (17 ml) and the resultant mixture was stirred for 12 h at 20° C. Then saturated NaHCO$_3$ solution was added and mixture was extracted with CH$_2$Cl$_2$. Organic layer was separated, dried over Na$_2$SO$_4$, filtered and evaporated to dryness under reduced pressure. The final product was recrystallized from ethyl acetate, it gave 0.55 g (64.9%) of compound 1.6(1). LCMS (M+1) 383; $^1$H NMR (DMSO-D6, 400 MHz) δ 2.80 (t, J$_1$=13.35 Hz, J$_2$=0.39 Hz, 3H), 3.05 (m, 2H), 3.14 (m, 2H), 3.41 (m, 2H), 3.51 (m, 2H), 6.02 (m, 2H), 6.49 (s, 1H), 7.39 (m, 2H), 7.61 (m, 2H), 7.78 (t, J$_1$=8.61 Hz, J$_2$=1.11 Hz, 1H), 7.93 (d, J=7.53 Hz, 2H), 8.11 (d, J=4.43 Hz, 1H).

Compounds 1.6(2)-1.6(6) were prepared in analogous manner using 3-chloro- and 3-fluoro-substituted Na phenylsulfinate (R$^1$=Cl, F), and also N-methylpiperazine; methyl-[8-piperazin-1-yl-5-(3-chlorophenylsulfonyl)quinolin-6-yl]-amine 1.6(2), LCMS (M+1) 417; $^1$H NMR (DMSO-D6, 400 MHz) δ 2.80 (t, J$_1$=13.35 Hz, J$_2$=0.39 Hz, 3H), 3.06 (m, 2H), 3.14 (m, 2H), 3.42 (m, 2H), 3.51 (m, 2H), 6.02 (m, 2H), 6.49 (s, 1H), 7.28 (t, J$_1$=8.04 Hz, J$_2$=0.51 Hz, 1H), 7.52 (d, J=2.46 Hz, 1H), 7.59 (t, J$_1$=8.61 Hz, J$_2$=0.28 Hz, 1H), 7.78 (t, J$_1$=8.61 Hz, J$_2$=1.11 Hz, 1H), 7.86 (t, J$_1$=7.53 Hz, J$_2$=1.69 Hz, 1H), 7.95 (s, 1H), 8.11 (d, J=2.46 Hz, 1H); methyl-[8-piperazin-1-yl-5-(3-fluorophenylsulfonyl)quinolin-6-yl]-amine 1.6(3), LCMS (M+1) 401; $^1$H NMR (DMSO-D6, 400 MHz) δ 2.80 (t, J$_1$=13.35 Hz, J$_2$=0.39 Hz, 3H), 3.06 (m, 2H), 3.14 (m, 2H), 3.42 (m, 2H), 3.50 (m, 2H), 6.02 (m, 2H), 6.49 (s, 1H), 7.27 (d, J=1.74 Hz, 1H), 7.32 (t, J$_1$=8.24 Hz, J$_2$=0.51 Hz, 1H), 7.60 (t, J$_1$=8.61 Hz, J$_2$=0.28 Hz, 1H), 7.67 (t, J$_1$=12.08 Hz, J$_2$=1.74 Hz, 1H), 7.78 (m, 2H); methyl-[8-(4-methylpiperazin-1-yl)-5-phenylsulfonylquinolin-6-yl]-amine 1.6(4), LCMS (M+1) 397; $^1$H NMR (DMSO-D6, 400 MHz) δ 2.28 (t, J$_1$=13.35 Hz, J$_2$=0.99 Hz, 3H), 2.52 (m, 2H), 2.63 (m, 2H), 2.80 (t, J$_1$=13.35 Hz, J$_2$=0.39 Hz, 3H), 3.42 (m, 2H), 3.53 (m, 2H), 6.50 (s, 1H), 7.38 (d.d, J$_1$=7.53 Hz, J$_2$=1.47 Hz, 1H), 7.60 (m, 2H), 7.79 (t, J$_1$=8.61 Hz, J$_2$=1.11 Hz, 1H), 7.92 (d, J=7.53 Hz, 2H), 8.11 (d, J=4.43 Hz, 1H), 9.38 (s, 1H); methyl-[8-(4-methylpiperazin-1-yl)-5-(3-chlorophenylsulfonyl)quinolin-6-yl]-amine 1.6(5), LCMS (M+1) 431; $^1$H NMR (DMSO-D6, 400 MHz) δ 2.28 (t, J$_1$=13.35 Hz, J$_2$=0.99 Hz, 3H), 2.55 (m, 2H), 2.63 (m, 2H), 2.80 (t, J$_1$=13.35 Hz, J$_2$=0.39 Hz, 3H), 3.44 (m, 2H), 3.51 (m, 2H), 6.50 (s, 1H), 7.28 (d.d, J$_1$=8.04 Hz, J$_2$=0.51 Hz, 1H), 7.52 (d, J=2.46 Hz, 1H), 7.59 (t, J$_1$=8.61 Hz, J$_2$=4.43 Hz, 1H), 7.78 (t, J$_1$=8.61 Hz, J$_2$=1.11 Hz, 1H), 7.86 (t, J$_1$=7.53 Hz, J$_2$=2.46 Hz, 1H), 7.96 (d, J=2.46 Hz, 1H), 8.11 (d, J=4.43 Hz, 1H), 9.38 (s, 1H); methyl-[8-(4-methylpiperazin-1-yl)-5-(3-fluorophenylsulfonyl)quinolin-6-yl]-amine 1.6(6), LCMS (M+1) 415; $^1$H NMR (DMSO-D6, 400 MHz) δ 2.28 (t, J$_1$=13.35 Hz, J$_2$=0.99 Hz, 3H), 2.52 (m, 2H), 2.63 (m, 2H), 2.80 (t, J$_1$=13.35 Hz, J$_2$=0.39 Hz, 3H), 3.44 (m, 2H), 3.51 (m, 2H), 6.49 (s, 1H), 7.25 (d, J=1.74 Hz, 1H), 7.32 (t, J$_1$=8.24 Hz, J$_2$=0.51 Hz, 1H), 7.59 (t, J$_1$=8.61 Hz, J$_2$=4.43 Hz, 1H), 7.66 (m, 1H), 7.77 (m, 2H), 8.11 (d, J=4.43 Hz, 1H), 9.38 (s, 1H).

EXAMPLE 14

The General Method for Preparation of Substituted methyl-(8-piperazin-1-yl-4-phenylsulfonylquinolin-3-yl)-amines 1.7(1-6). Scheme 13

A solution of 4-chloro-8-fluoro-3-nitroquinoline 14(1) (4.53 g, 0.02 mol) and Na phenylsulfinate 4(2) (3.28 g, 0.02 mol) in DMF (80 ml) was stirred at 120° C. for 12 h. The reaction mixture was cooled, poured into water and extracted with ethyl acetate. Organic layer was dried over $Na_2SO_4$, filtered and evaporated to dryness under reduced pressure. The mixture was separated by means of column chromatography on silica, eluent—ethyl acetate:hexane 1:4, it gave 2.91 g (43.8%) of compound 14(2).

A solution of 8-fluoro-3-nitro-4-(phenylsulfonyl)quinoline 14(2) (2.19 g, 6.62 mmol) and Boc-piperazine (12.3 g, 0.066 mol, 10 eq.) in sulfolane (7.5 ml) was stirred at 180° C. for 4 h. Completeness of the reaction was controlled by LCMS method. After the reaction was over the mixture was mixed with water, the product was extracted with $CH_2Cl_2$, extract was dried over $Na_2SO_4$ and evaporated under reduced pressure. Further purification was carried out by HPLC method, it gave 2.7 g (66%) of compound 14(3) as trifluoroacetate. The prepared tert-butyl 4-(3-nitro-4-(phenylsulfonyl)quinolin-8-yl)piperazine-1-carboxylate 14(3) was reduced by Fe.

Fe powder (1.34 g, 0.0238 mol) was added in small portions to agitated suspension of compound 14(3) (2.37 g, 0.0047 mol) in AcOH (15.5 ml). The reaction mixture was stirred at 70° C. for 3 h, cooled, diluted with water; the precipitated solid was filtered off, it gave 1.4 g (63%) of compound 14(4).

A mixture of tert-butyl 4-(3-amino-4-(phenylsulfonyl) quinolin-8-yl)piperazine-1-carboxylate 14(4) (1.4 g, 3 mmol) and formic acid (1.5 ml) was refluxed for 1 h and evaporated under reduced pressure. $CHCl_3$ was added to the residue, the solution was washed with 10% $NaHCO_3$ water solution. Organic layer was separated, dried over $Na_2SO_4$, filtered and evaporated to dryness. The product was recrystallized from hexane, it gave 1.27 g (90.5%) of compound 14(5).

Conc. HCl (4 ml) was added to a suspension of tert-butyl 4-(3-formamido-4-(phenylsulfonyl)quinolin-8-yl)piperazine-1-carboxylate 14(5) (1.23 g, 2.47 mmol) in iso-propanol (15.5 ml) and the reaction mixture was stirred at 40° C. for 2 h, the solvent was removed in vacuo, the residue was neutralized with $NaHCO_3$ water solution. The precipitated solid was filtered off, washed with water and dried, it gave 0.91 g (94%) of compound 14(6) (R'$_2$=H).

Borane-methyl sulfide complex (3.3 ml, 6.6 mmol, 2M) was added to a mixture of N-(4-(phenylsulfonyl)-8-(piperazin-1-yl)quinolin-3-yl)formamide 14(6) (0.87 g, 2.2 mmol) in anhydrous THF (17 ml) and the resultant mixture was stirred for 12 h at 20° C. Then $NaHCO_3$ saturated solution was added and mixture was extracted with $CH_2Cl_2$. Organic layer was separated, dried over $Na_2SO_4$, filtered and evaporated to dryness under reduced pressure. The final product was recrystallized from ethyl acetate, it gave 0.55 g (64.9%) of compound 1.7(1). LCMS (M+1) 383; $^1$H NMR (DMSO-D6, 400 MHz) δ 2.98 (t, $J_1$=13.35 Hz, $J_2$=0.39 Hz, 3H), 3.07 (m, 2H), 3.14 (m, 2H), 3.41 (m, 2H), 3.50 (m, 2H), 5.26 (m, 2H), 6.63 (t, $J_1$=7.80 Hz, $J_2$=1.46 Hz, 1H), 7.22 (d.d, $J_1$=8.16 Hz, $J_2$=0.28 Hz, 1H), 7.38 (t, $J_1$=7.58 Hz, $J_2$=1.47 Hz, 2H), 7.55 (s, 1H), 7.61 (t, $J_1$=7.58 Hz, $J_2$=1.25 Hz, 1H), 7.79 (d, J=0.16 Hz, 1H), 7.94 (t, $J_1$=7.53 Hz, $J_2$=1.25 Hz, 2H).

Compounds 1.7(2)-1.7(6) were prepared in analogous manner using 3-chloro- and 3-fluoro-substituted Na phenylsulfinate (R$^1$=Cl, F), and also N-methylpiperazine; methyl-[8-piperazin-1-yl-4-(3-chlorophenylsulfonyl)quinolin-3-yl]-amine 1.7(2), LCMS (M+1) 417; $^1$H NMR (DMSO-D6, 400 MHz) δ 2.98 (t, $J_1$=13.35 Hz, $J_2$=0.39 Hz, 3H), 3.06 (m, 2H), 3.14 (m, 2H), 3.42 (m, 2H), 3.50 (m, 2H), 5.26 (m, 2H), 6.64 (t, $J_1$=7.80 Hz, $J_2$=1.46 Hz, 1H), 7.27 (m, 3H), 7.55 (s, 1H), 7.67 (t, $J_1$=12.08 Hz, $J_2$=1.74 Hz, 1H), 7.77 (m, 2H); methyl-[8-piperazin-1-yl-4-(3-fluorophenylsulfonyl)quinolin-3-yl]-amine 1.7(3), LCMS (M+1) 401; $^1$H NMR (DMSO-D6, 400 MHz) δ 2.98 (t, $J_1$=13.35 Hz, $J_2$=0.39 Hz, 3H), 3.06 (m, 2H), 3.12 (m, 2H), 3.39 (m, 2H), 3.50 (m, 2H), 5.26 (m, 2H), 6.65 (t, $J_1$=7.80 Hz, $J_2$=1.46 Hz, 1H), 7.20 (t, $J_1$=8.16 Hz, $J_2$=0.28 Hz, 1H), 7.30 (m, 2H), 7.56 (s, 1H), 7.66 (m, 1H), 7.76 (t, $J_1$=7.53 Hz, $J_2$=1.69 Hz, 1H), 7.78 (m, 1H); methyl-[8-(4-methylpiperazin-1-yl)-4-phenylsulfonylquinolin-3-yl]-amine 1.7(4), LCMS (M+1) 397; $^1$H NMR (DMSO-D6, 400 MHz) δ2.29 (t, $J_1$=13.35 Hz, $J_2$=0.99 Hz, 3H), 2.53 (m, 2H), 2.63 (m, 2H), 2.98 (t, $J_1$=13.35 Hz, $J_2$=0.39 Hz, 3H), 3.42 (m, 2H), 3.52 (m, 2H), 6.65 (t, $J_1$=7.80 Hz, $J_2$=1.46 Hz, 1H), 7.22 (d.d, $J_1$=8.16 Hz, $J_2$=0.28 Hz, 1H), 7.38 (m, 2H), 7.55 (s, 1H), 7.63 (d.d, $J_1$=7.58 Hz, $J_2$=1.25 Hz, 1H), 7.78 (d, J=0.16 Hz, 1H), 7.86 (m, 2H), 7.93 (d, J=7.53 Hz, 1H); methyl-[8-(4-methylpiperazin-1-yl)-4-(3-chlorophenylsulfonyl)quinolin-3-yl]-amine 1.7(5), LCMS (M+1) 431; $^1$H NMR (DMSO-D6, 400 MHz) δ 2.28 (t, $J_1$=13.35 Hz, $J_2$=0.99 Hz, 3H), 2.55 (m, 2H), 2.63 (m, 2H), 2.98 (t, $J_1$=13.35 Hz, $J_2$=0.39 Hz, 3H), 3.41 (m, 2H), 3.50 (m, 2H), 6.65 (t, $J_1$=7.80 Hz, $J_2$=1.46 Hz, 1H), 7.22 (d.d, $J_1$=8.16 Hz, $J_2$=0.28 Hz, 1H), 7.28 (t, $J_1$=8.04 Hz, $J_2$=0.51 Hz, 1H), 7.52 (d, J=2.46 Hz, 1H); 7.55 (m, 1H), 7.79 (d, J=0.16 Hz, 1H), 7.85 (m, 2H), 7.94 (s, 1H); methyl-[8-(4-methylpiperazin-1-yl)-4-(3-fluorophenylsulfonyl) quinolin-3-yl]-amine 1.7(6), LCMS (M+1) 415; $^1$H NMR (DMSO-D6, 400 MHz) δ 2.28 (t, $J_1$=13.35 Hz, $J_2$=0.99 Hz, 3H), 2.55 (m, 2H), 2.63 (m, 2H), 2.98 (t, $J_1$=13.35 Hz, $J_2$=0.39 Hz, 3H), 3.44 (m, 2H), 3.50 (m, 2H), 6.63 (t, $J_1$=7.80 Hz, $J_2$=1.46 Hz, 1H), 7.22 (d.d, $J_1$=8.16 Hz, $J_2$=0.28 Hz, 1H), 7.30 (m, 2H), 7.56 (m, 1H); 7.67 (m, 1H), 7.76 (t, $J_1$=7.53 Hz, $J_2$=1.69 Hz, 1H), 7.78 (m, 1H), 7.86 (s, 1H).

EXAMPLE 15

General Method for Preparation of Methyl-(4-phenylsulfonyloxazol-5-yl)-amines 1.8. Scheme 14

A solution of Na benzenesulfinate 9(2) (0.1 mol) in water (50 ml) and tetrabutylammonium bromide (0.01 mol) were added to a solution of N-(1,2,2,2-tetrachloroethyl)-amide 9(1) (0.1 mol) in benzene (50 ml). The mixture was stirred for 1 h at 20° C. and for 3 h at 60° C. Organic layer was separated, dried over $MgSO_4$, the solvent was distilled off in vacuo, the residue was recrystallized from ethanol, it gave N-(1-phenylsulfinyl-2,2,2-trichloro-ethyl)-amide 9(3), yield 65-70%.

$K_2CO_3$ (0.25 mol) was added at stirring to a solution of compound 9(3) (0.1 mol) in DMF (50 ml), the resultant mixture was refluxed for 3 h, after that the reaction mixture was evaporated in vacuo, water was added to the residue, and after stirring for 15 min the precipitated solid was filtered off, washed with water, dried in vacuo and recrystallized from ethanol. It gave 5-chloroxazole 9(4), yield 70-75%.

A mixture of 5-chloroxazole 9(4) (1 mmol), $K_2CO_3$ (2 mmol) and methylamine (1.5 mmol) in DMF (5 ml) was heated at 100° C. for 4 h, then, the reaction mixture was evaporated in vacuo, water was added, the precipitated solid was filtered off and recrystallized from iso-propanol, it gave appropriate methyl-(4-phenylsulfonyloxazol-4-yl)-amines 1.8, yield 60-85%.

Compounds 1.8(2)-1.8(9) were prepared in analogous manner using either N-(1,2,2,2-tetrachloroethyl)acetamide, or 4-acetyl-N-(1,2,2,2-tetrachloroethyl)piperazine-1-carboxamide or 4-methyl-N-1,2,2,2-tetrachloroethyl)piperazine-1-carboxamide as amide 9(1), and also 3-chloro- and 3-fluoro-Na phenylsulfinate; methyl-[2-methyl-4-(3-chlorophenylsulfonyl)oxazol-5-yl]-amine 1.8(2), LCMS (M+1) 287; $^1$H NMR (DMSO-D6, 400 MHz) δ 2.41 (d, J=2.88 Hz, 3H), 3.01 (d, J=13.35 Hz, 3H), 6.58 (s, 1H), 7.52 (t, $J_1$=8.04 Hz, $J_2$=1.69 Hz, 1H), 7.58 (d, J=7.53 Hz, 1H), 7.83 (t, $J_1$=7.53 Hz, $J_2$=2.46 Hz, 1H), 8.23 (t, $J_1$=2.46 Hz, $J_2$=0.51 Hz, 1H); methyl-[2-methyl-4-(3-fluorophenylsulfonyl)oxazol-5-yl]-amine 1.8(3), LCMS (M+1) 271; $^1$H NMR (DMSO-D6, 400 MHz) δ 2.41 (d, J=2.88 Hz, 3H), 3.01 (d, J=13.35 Hz, 3H), 6.58 (s, 1H), 7.26 (t, $J_1$=8.24 Hz, $J_2$=1.69 Hz, 1H), 7.65 (d, J=7.53 Hz, 1H), 7.73 (m, 2H); methyl-(2-piperazin-1-yl-4-phenylsulfonyloxazol-5-yl)-amine 1.8(4), LCMS (M+1) 323; $^1$H NMR (DMSO-D6, 400 MHz) δ 2.93 (m, 2H), 3.01 (d, J=13.35 Hz, 3H), 3.03 (m, 2H), 3.54 (m, 2H), 3.66 (m, 2H), 5.90 s, 2H), 7.69 (t, $J_1$=7.58 Hz, $J_2$=1.25 Hz, 1H), 7.77 (d, J=7.53 Hz, 2H), 7.95 (m, 2H); methyl-[2-piperazin-1-yl-4-(3-chlorophenylsulfonyl)oxazol-5-yl]-amine 1.8(5), LCMS (M+1) 357; $^1$H NMR (DMSO-D6, 400 MHz) δ 2.94 (m, 2H), 3.01 (d, J=13.35 Hz, 3H), 3.04 (m, 2H), 3.56 (m, 2H), 3.68 (m, 2H), 5.90 (m, 2H), 7.51 (t, $J_1$=8.04 Hz, $J_2$=1.69 Hz, 1H), 7.58 (d, J=7.53 Hz, 2H), 7.86 (m, 1H), 8.25 (t, $J_1$=2.46 Hz, $J_2$=0.51 Hz, 1H); methyl-[2-piperazin-1-yl-4-(3-fluorophenylsulfonyl)oxazol-5-yl]-amine 1.8(6), LCMS (M+1) 341; $^1$H NMR (DMSO-D6, 400 MHz) δ 2.94 (m, 2H), 3.01 (d, J=13.35 Hz, 3H), 3.04 (m, 2H), 3.56 (m, 2H), 3.68 (m, 2H), 5.90 (m, 2H), 7.25 (t, $J_1$=8.24 Hz, $J_2$=1.69 Hz, 1H), 7.62 (m, 1H), 7.79 (m, 2H); methyl-[2-(4-methylpiperazin-1-yl)-4-phenylsulfonyloxazol-5-yl]-amine 1.8(7), LCMS (M+1) 337; $^1$H NMR (DMSO-D6, 400 MHz) δ 2.36 (t, $J_1$=13.35 Hz, $J_2$=0.99 Hz, 3H), 2.47 (m, 2H), 2.55 (m, 2H), 3.01 (d, J=13.35 Hz, 3H), 3.63 (m, 2H), 3.73 (m, 2H), 7.69 (t, $J_1$=7.58 Hz, $J_2$=1.51 Hz, 1H), 7.77 (m, 2H), 7.94 (m, 2H), 9.26 (s, 1H); methyl-[2-(4-methylpiperazin-1-yl)-4-(3-chlorophenylsulfonyl)oxazol-5-yl]-amine 1.8(8), LCMS (M+1) 371; $^1$H NMR (DMSO-D6, 400 MHz) δ 2.36 (t, $J_1$=13.35 Hz, $J_2$=0.99 Hz, 3H), 2.47 (m, 2H), 2.55 (m, 2H), 3.01 (d, J=13.35 Hz, 3H), 3.63 (m, 2H), 3.71 (m, 2H), 7.52 (t, $J_1$=8.04 Hz, $J_2$=1.69 Hz, 1H), 7.59 (d, J=7.53 Hz, 1H), 7.87 (m, 2H), 8.26 (s, 1H), 9.26 (s, 1H); methyl-[2-(4-methylpiperazin-1-yl)-4-(3-fluorophenylsulfonyl)oxazol-5-yl]-amine 1.8(9), LCMS (M+1) 355; $^1$H NMR (DMSO-D6, 400 MHz) δ 2.36 (t, $J_1$=13.35 Hz, $J_2$=0.99 Hz, 3H), 2.47 (m, 2H), 2.55 (m, 2H), 3.01 (d, J=13.35 Hz, 3H), 3.65 (m, 2H), 3.73 (m, 2H), 7.26 (t, $J_1$=8.24 Hz, $J_Z$=1.69 Hz, 1H), 7.63 (m, 1H), 7.80 (m, 2H), 9.26 (s, 1H).

Methyl-(2-furan-2-yl-4-phenylsulfonyl-oxazol-5-yl)]-amines and methyl-(2-thiophen-2-yl-4-phenylsulfonyl-oxazol-5-yl)-amines were synthesized in analogous manner, provided that, N-(1,2,2,2-tetrachloroethyl)furan-2-carboxamide and N-(1,2,2,2-tetrachloroethyl)thiophene-2-carboxamide were used as 9(1)-amide, respectively. Methyl-[4-(4-methylphenylsulfonyl)-2-furan-2-yl-oxazol-5-yl]-amine 1.8 (7): LCMS (M+1) 319; $^1$H NMR (DMSO-d$_6$, 400 MHz) δ 7.84 (d.d, $J_1$=1.8 Hz, $J_2$=0.8 Hz, 1H), 7.77 (d, J=8.2 Hz, 2H), 7.48 (br.s, 1H), 7.40 (d, J=8.2 Hz, 2H), 6.98 (d.d, $J_1$=3.6 Hz, $J_2$=0.8 Hz, 1H), 6.64 (d.d, $J_1$=3.6 Hz, $J_2$=1.8 Hz, 1H), 2.96 (s, 3H), 2.36 (s, 3H). Methyl-[2-furan-2-yl-4-(4-chlorophenylsulfonyl)-oxazol-5-yl]-amine 1.8(9): LCMS (M+1) 339; $^1$H NMR (DMSO-d$_6$, 400 MHz) δ 7.89 (m, 2H), 7.85 (d.d, $J_1$=2.0 Hz, $J_2$=0.8 Hz, 1H), 7.68 (m, 2H), 7.59 (br.s, 1H), 7.00 (d.d, $J_1$=3.6 Hz, $J_2$=0.8 Hz, 1H), 6.65 (d.d, $J_1$=3.6 Hz, $J_2$=2.0 Hz, 1H), 2.97 (s, 3H). Methyl-[2-thiopen-2-yl-4-(4-chlorophenylsulfonyl)oxazol-5-yl]-amine 1.8(11): LCMS (M+1) 355; $^1$H NMR (DMSO-d$_6$, 400 MHz) δ 7.89 (m, 2H), 7.69 (m, 3H), 7.59 (br.s, 1H), 7.54 (d.d, $J_1$=3.8 Hz, $J_2$=0.6 Hz, 1H), 7.15 (d.d, $J_1$=4.6 Hz, $J_2$=3.8 Hz, 1H), 2.98 (s, 3H).

EXAMPLE 16

Determination of Antagonistic Activity of Substituted Methyl-Amines of the General Formula 1 Towards Serotonin 5-HT$_6$ Receptors Compounds of the general formula 1 were tested for their ability to prevent 5-HT$_6$ receptors activation by serotonin. HEK 293 cells (cells of human embryo's kidney) with artificially expressed 5-HT$_6$ receptor, activation of which by serotonin leads to increasing the concentration of intracellular cAMP, were used. The level of intracellular cAMP was determined using reagent kit LANCE cAMP (Perkin Elmer) according to the method described by the manufacturer of the kit: //las.perkinelmer.com/content/Manuals/-MAN_LANCEcAMP384KitUser.pdf]. Effectiveness of the compounds was estimated by their ability to reduce the level of intracellular cAMP induced by serotonin. Table 2 presents data concerning antagonistic activity K$_i$ for some compounds of the general formula 1 towards serotonin 5-HT$_6$ receptors in the setting of functional assay.

TABLE 2

Antagonist activity K$_i$ of compounds of the general formula 1 towards serotonin 5-HT$_6$ receptors in the setting of functional assay.

| No | Antagonist formula | K$_i$, nM |
|---|---|---|
| 1.1(9) | | 0.58 |
| 1.1(13) | | 153.33 |
| 1.1(14) | | 48.29 |

TABLE 2-continued

Antagonist activity $K_i$ of compounds of the general formula 1 towards serotonin 5-HT$_6$ receptors in the setting of functional assay.

| No | Antagonist formula | $K_i$, nM |
|---|---|---|
| 1.2.1(4) | | 2.01 |
| 1.2.2(4) | | 0.95 |
| 1.3(5) | | 9.58 |
| 1.4.1(1) | | 19.0 |
| 1.4.1(1)•HCl | | 19.7 |
| 1.4.1(4) | | 55.7 |
| 1.4.1(6) | | 6.47 |
| 1.4.2(4) | | 12.9 |
| 1.5(1)•2HCl | | 0.07 |
| 1.5(7) | | 3.29 |

TABLE 2-continued

Antagonist activity $K_i$ of compounds of the general formula 1 towards serotonin 5-HT$_6$ receptors in the setting of functional assay.

| No | Antagonist formula | $K_i$, nM |
|---|---|---|
| 1.5(8) | 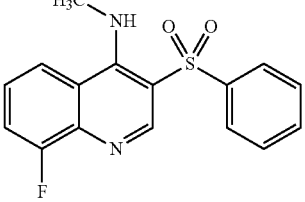 | 3.4 |
| 1.6(4) | 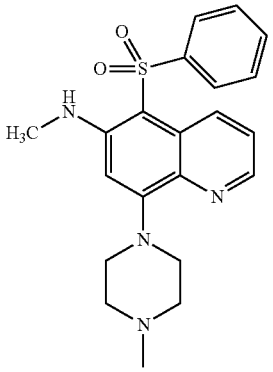 [SMILES: CNc1cc(N2CCN(C)CC2)c2ncccc2c1S(=O)(=O)c1ccccc1] | 7.83 |
| 1.7(1) | 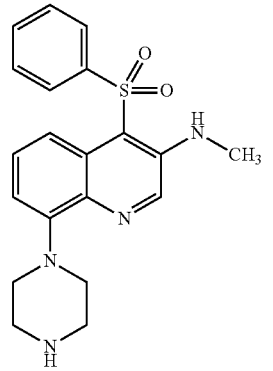 [SMILES: CNc1cnc2c(N3CCNCC3)cccc2c1S(=O)(=O)c1ccccc1] | 2.7 |
| 1.8(7) | 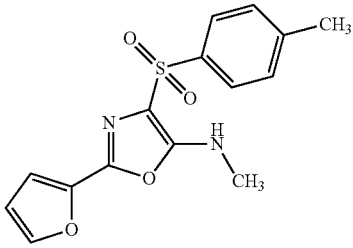 [SMILES: CNc1oc(-c2ccco2)nc1S(=O)(=O)c1ccc(C)cc1] | 1.4 |
| 1.8(8) | 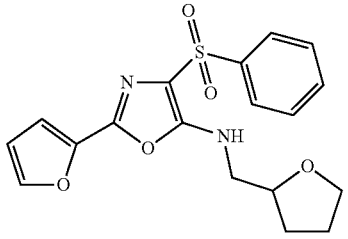 [SMILES: O=S(=O)(c1ccccc1)c1nc(-c2ccco2)oc1NCC1CCCO1] | 234.8 |
| 1.8(9) | 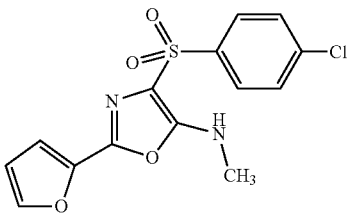 [SMILES: CNc1oc(-c2ccco2)nc1S(=O)(=O)c1ccc(Cl)cc1] | 587.5 |
| 1.8(11) | 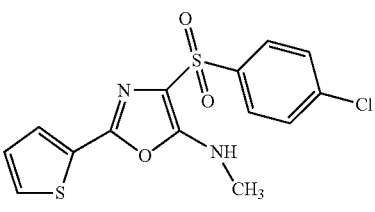 [SMILES: CNc1oc(-c2cccs2)nc1S(=O)(=O)c1ccc(Cl)cc1] | 2.2 |
| 1.8(12) | 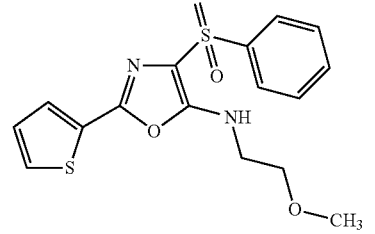 | 44.4 |
| 1.8(13) | 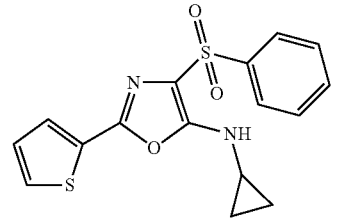 [SMILES: O=S(=O)(c1ccccc1)c1nc(-c2cccs2)oc1NC1CC1] | 57.4 |
| 1.8(14) | 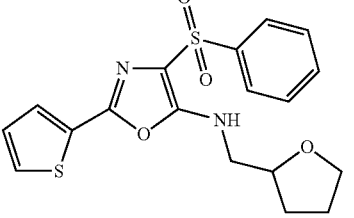 | 188.5 |

Data presented in Table 2 show that the tested compounds exhibit high antagonistic activity towards serotonin 5-HT$_6$ receptors.

EXAMPLE 17

Preparation of pharmaceutical composition in the form of tablets. Starch (1600 mg), ground lactose (1600 mg), talk (400 mg) and compound 1.5(1) (1000 mg) were mixed together and pressed into bar. The resultant bar was comminuted into granules and sifted through sieve to collect granules of 14-16 mesh. The granules thus obtained were shaped into tablets of suitable form weighing 560 mg each.

EXAMPLE 18

Preparation of pharmaceutical composition in the form of capsules. Compound 1.5(1) and lactose powder were carefully mixed in ratio 2:1. The resultant powdery mixture was packed into gelatin capsules of suitable size by 300 mg to a capsule.

EXAMPLE 19

Preparation of pharmaceutical composition in the form of compositions for intramuscular, intraperitoneal or hypodermic injections. Compound 1.5(1) (500 mg) chlorobutanol (300 mg), propylene glycol (2 ml), and injectable water (100 ml) were mixed together. The resultant solution was filtered and placed into 1 ml ampoules, which were sealed and sterilized in an autoclave.

EXAMPLE 20

Nootropic action (enhancement of memory disturbed by Scopolamine) of compounds of the general formula 1 in the test "Passive Avoidance of mice in the Shuttle Chamber". A shuttle chamber (Ugo Basile, Italy) consisted of two sections was used. The walls of one section were opaque, while the other section had a transparent cover. The sections were connected through a hole which could be overlapped by vertical door. The floor of the dark section was made of transverse metal bars on which DC current impulses could be fed. Experiments were carried out in aged male mice of BALB/c line weighing 20-25 grams.

On the first day of the experiment 30 minutes before training mice were injected intraperitoneally with physiological solution, Scopolamine (0.3 mg/kg), or Scopolamine in combination with compound 1.5(1). Each group consisted of 8 animals at least. The animals were placed in the light section, and latent period of the first entry into the dark chamber was registered. Then the vertical door was closed and the animal was punished by 0.6 mA DC current for 3 seconds. After that the animal was taken back to its home cage. In 22-24 hours the same animal was placed again in the light section of the shuttle chamber and latent period of its first entry into the dark section, the total time of its stay in the light section and the number of entries into dark section were registered. Each monitoring lasted for 5 minutes.

Experiment was carried out during the day-time in isolated laboratory using "white noise" of about 70 dB intensity above human audibility threshold.

Scopolamine causes memory disturbance which was expressed in the form of decreasing of latent period of the first entry into dark section, decreasing the total time of stay in light section and increasing the number of entries into dark section Analogous experiment was carried out for compounds 1.1 (9) and 1.8(7). The property of compounds 1.1(9), 1.5 (1) and 1.8(7) to improve training disturbed by Scopolamine is regarded as evidence of their nootropic action. The results obtained (FIG. 1-3) are indicative of the property of compounds 1.1(9), 1.5 (1) and 1.8(7) to produce nootropic action more effectively.

EXAMPLE 21

Nootropic action (enhancement of memory disturbed by MK-801) of compounds of the general formula 1. Experiment was carried out, as in example 20. On the first day of the experiment 30 min before training mice were injected intraperitoneally with physiological solution of MK-801 (0.1 mg/kg). In parallel, independent groups of mice were injected intraperitoneally with physiological solution of MK-801 in combination with compound 1.5(1) before training. The experiment as described above was also conducted for compounds 1.1(9) and 1.8(7). The results obtained (FIG. 4-6) testify the property of compounds 1.1(9), 1.5 (1) and 1.8(7) to produce nootropic action.

EXAMPLE 22

Anxiolytic (tranquilizing) action of compounds of the general formula 1 in "Mice Behavior in the Elevated Plus Maze" test. Compounds 1.1(9), 1.5 (1) and 1.8(7) were employed in the experiments. Arm length was 30 cm, width—5 cm, wall hight—15 cm. Two opposite arms were closed from both sides and end surfaces with transparent plexiglass; two others—lighted and opened. A mouse was placed in the maze center, and over a period of 5 minutes the number of opened and closed arms entries and duration of opened and closed arm entries were registered. Using these data index of opened arms preference was calculated as ratio of the number of entries into opened arms as well as the time spent by animal in opened arms to the whole number of entries to arms of both types or, respectively, to the total time spent in opened and closed arms. Being in normal state animals avoid opened arms (index of preference makes 0.2-0.3). Compounds with anxiolytic activity (tranquilizing activity) run this value up to 0.5-0.6 and more, and also decrease the number of defecations without changing overall physical activity (general number of arm entries).

The results obtained (FIG. 7-9) testify the ability of compounds 1.1(9), 1.5 (1) and 1.8(7) to display anxiolytic (tranquilizing) activity comparable to the activity of Buspirone and Lorazepam.

EXAMPLE 23

Appetite Control Test

Male rats of Vistar line weighing 230-360 g were housed in standard home cages with water and food available with the exception of short periods of food deprivation (16 hs) just before the Appetite test. The Appetite test was carried out in individual cages with overhead cover made of wire in the niches of which a portion of food granules was inserted. Mass of the granules was examined every 30 minutes for 3 h. On the basis of these measurements food consumption was estimated and stated in grams of food per kilogram of body mass. Placebo and compound 1.5(1) (dose 10 mg/kg) were injected intraperitoneally 60 minutes before the test. Each experimental group of animals consisted of 10 rats. Compound was dissolved in sterilized water. The injection volume was 10 ml/kg. Intact animals which were not undergone food deprivation, and animals after food deprivation, but injected with sterilized water, were used as control. Intact animals which were not undergone food deprivation and injected with sterilized water, were used as control. The experiment was carried out also using compounds 1.1(9) and 1.8(7). Test results show (FIG. 10) that compounds 1.1(9), 1.5 (1) and 1.8(7) are capable to prevent appetite rising in rats.

EXAMPLE 24

Antipsychotic activity of compounds of the general formula 1 in "Prepulse inhibition of the startle response in mice"

test. Mice of SHK line weighing about 24-30 g were used in the test. Experiments were carried out during light period of animal's diurnal. Apomorphine hydrochloride and Haloperidol were received from Sigma Chemicals Company, (USA). Apomorphine hydrochloride was dissolved in 0.1% solution of ascorbic acid prepared with sterilized water; it was introduced subcutaneously 15 minutes before the test. Haloperidol was dissolved in sterilized water using emulsifier Twin 80, it was introduced intraperitoneally 60 minutes before the test. Compound 1.5(1) was dissolved in sterilized water, it was introduced subcutaneously 60 minutes before the test. Injection volume was 10 ml/kg. Solution of ascorbic acid prepared with sterilized water and Twin 80 were injected to control group of animals.

The test instrument consisted of a chamber made of transparent plexiglass (manufacturer—Columbia Instruments Company, USA) and placed on a platform; the latter was lodged inside the sound insulating chamber. High frequency sound column transmitting acoustic stimulus was located 2 cm away from the platform. Startle of animal resulted in vibrations of platform, which were detected by analog converter and registered by computer. Level of background noise made up 65 dB. Each animal received 4 stimuli of single testing (pulse) stimulus of 50 ms duration and 105 dB or prepulsory stimulus (pre-pulse) of 20 ms duration and 85 dB, after which in 30 ms pulse stimulus of 50 ms duration and 105 dB followed. Time interval between repeated pulse or prepulse in combination with pulse stimuli made up 10 s. Inhibition of the startle in reply to prepulse-plus-pulse stimulus was calculated in percentage towards amplitude of startle in response to isolated pulse stimulus. Administration of Apomorphine, which is used in experiments on animals for modelling of psychoto-like conditions, caused reduction of prepulse inhibition of startle, which reflected the lowering of CNS ability to filter sensory stimulus. The experiment was also carried out using compounds 1.1(9) and 1.8(7).

The results of the experiment show (FIG. 11) that Haloperidol (1 mg/kg) and the tested compounds 1.1(9), 1.5 (1) and 1.8(7) (1 mg/kg) prevented disturbance of prepulse inhibition of startle caused by Apomorphine.

EXAMPLE 25

Antidepressant action of antagonists of the general formula 1 in Porsolt's Forced Swim Test. The test apparatus represented a plastic vessel filled with water up to height of 18 cm at 20-22° C. Experiments were carried out in aged male mice of BALB/c line weighing 20-24 grams. An animal was placed in water and for 15 minutes the duration of immobile hanging in water—so named behavioural despaire which is considered to be a measure of depressively-like state, was registered. The last 5 minutes of the test were used for estimation. Automated computerized detection of motion with video system and Any-maze program were used in test. The ability of compounds 1.1(9), 1.5 (1) and 1.8(7) after 4 days administration of them in doses of 1 mg/kg to diminish the given parameter (FIG. 12) is regarded as evidence of their antidepressant action.

EXAMPLE 26

Antidepressant action of compounds of the general formula 1 in tail suspension test. Experiments were carried out in aged male mice of BALB/c line weighing 20-24 grams. In the test mice were suspended by tail with scotch tape on holder over horizontal surface at a height of about 40 cm, and for 3 minutes the total duration of complete immobility episodes which is considered to be a measure of depressively-like state was registered. Automated computerized detection of motion with video system and Any-maze program were used in test. The ability of compounds 1.1(9), 1.5 (1) and 1.8(7) after 4 days administration of them in doses of 0.1 mg/kg to diminish the duration of complete immobility of mice (FIG. 13) is regarded as evidence of their antidepressant action.

INDUSTRIAL APPLICABILITY

The invention could be used in medicine, veterinary, biochemistry.

The invention claimed is:

1. A substituted methyl amine compound of general formula 1, or in a crystalline form or a pharmaceutically acceptable salt thereof,

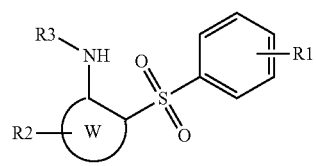

wherein:
W is an indolizine or quinoline,
R1 is a hydrogen, fluoro, chloro, methyl,
R2 is a hydrogen, fluoro, methyl, phenyl, thiophen-2-yl, furan-2-yl, pyridyl, piperazin-1-yl or 4-methylpiperazin-1-yl, and
R3 is a methyl;
or
W is benzene, R3 is a methyl, and
R1 is 3-Cl, R2 is 3-piperazin-1-yl or 3-(4-methylpiperazin-1-yl);
or
R1 is a hydrogen, and
R2 is a phenyl or pyridyl;
or
R1 is a hydrogen, fluoro, chloro, methyl, and
R2 is a 4-piperazin-1-yl or 4-(4-methylpiperazin-1-yl);
or
W is a oxazole, R3 is an optionally substituted methyl,
R1 is a fluoro or chloro, and
R2 is a methyl;
or
R1 is a hydrogen, fluoro, chloro, methyl, and
R2 is a piperazin-1-yl, 4-methylpiperazin-1-yl;
or
R1 is a hydrogen, fluoro, chloro, methyl,
R2 is a furan-2-yl, and
R3 is a (tetrahydrofuran-2-yl)methyl;
or
R1 is a hydrogen, fluoro, chloro, methyl,
R2 is a thiophen-2-yl, and
R3 is a 2-methoxyethyl.

2. The compound of claim 1, wherein W is an optionally substituted 1,2-phenylene (1.1); 1,2-indolizinene (1.4.1, 1.4.2); 3,4-quinolinene (1.5 or 1.7), 5,6-quinolinene (1.6) or 4,5-oxazolene (1.8),

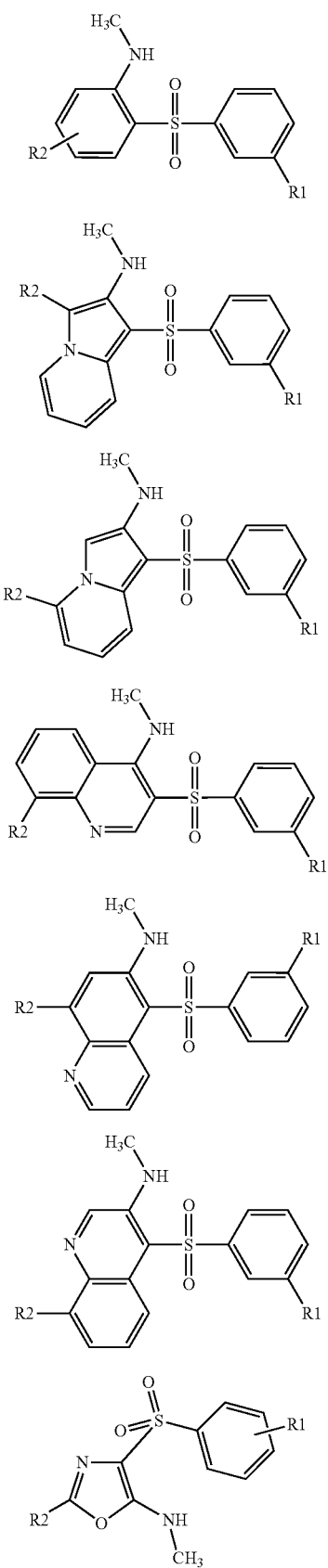

and R1 and R2 have the above meanings for the appropriate meaning of W.

3. The compound of claim 2, wherein R1=H, 3-F or 3-Cl.

4. The compound of claim 3, wherein R2 is a hydrogen, methyl, piperazin-1-yl or 4-methylpiperazin-1-yl.

5. The compound of claim 1, selected from the group consisting of methyl-[3-(piperazin-1-yl-6-(3-chlorophenylsulfonyl)phenyl]-amine 1.1(2), methyl-[3-(4-methyl-piperazin-1-yl)-6-(3-chlorophenylsulfonyl)phenyl]-amine 1.1(5), 1.1(2): R1 = 3-Cl, R2' = H,
1.1(5): R1 = 3-Cl, R2' = CH3, methyl-(4-piperazin-1-yl-6-phenylsulfonylphenyl)-amine 1.1(7), methyl-[4-piperazin-1-yl-6-(3-chlorophenylsulfonyl)phenyl]-amine 1.1(8), methyl-[4-piperazin-1-yl-6-(3-fluorophenylsulfonyl)phenyl]-amine 1.1(9), methyl-[4-(4-methylpiperazin-1-yl)-6-phenylsulfonylphenyl]-amine 1.1(10), methyl-[4-(4-methylpiperazin-1-yl)-6-(3-chlorophenylsulfonyl)phenyl]-amine 1.1(11), methyl-[4-(4-methylpiperazin-1-yl)-6-(3-fluorophenylsulfonyl)phenyl]-amine 1.1(12), 1.1(7): R1 = H, R'2 = H
1.1(8): R1 = Cl, R'2 = H
1.1(9): R1 = F, R'2 = H
1.1(10): R1 = H, R'2 = CH3
1.1.(11): R1 = Cl, R'2 = CH3
1.1.(12): R1 = F, R'2 = CH3

N-methyl-N-[4-(phenylsulfonyl)-1,1'-biphenyl-3-yl]
amine 1.1(13), methyl-(5-pyridin-3-yl-2-phenylsulfonylphenyl)-amine
1.1(14),

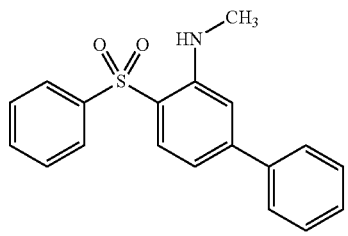

1.1(13)

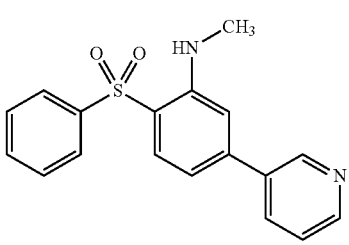

1.1(14)

methyl-(1-phenylsulfonylindolizin-2-yl)-amine 1.4.1(1),
methyl-[1-(3-chlorophenylsulfonyl)indolizin-2-yl]-amine
1.4.1(2),
methyl-[1-(3-fluorophenylsulfonyl)indolizin-2-yl]-amine
1.4.1(3),
methyl-(3-methyl-1-phenylsulfonylindolizin-2-yl)-amine
1.4.1(4),
methyl-[3-methyl-1-(3-chlorophenylsulfonyl)indolizin-2-
yl]-amine 1.4.1(5),
methyl-[3-methyl-1-(3-fluorophenylsulfonyl)indolizin-2-
yl]-amine 1.4.1(6),
methyl-(3-piperazin-1-yl-1-phenylsulfonylindolizin-2-
yl)-amine 1.4.1(7),
methyl-[3-piperazin-1-yl-1-(3-chlorophenylsulfonyl)in-
dolizin-2-yl]-amine 1.4.1(8),
methyl-[3-piperazin-1-yl-1-(3-fluorophenylsulfonyl)in-
dolizin-2-yl]-amine 1.4.1(9),
methyl-[3-(4-methylpiperazin-1-yl)-1-phenylsulfonylin-
dolizin-2-yl]-amine 1.4.1(10),
methyl-[3-(4-methylpiperazin-1-yl)-1-(3-chlorophenyl-
sulfonylindolizin-2-yl]-amine 1.4.1(11),
methyl-[3-(4-methylpiperazin-1-yl)-1-(3-fluorophenyl-
sulfonylindolizin-2-yl]-amine 1.4.1(12),

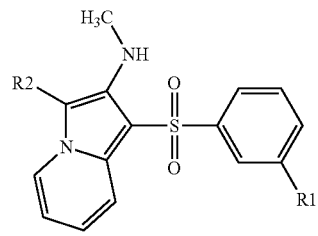

1.4.1(1-12)

1.4.1(1): R1 = R2 = H,
1.4.1(2): R1 = 3-Cl, R2 = H,
1.4.1(3): R1 = 3-F, R2 = H,
1.4.1(4): R1 = H, R2 = CH₃,
1.4.1(5): R1 = 3-Cl, R2 = CH₃,
1.4.1(6): R1 = 3-F, R2 = CH₃,
1.4.1(7): R1 = H, R2 = piperazin-1-yl;
1.4.1(8): R1 = 3-Cl, R2 = piperazine-1-yl;
1.4.1(9): R1 = 3-F, R2 = piperazine-1-yl;
1.4.1(10): R1 = H, R2 = 4-methylpiperazine-1-yl;
1.4.1(11): R1 = 3-Cl, R2 = 4-methylpiperazine-1-yl;
1.4.1(12): R1 = 3-F, R2 = 4-methylpiperazine-1-yl;

methyl-(5-methyl-1-phenylsulfonylindolizin-2-yl)-amine
1.4.2(1),
methyl-[5-methyl-1-(3-chlorophenylsulfonyl)indolizin-2-
yl]-amine 1.4.2(2),
methyl-[5-methyl-1-(3-fluorophenylsulfonyl)indolizin-2-
yl]-amine 1.4.2(3),
methyl-(5-piperazin-1-yl-1-phenylsulfonylindolizin-2-
yl)-amine 1.4.2(4),
methyl-[5-piperazin-1-yl-1-(3-chlorophenylsulfonyl)in-
dolizin-2-yl]-amine 1.4.2(5),
methyl-[5-piperazin-1-yl-1-(3-fluorophenylsulfonyl)in-
dolizin-2-yl]-amine 1.4.2(6),
methyl-[5-(4-methylpiperazin-1-yl)-1-phenylsulfonylin-
dolizin-2-yl]-amine 1.4.2(7),
methyl-[5-(4-methylpiperazin-1-yl)-1-(3-chlorophenyl-
sulfonyl)indolizin-2-yl]-amine 1.4.2(8),
methyl-[5-(4-methylpiperazin-1-yl)-1-(3-fluorophenyl-
sulfonyl)indolizin-2-yl]-amine 1.4.2(9),

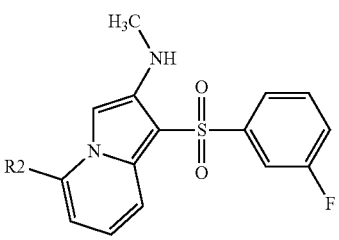

1.4.2(1-9)

1.4.2(1): R1 = H, R2 = CH₃,
1.4.2(2): R1 = 3-Cl, R2 = CH₃,
1.4.2(3): R1 = 3-F, R2 = CH₃,
1.4.2(4): R1 = H, R2 = piperazin-1-yl;
1.4.2(5): R1 = 3-Cl, R2 = piperazine-1-yl;
1.4.2(6): R1 = 3-F, R2 = piperazine-1-yl;
1.4.2(7): R1 = H, R2 = 4-methylpiperazine-1-yl;
1.4.2(8): R1 = 3-Cl, R2 = 4-methylpiperazine-1-yl;
1.4.2(9): R1 = 3-F, R2 = 4-methylpiperazine-1-yl;

methyl-(8-piperazin-1-yl-3-phenylsulfonylquinolin-4-
yl)-amine 1.5(1),
methyl-[8-piperazin-1-yl-3-(3-chlorophenylsulfonyl)
quinolin-4-yl]-amine 1.5(2),
methyl-[8-piperazin-1-yl-3-(3-fluorophenylsulfonyl)
quinolin-4-yl]-amine 1.5(3), methyl-[8-(4-methylpiperazin-1-yl)-3-phenylsulfo-
   nylquinolin-4-yl]-amine 1.5(4),
methyl-[8-(4-methylpiperazin-1-yl)-3-(3-chlorophenyl-
   sulfonyl)quinolin-4-yl]-amine 1.5(5),
methyl-[8-(4-methylpiperazin-1-yl)-3-(3-fluorophenyl-
   sulfonyl)quinolin-4-yl]-amine 1.5(6),

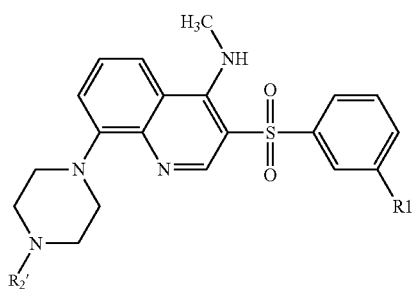

1.5(1-6)

1.5(1): R1 = R2' = H,
1.5(2): R1 = 3-Cl, R2' = H,
1.5(3): R1 = 3-F, R2' = H,
1.5(4): R1 = H, R2' = CH3,
1.5(5): R1 = 3-Cl, R2' = CH3,
1.5(6): R1 = 3-F, R2' = CH3, methyl-(8-piperazin-1-yl-5-phenylsulfonylquinolin-6-
   yl)-amine 1.6(1),
methyl-[8-piperazin-1-yl-5-(3-chlorophenylsulfonyl)
   quinolin-6-yl]-amine 1.6(2),
methyl-[8-piperazin-1-yl-5-(3-fluorophenylsulfonyl)
   quinolin-6-yl]-amine 1.6(3),
methyl-[8-(4-methylpiperazin-1-yl)-5-phenylsulfo-
   nylquinolin-6-yl]-amine 1.6(4),
methyl-[8-(4-methylpiperazin-1-yl)-5-(3-chlorophenyl-
   sulfonyl)quinolin-6-yl]-amine 1.6(5),
methyl-[8-(4-methylpiperazin-1-yl)-5-(3-fluorophenyl-
   sulfonyl)quinolin-6-yl]-amine 1.6(6),

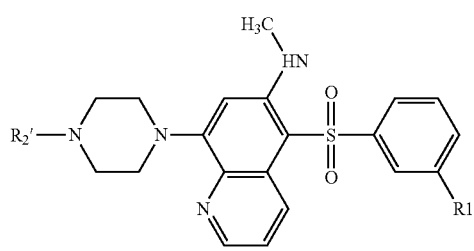

1.6(1-6)

1.6(1): R1 = R2' = H,
1.6(2): R1 = 3-Cl, R2' = H,
1.6(3): R1 = 3-F, R2' = H,
1.6(4): R1 = H, R2' = CH3,
1.6(5): R1 = 3-Cl, R2' = CH3,
1.6(6): R1 = 3-F, R2' = CH3, methyl-(8-piperazin-1-yl-4-phenylsulfonylquinolin-3-
   yl)-amine 1.7(1),
methyl-[8-piperazin-1-yl-4-(3-chlorophenylsulfonyl)
   quinolin-3-yl]-amine 1.7(2),
methyl-[8-piperazin-1-yl-4-(3-fluorophenylsulfonyl)
   quinolin-3-yl]-amine 1.7(3),
methyl-[8-(4-methylpiperazin-1-yl)-4-phenylsulfo-
   nylquinolin-3-yl]-amine 1.7(4),
methyl-[8-(4-methylpiperazin-1-yl)-4-(3-chlorophenyl-
   sulfonyl)quinolin-3-yl]-amine 1.7(5),
methyl-[8-(4-methylpiperazin-1-yl)-4-(3-fluorophenyl-
   sulfonyl)quinolin-3-yl]-amine 1.7(6),

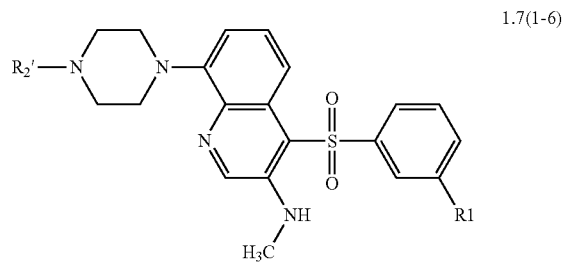

1.7(1-6)

1.7(1): R1 = R2' = H,
1.7(2): R1 = 3-Cl, R2' = H,
1.7(3): R1 = 3-F, R2' = H,
1.7(4): R1 = H, R2' = CH3,
1.7(5): R1 = 3-Cl, R2' = CH3,
1.7(6): R1 = 3-F, R2' = CH3, methyl-[2-methyl-4-(3-chlorophenylsulfonyl)oxazol-5-
   yl]-amine 1.8(2),
methyl-[2-methyl-4-(3-fluorophenylsulfonyl)oxazol-5-
   yl]-amine 1.8(3),
methyl-(2-piperazin-1-yl-4-phenylsulfonyloxazol-5-yl)-
   amine 1.8(4),
methyl-[2-piperazin-1-yl-4-(3-chlorophenylsulfonyl)ox-
   azol-5-yl]-amine 1.8(5),
methyl-[2-piperazin-1-yl-4-(3-fluorophenylsulfonyl)ox-
   azol-5-yl]-amine 1.8(6),
methyl-[2-(4-methylpiperazin-1-yl)-4-phenylsulfonylox-
   azol-5-yl]-amine 1.8(7),
methyl-[2-(4-methylpiperazin-1-yl)-4-(3-chlorophenyl-
   sulfonyl)oxazol-5-yl]-amine 1.8(8), and
methyl-[2-(4-methylpiperazin-1-yl)-4-(3-fluorophenyl-
   sulfonyl)oxazol-5-yl]-amine 1.8(9),

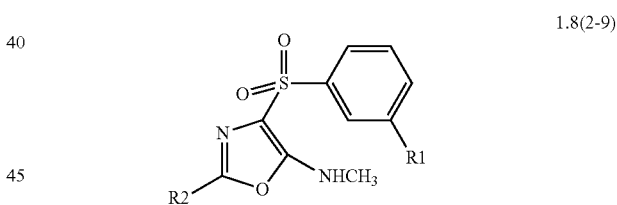

1.8(2-9)

1.8(2): R1 = 3-Cl, R2 = CH3,
1.8(3): R1 = 3-F, R2 = CH3,
1.8(4): R1 = H, R2 = piperazin-1-yl;
1.8(5): R1 = 3-Cl, R2 = piperazine-1-yl;
1.8(6): R1 = 3-F, R2 = piperazine-1-yl;
1.8(7): R1 = H, R2 = 4-methylpiperazine-1-yl
1.8(8): R1 = 3-Cl, R2 = 4-methylpiperazine-1-yl,
1.8(9): R1 = 3-F, R2 = 4-methylpiperazine-1-yl.

6. A serotonin 5-HT$_6$ receptor antagonist comprising a substituted methyl amine compound of general formula 1, or in a crystalline form, or a pharmaceutically acceptable salt thereof, according to any of claims 1-5.

7. An active component for pharmaceutical compositions and medicaments comprising at least one serotonin 5-HT$_6$ receptor antagonist according to claim 6.

8. A pharmaceutical composition for treating a CNS disease pathogenesis of which is associated with 5-HT$_6$ receptors, selected from a cognitive disorder or a neurodegenerative disease, comprising an active component according to claim 7 in a pharmaceutically effective amount and at least one pharmaceutically acceptable excipient.

9. The pharmaceutical composition of claim 8 in the form of a tablet, capsule or an injection placed in a pharmaceutically acceptable package.

10. The pharmaceutical composition of claim 8 for treating a psychic disorder or schizophrenia.

11. The pharmaceutical composition of claim 8 for treating a anxiety disorder.

12. The pharmaceutical composition of claim 8 for a mental ability improvement.

13. The pharmaceutical composition of claim 8 for treating an obesity.

14. A method for inhibiting a 5-$HT_6$ receptor comprising administering to a subject a compound of claim 1 in need thereof.

15. A substituted methyl amine compound of general formula 1 of claim 1 for investigation of molecular mechanism of serotonin 5-$HT_6$ receptor inhibition.

* * * * *